United States Patent
O'Banion

(10) Patent No.: US 12,104,163 B2
(45) Date of Patent: *Oct. 1, 2024

(54) ADENO-ASSOCIATED VIRUS VECTORS FOR TREATMENT OF RETT SYNDROME

(71) Applicant: Sarepta Therapeutics, Inc., Cambridge, MA (US)

(72) Inventor: Colin O'Banion, Durham, NC (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 97 days.

This patent is subject to a terminal disclaimer.

(21) Appl. No.: 17/406,723

(22) Filed: Aug. 19, 2021

(65) Prior Publication Data

US 2022/0056478 A1  Feb. 24, 2022

Related U.S. Application Data

(60) Provisional application No. 63/067,668, filed on Aug. 19, 2020.

(51) Int. Cl.
| | |
|---|---|
| *C12N 15/86* | (2006.01) |
| *A61K 38/18* | (2006.01) |
| *A61K 48/00* | (2006.01) |
| *A61P 25/28* | (2006.01) |
| *C07K 14/475* | (2006.01) |
| *C07K 14/61* | (2006.01) |

(52) U.S. Cl.
CPC ............ *C12N 15/86* (2013.01); *A61K 38/185* (2013.01); *A61K 48/0058* (2013.01); *A61K 48/0066* (2013.01); *A61P 25/28* (2018.01); *C07K 14/475* (2013.01); *C07K 14/61* (2013.01); *C12N 2750/14143* (2013.01); *C12N 2750/14171* (2013.01); *C12N 2830/008* (2013.01); *C12N 2830/15* (2013.01); *C12N 2830/38* (2013.01); *C12N 2830/50* (2013.01)

(58) Field of Classification Search
CPC ....... C12N 15/86; A61P 25/28; C07K 14/475; C07K 14/61
See application file for complete search history.

(56) References Cited

U.S. PATENT DOCUMENTS

| | | |
|---|---|---|
| 4,039,388 A | 8/1977 | Gal et al. |
| 4,501,729 A | 2/1985 | Boucher et al. |
| 4,968,603 A | 11/1990 | Slamon et al. |
| 5,139,941 A | 8/1992 | Muzyczka et al. |
| 5,328,470 A | 7/1994 | Nabel et al. |
| 5,399,346 A | 3/1995 | Anderson et al. |
| 5,478,745 A | 12/1995 | Samulski et al. |
| 5,658,776 A | 8/1997 | Flotte et al. |
| 5,686,240 A | 11/1997 | Schuchman et al. |
| 5,863,541 A | 1/1999 | Samulski et al. |
| 5,869,248 A | 2/1999 | Yuan et al. |
| 5,877,022 A | 3/1999 | Stinchcomb et al. |
| 5,882,652 A | 3/1999 | Valdes et al. |
| 5,905,040 A | 5/1999 | Mazzara et al. |
| 5,916,563 A | 6/1999 | Young et al. |
| 5,962,313 A | 10/1999 | Podsakoff |
| 6,013,487 A | 1/2000 | Mitchell |
| 6,040,183 A | 3/2000 | Ferrari et al. |
| 6,083,702 A | 7/2000 | Mitchell et al. |
| 6,093,570 A | 7/2000 | Ferrari et al. |
| 6,156,303 A | 12/2000 | Russell et al. |
| 6,180,613 B1 | 1/2001 | Kaplitt et al. |
| 6,426,198 B1 | 7/2002 | Carstea et al. |
| 6,468,524 B1 | 10/2002 | Chiorini et al. |
| 6,468,798 B1 | 10/2002 | Debs et al. |
| 6,503,888 B1 | 1/2003 | Kaplitt et al. |
| 6,544,785 B1 | 4/2003 | Palese et al. |
| 6,562,958 B1 | 5/2003 | Breton et al. |
| 6,733,757 B2 | 5/2004 | Patel et al. |
| 6,822,071 B1 | 11/2004 | Stephens et al. |
| 6,962,815 B2 | 11/2005 | Bartlett |
| 6,984,517 B1 | 1/2006 | Chiorini et al. |
| 7,045,675 B2 | 5/2006 | Carstea et al. |
| 7,071,172 B2 | 7/2006 | McCown et al. |
| 7,105,345 B2 | 9/2006 | Wilson et al. |
| 7,198,951 B2 | 4/2007 | Gao et al. |
| 7,201,898 B2 | 4/2007 | Monahan et al. |

(Continued)

FOREIGN PATENT DOCUMENTS

| | | |
|---|---|---|
| EP | 1033405 A2 | 9/2000 |
| EP | 1777296 A2 | 4/2007 |
| EP | 1887081 A2 | 2/2008 |
| EP | 2194140 A2 | 6/2010 |

(Continued)

OTHER PUBLICATIONS

Kells et al (AAV-Mediated Gene Delivery of BDNF or GDNF Is Neuroprotective in a Model of Huntington Disease. Mol Therapy, vol. 9, May 2004) (Year: 2004).*
Kawashima et al (Synaptic activity-responsive element in the Arc/Arg3.1 promoter essential for synapse-to-nucleus signaling in activated neurons. PNAS, vol. 106, Jan. 2009) (Year: 2009).*
pSub201 plasmid (Addgene Vector database). (Year: 1987).*
Wilmott et al (A User's Guide to the Inverted Terminal Repeats of Adeno-Associated Virus. Human Gene Therapy Methods, vol. 30, 2019) (Year: 2019).*
An et al (Distinct Role of Long 30 UTR BDNF mRNA in Spine Morphology and Synaptic Plasticity in Hippocampal Neurons. Cell, vol. 134, Jul. 2008). (Year: 2008).*
NCBI BLAST alignment of human BDNF gene with mouse BDNF long 3'UTR. (Year: 2023).*

(Continued)

*Primary Examiner* — Valarie E Bertoglio
*Assistant Examiner* — Matasha Dhar
(74) *Attorney, Agent, or Firm* — Sterne, Kessler, Goldstein & Fox P.L.L.C.

(57) ABSTRACT

The disclosure provides nucleic acids (comprising AAV expression cassettes), AAV vectors, and compositions for use in methods for treating and/or delaying the onset of diseases associated with mutations in the mecp2 gene, such as Rett Syndrome. Also, provided herein are methods for treating and/or delaying the onset of brain-derived neurotrophic factor (BDNF)-associated diseases.

27 Claims, 18 Drawing Sheets
(3 of 18 Drawing Sheet(s) Filed in Color)

Specification includes a Sequence Listing.

(56) References Cited

U.S. PATENT DOCUMENTS

| | | |
|---|---|---|
| 7,214,786 B2 | 5/2007 | Kovalic et al. |
| 7,252,997 B1 | 8/2007 | Hallek et al. |
| 7,259,151 B2 | 8/2007 | Arbetman et al. |
| 7,282,199 B2 | 10/2007 | Gao et al. |
| 7,314,912 B1 | 1/2008 | Hallek et al. |
| 7,473,531 B1 | 1/2009 | Dornon |
| 7,588,772 B2 | 9/2009 | Kay et al. |
| 7,712,893 B2 | 5/2010 | Dobashi |
| 7,718,424 B2 | 5/2010 | Chiorini et al. |
| 7,749,492 B2 | 7/2010 | Bartlett et al. |
| 7,777,097 B2 | 8/2010 | Glazebrook et al. |
| 7,790,449 B2 | 9/2010 | Gao et al. |
| 7,867,484 B2 | 1/2011 | Samulski et al. |
| 7,892,809 B2 | 2/2011 | Bowles et al. |
| 7,906,111 B2 | 3/2011 | Wilson et al. |
| 8,067,014 B2 | 11/2011 | Kay et al. |
| 8,299,321 B2 | 10/2012 | Cao |
| 8,318,480 B2 | 11/2012 | Gao et al. |
| 8,343,764 B2 | 1/2013 | Abad et al. |
| 8,445,267 B2 | 5/2013 | Zhong et al. |
| 8,628,966 B2 | 1/2014 | Chatterjee et al. |
| 8,664,475 B2 | 3/2014 | Puzio et al. |
| 8,679,837 B2 | 3/2014 | Zolotukhin et al. |
| 8,734,809 B2 | 5/2014 | Gao et al. |
| 8,802,440 B2 | 8/2014 | Zhong et al. |
| 8,889,641 B2 | 11/2014 | Asokan et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,952,217 B2 | 2/2015 | Puzio et al. |
| 8,962,332 B2 | 2/2015 | Gao et al. |
| 9,012,224 B2 | 4/2015 | Bowles et al. |
| 9,066,966 B2 | 6/2015 | Puccio et al. |
| 9,157,098 B2 | 10/2015 | Zhong et al. |
| 9,409,953 B2 | 8/2016 | Asokan et al. |
| 9,441,244 B2 | 9/2016 | Schaffer et al. |
| 9,475,845 B2 | 10/2016 | Asokan et al. |
| 9,567,376 B2 | 2/2017 | Cronin et al. |
| 9,585,971 B2 | 3/2017 | Deverman et al. |
| 9,587,250 B2 | 3/2017 | Gao et al. |
| 9,598,468 B2 | 3/2017 | Weigel-Van Aken et al. |
| 9,611,302 B2 | 4/2017 | Srivastava et al. |
| 9,623,120 B2 | 4/2017 | Chatterjee et al. |
| 9,677,088 B2 | 6/2017 | Nakai et al. |
| 9,677,089 B2 | 6/2017 | Gao et al. |
| 9,683,268 B2 | 6/2017 | Barouch et al. |
| 9,695,220 B2 | 7/2017 | Vandenberghe et al. |
| 9,719,070 B2 | 8/2017 | Vandenberghe et al. |
| 9,725,485 B2 | 8/2017 | Srivastava et al. |
| 9,737,618 B2 | 8/2017 | Wilson et al. |
| 9,737,619 B2 | 8/2017 | Ansell et al. |
| 9,775,918 B2 | 10/2017 | Zhong et al. |
| 9,777,291 B2 | 10/2017 | Chatterjee et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 9,834,789 B2 | 12/2017 | Chatterjee et al. |
| 9,839,696 B2 | 12/2017 | Chatterjee et al. |
| 9,879,275 B2 | 1/2018 | Nadzan et al. |
| 9,890,396 B2 | 2/2018 | Chatterjee et al. |
| 9,909,142 B2 | 3/2018 | Yazicioglu et al. |
| 9,920,097 B2 | 3/2018 | Zhong et al. |
| 9,944,908 B2 | 4/2018 | Vaten et al. |
| 9,976,157 B2 | 5/2018 | Poraty-Gavra et al. |
| 10,011,640 B2 | 7/2018 | Srivastava et al. |
| 10,072,251 B2 | 9/2018 | Gao et al. |
| 10,077,291 B2 | 9/2018 | Asokan et al. |
| 10,081,659 B2 | 9/2018 | Chiorini et al. |
| 10,119,125 B2 | 11/2018 | Vandenberghe et al. |
| 10,214,566 B2 | 2/2019 | Schaffer et al. |
| 10,337,027 B2 | 7/2019 | Puccio et al. |
| 10,369,193 B2 | 8/2019 | Passini et al. |
| 10,385,320 B2 | 8/2019 | Kay et al. |
| 10,392,632 B2 | 8/2019 | Wright et al. |
| 10,406,244 B2 | 9/2019 | Kay et al. |
| 10,414,803 B2 | 9/2019 | Nathwani et al. |
| 10,426,844 B2 | 10/2019 | Agbandje-McKenna et al. |
| 10,526,627 B2 | 1/2020 | Skuratowicz et al. |
| 10,668,094 B2 | 6/2020 | Karlish |
| 10,745,447 B2 | 8/2020 | Asokan et al. |
| 10,907,176 B2 | 2/2021 | Asokan et al. |
| 11,077,128 B2 | 8/2021 | Karlish |
| 2002/0192189 A1 | 12/2002 | Xiao et al. |
| 2003/0017131 A1 | 1/2003 | Park et al. |
| 2003/0053990 A1 | 3/2003 | Rabinowitz et al. |
| 2003/0225017 A1 | 12/2003 | Murdin et al. |
| 2004/0013645 A1 | 1/2004 | Monahan et al. |
| 2004/0031072 A1 | 2/2004 | La Rosa et al. |
| 2004/0071659 A1 | 4/2004 | Chang et al. |
| 2004/0166519 A1 | 8/2004 | Cargill et al. |
| 2004/0214272 A1 | 10/2004 | La Rosa et al. |
| 2005/0287122 A1 | 12/2005 | Bartlett et al. |
| 2006/0107345 A1 | 5/2006 | Alexandrov et al. |
| 2006/0123505 A1 | 6/2006 | Kikuchi et al. |
| 2006/0171926 A1 | 8/2006 | Passini et al. |
| 2006/0236419 A1 | 10/2006 | La Rosa et al. |
| 2007/0015238 A1 | 1/2007 | Snyder et al. |
| 2007/0124833 A1 | 5/2007 | Abad et al. |
| 2007/0196338 A1 | 8/2007 | Samulski et al. |
| 2007/0243526 A1 | 10/2007 | Kay et al. |
| 2008/0229439 A1 | 9/2008 | La Rosa et al. |
| 2009/0215879 A1 | 8/2009 | Diprimio et al. |
| 2009/0221620 A1 | 9/2009 | Luke et al. |
| 2009/0275107 A1 | 11/2009 | Lock et al. |
| 2009/0317417 A1 | 12/2009 | Vandenberghe et al. |
| 2010/0037352 A1 | 2/2010 | Alexandrov et al. |
| 2010/0047174 A1 | 2/2010 | Kay et al. |
| 2010/0095387 A1 | 4/2010 | Smith et al. |
| 2011/0061124 A1 | 3/2011 | Nadzan et al. |
| 2011/0067143 A2 | 3/2011 | La Rosa et al. |
| 2011/0124048 A1 | 5/2011 | Yun |
| 2011/0131679 A2 | 6/2011 | La Rosa et al. |
| 2011/0209246 A1 | 8/2011 | Kovalic et al. |
| 2011/0214206 A1 | 9/2011 | La Rosa et al. |
| 2011/0236353 A1 | 9/2011 | Wilson et al. |
| 2011/0294218 A1 | 12/2011 | Chatterjee et al. |
| 2012/0009268 A1 | 1/2012 | Asokan et al. |
| 2012/0137379 A1 | 5/2012 | Gao et al. |
| 2012/0216318 A1 | 8/2012 | La Rosa et al. |
| 2012/0255046 A1 | 10/2012 | Kay et al. |
| 2012/0322861 A1 | 12/2012 | Byrne et al. |
| 2013/0096182 A1 | 4/2013 | Chatterjee et al. |
| 2013/0152224 A1 | 6/2013 | Abad et al. |
| 2013/0185831 A1 | 7/2013 | Kovalic et al. |
| 2013/0195801 A1 | 8/2013 | Gao et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0225666 A1 | 8/2013 | Kaspar et al. |
| 2013/0326723 A1 | 12/2013 | La Rosa et al. |
| 2014/0017212 A1 | 1/2014 | Rebar |
| 2014/0037585 A1 | 2/2014 | Wright et al. |
| 2014/0050701 A1 | 2/2014 | Zhong et al. |
| 2014/0056854 A1 | 2/2014 | Asokan et al. |
| 2014/0057969 A1 | 2/2014 | Frost et al. |
| 2014/0130203 A1 | 5/2014 | La Rosa et al. |
| 2014/0162319 A2 | 6/2014 | Hareendran et al. |
| 2014/0199313 A1 | 7/2014 | Plesch et al. |
| 2014/0223605 A1 | 8/2014 | Puzio et al. |
| 2014/0259218 A1 | 9/2014 | Kovalic et al. |
| 2014/0296486 A1 | 10/2014 | Gao et al. |
| 2014/0335054 A1 | 11/2014 | Gao et al. |
| 2014/0341852 A1 | 11/2014 | Srivastava et al. |
| 2015/0050302 A1 | 2/2015 | Thess |
| 2015/0079038 A1 | 3/2015 | Deverman et al. |
| 2015/0082481 A1 | 3/2015 | La Rosa et al. |
| 2015/0126588 A1 | 5/2015 | Nakai et al. |
| 2015/0133530 A1 | 5/2015 | Srivastava et al. |
| 2015/0184189 A1 | 7/2015 | Abad et al. |
| 2015/0191739 A1 | 7/2015 | La Rosa et al. |
| 2015/0197763 A1 | 7/2015 | La Rosa et al. |
| 2015/0238550 A1 | 8/2015 | McCown |
| 2015/0344911 A1 | 12/2015 | Chatterjee et al. |
| 2016/0017295 A1 | 1/2016 | Schaffer et al. |

(56) References Cited

U.S. PATENT DOCUMENTS

| | | |
|---|---|---|
| 2016/0025657 A1 | 1/2016 | Shahbazmohamadi et al. |
| 2016/0106865 A1 | 4/2016 | Zhong et al. |
| 2016/0215024 A1 | 7/2016 | Vandenberghe et al. |
| 2016/0222067 A1 | 8/2016 | Gao et al. |
| 2016/0256571 A1 | 9/2016 | Corral-Debrinski et al. |
| 2016/0264984 A1 | 9/2016 | La Rosa et al. |
| 2016/0289275 A1 | 10/2016 | Chiorini et al. |
| 2016/0319294 A1 | 11/2016 | Kovalic et al. |
| 2016/0333372 A1 | 11/2016 | Srivastava et al. |
| 2016/0361439 A1 | 12/2016 | Agbandje-McKenna et al. |
| 2016/0369299 A1 | 12/2016 | Boye et al. |
| 2017/0007720 A1 | 1/2017 | Boye et al. |
| 2017/0028082 A1 | 2/2017 | Wilson et al. |
| 2017/0049910 A1 | 2/2017 | Cronin et al. |
| 2017/0067908 A1 | 3/2017 | Nakai et al. |
| 2017/0088852 A1 | 3/2017 | Dangoor et al. |
| 2017/0088858 A1 | 3/2017 | Gao et al. |
| 2017/0096683 A1 | 4/2017 | Scaria et al. |
| 2017/0130245 A1 | 5/2017 | Kotin et al. |
| 2017/0159027 A1 | 6/2017 | Wilson et al. |
| 2017/0166926 A1 | 6/2017 | Deverman et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0240885 A1 | 8/2017 | Deverman et al. |
| 2017/0275337 A1 | 9/2017 | Srivastava et al. |
| 2017/0298323 A1 | 10/2017 | Vandenberghe et al. |
| 2017/0349911 A1 | 12/2017 | Gao et al. |
| 2018/0002722 A1 | 1/2018 | Asokan et al. |
| 2018/0030096 A1 | 2/2018 | Aslanidi et al. |
| 2018/0030479 A1 | 2/2018 | Gao et al. |
| 2018/0036428 A1 | 2/2018 | Zhong et al. |
| 2018/0066022 A1 | 3/2018 | Chalberg et al. |
| 2018/0066285 A1 | 3/2018 | Ojala et al. |
| 2018/0104289 A1 | 4/2018 | Venditti et al. |
| 2018/0105559 A1 | 4/2018 | Srivastava et al. |
| 2018/0112229 A1 | 4/2018 | Nadzan et al. |
| 2018/0119167 A1 | 5/2018 | Abad et al. |
| 2018/0135074 A1 | 5/2018 | Srivastava et al. |
| 2018/0135076 A1 | 5/2018 | Linden |
| 2018/0163227 A1 | 6/2018 | Chatterjee et al. |
| 2018/0214576 A1 | 8/2018 | Fitzgerald et al. |
| 2018/0244727 A1 | 8/2018 | Zhong et al. |
| 2018/0265863 A1 | 9/2018 | Esteves et al. |
| 2018/0355376 A1 | 12/2018 | Chiorini et al. |
| 2018/0362592 A1 | 12/2018 | Gao et al. |
| 2018/0371024 A1 | 12/2018 | Asokan et al. |
| 2019/0048041 A1 | 2/2019 | Asokan et al. |
| 2019/0055524 A1 | 2/2019 | Vandenberghe et al. |
| 2019/0085301 A1 | 3/2019 | Gao et al. |
| 2019/0100560 A1 | 4/2019 | Vandenberghe et al. |
| 2019/0249195 A1 | 8/2019 | Marsic et al. |
| 2019/0255192 A1 | 8/2019 | Kirn et al. |
| 2019/0262373 A1 | 8/2019 | Woodard et al. |
| 2019/0284576 A1 | 9/2019 | Qu et al. |
| 2019/0292561 A1 | 9/2019 | Qu et al. |
| 2019/0367562 A1 | 12/2019 | Asokan et al. |
| 2020/0109418 A1 | 4/2020 | Li et al. |
| 2020/0399321 A1 | 12/2020 | Asokan et al. |
| 2021/0115474 A1 | 4/2021 | McCoy et al. |
| 2021/0128652 A1 | 5/2021 | Dismuke |
| 2021/0324418 A1 | 10/2021 | Thomas et al. |
| 2022/0064675 A1 | 3/2022 | McCoy et al. |
| 2022/0088152 A1 | 3/2022 | Mikati |
| 2022/0089651 A1 | 3/2022 | Asokan et al. |

FOREIGN PATENT DOCUMENTS

| | | |
|---|---|---|
| EP | 2359869 A2 | 8/2011 |
| EP | 2492347 A1 | 8/2012 |
| EP | 2660325 A2 | 11/2013 |
| EP | 2315833 B1 | 4/2015 |
| EP | 1453547 B1 | 9/2016 |
| EP | 2007795 B1 | 11/2016 |
| EP | 2675484 B1 | 5/2018 |
| EP | 2263692 B1 | 9/2018 |
| EP | 2206728 B9 | 10/2018 |
| EP | 3244931 B1 | 10/2018 |
| EP | 1633767 B1 | 11/2018 |
| EP | 3060575 B1 | 12/2018 |
| EP | 3250239 B1 | 12/2018 |
| EP | 3459965 A1 | 3/2019 |
| EP | 3511021 A1 | 7/2019 |
| EP | 3108000 B1 | 8/2019 |
| JP | 2014534245 A | 12/2014 |
| RU | 2457252 C2 | 7/2012 |
| WO | WO-9005142 A1 | 5/1990 |
| WO | WO-9811244 A2 | 3/1998 |
| WO | WO-9901555 A1 | 1/1999 |
| WO | WO-0017377 A2 | 3/2000 |
| WO | WO-9961601 A9 | 3/2000 |
| WO | WO-0023477 A2 | 4/2000 |
| WO | WO-0028004 A1 | 5/2000 |
| WO | WO-0028061 A9 | 11/2000 |
| WO | WO-0111034 A2 | 2/2001 |
| WO | WO-0181581 A2 | 11/2001 |
| WO | WO-0192551 A2 | 12/2001 |
| WO | WO-0210210 A2 | 2/2002 |
| WO | WO-03000906 A2 | 1/2003 |
| WO | WO-03008540 A2 | 1/2003 |
| WO | WO-03033515 A1 | 4/2003 |
| WO | WO-03042361 A2 | 5/2003 |
| WO | WO-03052051 A2 | 6/2003 |
| WO | WO-03095647 A2 | 11/2003 |
| WO | WO-2004027019 A2 | 4/2004 |
| WO | WO-2006021724 A2 | 3/2006 |
| WO | WO-2006029319 A2 | 3/2006 |
| WO | WO-2006066066 A2 | 6/2006 |
| WO | WO-2006073052 A1 | 7/2006 |
| WO | WO-2006119137 A1 | 11/2006 |
| WO | WO-2006119432 A2 | 11/2006 |
| WO | WO-2007084773 A2 | 7/2007 |
| WO | WO-2007089632 A2 | 8/2007 |
| WO | WO-2007092563 A2 | 8/2007 |
| WO | WO-2007100465 A2 | 9/2007 |
| WO | WO-2007120542 A2 | 10/2007 |
| WO | WO-2007127264 A2 | 11/2007 |
| WO | WO-2008088895 A2 | 7/2008 |
| WO | WO-2009037279 A1 | 3/2009 |
| WO | WO-2009043936 A1 | 4/2009 |
| WO | WO-2009105612 A2 | 8/2009 |
| WO | WO-2009108274 A2 | 9/2009 |
| WO | WO-2010093784 A2 | 8/2010 |
| WO | WO-2010129021 A1 | 11/2010 |
| WO | WO-2010138263 A2 | 12/2010 |
| WO | WO-2011020118 A1 | 2/2011 |
| WO | WO-2011020710 A2 | 2/2011 |
| WO | WO-2011122950 A1 | 10/2011 |
| WO | WO-2011133890 A1 | 10/2011 |
| WO | WO-2012061744 A2 | 5/2012 |
| WO | WO-2012064960 A2 | 5/2012 |
| WO | WO-2012112578 A2 | 8/2012 |
| WO | WO-2012178173 A1 | 12/2012 |
| WO | WO-2013016315 A1 | 1/2013 |
| WO | WO-2013027223 A2 | 2/2013 |
| WO | WO-2013158879 A1 | 10/2013 |
| WO | WO-2013170078 A1 | 11/2013 |
| WO | WO-2013173512 A2 | 11/2013 |
| WO | WO-2013190059 A1 | 12/2013 |
| WO | WO-2014007858 A1 | 1/2014 |
| WO | WO-2014045674 A1 | 3/2014 |
| WO | WO-2014124282 A1 | 8/2014 |
| WO | WO-2014144229 A1 | 9/2014 |
| WO | WO-2014153083 A1 | 9/2014 |
| WO | WO-2014193716 A1 | 12/2014 |
| WO | WO-2014194132 A1 | 12/2014 |
| WO | WO-2015013313 A2 | 1/2015 |
| WO | WO-2015038958 A1 | 3/2015 |
| WO | WO-2015054653 A2 | 4/2015 |
| WO | WO-2015121501 A1 | 8/2015 |
| WO | WO-2015164757 A1 | 10/2015 |
| WO | WO-2015168666 A2 | 11/2015 |

(56) References Cited

FOREIGN PATENT DOCUMENTS

| | | |
|---|---|---|
| WO | WO-2015181823 A1 | 12/2015 |
| WO | WO-2015191508 A1 | 12/2015 |
| WO | WO-2016054557 A1 | 4/2016 |
| WO | WO-2016065001 A1 | 4/2016 |
| WO | WO-2016081811 A1 | 5/2016 |
| WO | WO-2016115382 A1 | 7/2016 |
| WO | WO-2016115503 A1 | 7/2016 |
| WO | WO-2016128558 A1 | 8/2016 |
| WO | WO-2016128559 A1 | 8/2016 |
| WO | WO-2016134338 A1 | 8/2016 |
| WO | WO-2016150964 A1 | 9/2016 |
| WO | WO-2016164642 A1 | 10/2016 |
| WO | WO-2016172008 A1 | 10/2016 |
| WO | WO-2016172155 A1 | 10/2016 |
| WO | WO-2016179644 A1 | 11/2016 |
| WO | WO-2017015102 A1 | 1/2017 |
| WO | WO-2017058892 A2 | 4/2017 |
| WO | WO-2017066764 A2 | 4/2017 |
| WO | WO-2017070516 A1 | 4/2017 |
| WO | WO-2017077451 A1 | 5/2017 |
| WO | WO-2017096164 A1 | 6/2017 |
| WO | WO-2017106236 A1 | 6/2017 |
| WO | WO-2017139643 A1 | 8/2017 |
| WO | WO-2017143100 A1 | 8/2017 |
| WO | WO-2017147123 A1 | 8/2017 |
| WO | WO-2017180854 A1 | 10/2017 |
| WO | WO-2017192750 A1 | 11/2017 |
| WO | WO-2017201248 A1 | 11/2017 |
| WO | WO-2018022608 A2 | 2/2018 |
| WO | WO-2018035213 A1 | 2/2018 |
| WO | WO-2018049226 A1 | 3/2018 |
| WO | WO-2018064624 A1 | 4/2018 |
| WO | WO-2018075798 A1 | 4/2018 |
| WO | WO-2018119330 A2 | 6/2018 |
| WO | WO-2018152333 A1 | 8/2018 |
| WO | WO-2018160582 A1 | 9/2018 |
| WO | WO-2018170310 A1 | 9/2018 |
| WO | WO-2018204764 A1 | 11/2018 |
| WO | WO-2018209154 A1 | 11/2018 |
| WO | WO-2018226785 A1 | 12/2018 |
| WO | WO-2018237066 A1 | 12/2018 |
| WO | WO-2019006418 A2 | 1/2019 |
| WO | WO-2019025984 A1 | 2/2019 |
| WO | WO-2019141765 A1 | 7/2019 |
| WO | WO-2019168961 A1 | 9/2019 |
| WO | WO-2019169004 A1 | 9/2019 |
| WO | WO-2019169132 A1 | 9/2019 |
| WO | WO-2019173434 A1 | 9/2019 |
| WO | WO-2019173538 A1 | 9/2019 |
| WO | WO-2019178412 A1 | 9/2019 |
| WO | WO-2019195423 A1 | 10/2019 |
| WO | WO-2019195444 A1 | 10/2019 |
| WO | WO-2019195449 A1 | 10/2019 |
| WO | WO-2019222444 A2 | 11/2019 |
| WO | WO-2020016318 A1 | 1/2020 |
| WO | WO-2020106916 A1 | 5/2020 |
| WO | WO-2020142653 A1 | 7/2020 |
| WO | WO-2020191300 A1 | 9/2020 |
| WO | WO-2020232297 A1 | 11/2020 |
| WO | WO-2021076911 A1 | 4/2021 |
| WO | WO-2021076925 A1 | 4/2021 |

OTHER PUBLICATIONS

Azzoni et al (The impact of polyadenylation signals on plasmid nuclease-resistance and transgene expression. Journal of Gene Medicine, vol. 9, Apr. 2007). (Year: 2007).*
ACS on STN, BD Registry, 1182714-10-8 [online] [retrieved on Apr. 30, 2019], 2009215879, Aug. 27, 2009, SEQ ID No. 7, 1 page.
ACS on STN, BD Registry, 1182714-97-1 [online] [retrieved on Apr. 30, 2019], 2009215879, Aug. 27, 2009, SEQ ID No. 210, 1 page.
Adachi et al., "Drawing a high-resolution functional map of adeno-associated virus capsid by massively parallel sequencing," Nature Communications 5(1): 14 pages (2013).
Agbandje et al. "The Structure of Human Parvovirus B19 at 8 A; Resolution" Virology 203(1):106-115 (1994).
Agbandje-McKenna et al. "AAV Capsid Structure and Cell Interactions" Methods in Molecular Biology, 807:47-92 (2011).
Albright et al., "Mapping the Structural Determinants Required for AAVrh.10 Transport across the Blood-Brain Barrier," Molecular Therapy 26(2), p. 1-14 (2017).
Albright, "Modulation of Sialic Acid Dependence Influences the Central Nervous System Transduction Profile of Adeno-associated Viruses," Journal of Virology 93(11), pp. 1-15 (2019).
Altschul et al. "Basic Local Alignment Search Tool" Journal of Molecular Biology 215:403-410 (1990).
Altschul et al., "Gapped BLAST and PSI-BLAST: a new generation of protein database search programs," Nucleic Acids Res. (1997) 25(17):3389-3402.
Altschul et al. "Local Alignment Statistics" Methods in Enzymology 266:460-480 (1996).
Altschul, SF et al., 'Issues in searching molecular sequence databases,' Nat. Genet., vol. 6, pp. 119-129, (Feb. 1994).
Andino et al. "AAV-mediated knockdown of phospholamban leads to improved contractility and calcium handling in cardiomyocytes" The Journal of Gene Medicine 10:132-142 (2008).
Arnold et al., "A calcium responsive element that regulates expression of two calcium binding proteins in Purkinje cells," Proc Natl Acad Sci USA 94(16):8842-8847 (1997).
Arruda et al., "Regional intravascular delivery of AAV-2-F.IX to skeletal muscle achieves long-term correction of hemophilia B in a large animal model," Blood 105:3458-3464 (2005).
Askoan et al. "Adeno-Associated Virus Type 2 Contains an Integrin a5 1 Binding Domain Essential for Viral Cell Entry" Journal of Virology, 80(18):8961-8969 (2006).
Asokan, et al., "Reengineering a receptor footprint of adeno-associated virus enables selective and systemic gene transfer to muscle", Nat Biotechnol, (Jan. 2010); 28(1): 79-82.
Asuri et al., Directed Evolution of adeno-associated Virus for Enhanced Gene Delivery and Gene Targeting in Human Pluripotent Stem Cells, Molecular Therapy, Nature Publishing Group GB 20(2):329-338 (2013).
Ballabh et al. "The blood-brain barrier: an overview: structure, regulation, and clinical implications" Neurobiology of Disease, 16:1-13 (2004).
Bantel-Schaal et al., "Adeno-associated virus type 5 exploits two different entry pathways in human embryo fibroblast," J Virology 73:939 (1999).
Bantel-Schaal et al. "Human adeno-Associated Virus Type 5 Is Only Distantly Related to Other Known Primate Helper-Dependent Parvovirus" Journal of Virology 73(2):939-947 (1999).
Bartlett, JS et al., 'Selective and Rapid Uptake of Adeno-Associated Virus Type 2 in Brain,' Hum. Gene Ther., 9(8):1181-1186, (May 1998).
Bell et al. "Identification of the Galactose Binding Domain of the Adeno-Associated Virus Serotype 9 Capsid" Journal of Virology, 86(13):7326-7333 (2012).
Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).
Bordoli et al. "Protein structure homology modeling using SWISS-MODEL workspace" Nature Protocols, 4(1):1-13 (2008).
Bowie, et al., "Deciphering the Message in Protein Sequences: Tolerance to Amino Acid Substitutions." Science (1990); 247: 1306-1310.
Bowles et al. "Phase 1 Gene Therapy for Duchenne Muscular Dystrophy Using a Translational Optimized AAV Vector" Molecular Therapy, 20(2):443-455 (2012).
Brichard et al. "The Tyrosinase Gene Codes for an Antigen Recognized by Autologous Cytolytic T Lymphocytes on HLA-AZ Melanomas" Journal of Experimental Medicine178:489-495 (1993).

(56) References Cited

OTHER PUBLICATIONS

Brown et al. "Chimeric Parvovirus 19 Capsids for the Presentation of Foreign Epitopes" Virology 198(2):477-488 (1994).
Brown et al. "Erythrocyte P Antigen: Cellular Receptor for B19 Parvovirus" Science 262(5130):114-117 (1993).
Carrillo-Tripp et al. "VIPERdb2: an enhanced and web API enabled relational database for structural virology" Nucleic Acids Research, 37:D436-D442 (2009).
Carstea, ED et al. 'Niemann-Pick C1 Disease Gene: Homology to Mediators of Cholesterol Homeostasis,' Science, 277(5323): 228-231 (Jul. 1997).
Cearley, C.N. et al. (2008). "Expanded repertoire of AAV vector serotypes mediate unique patterns of transduction in mouse brain," Mol. Ther. 16:1710-1718.
Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).
Chandler et al., "Systemic AAV9 gene therapy improves the lifespan of mice with Niemann-Pick disease, type C1," Human Molecular Genetics 26(1):52-64 (2017).
Chao et al. "Several Log Increase in Therapeutic Transgene Delivery by Distinct Adeno-Associated Viral Serotype Vectors" Molecular Therapy 2(6):619-623 (2000).
Chapman et al. "Structure, Sequence, and Function Correlations among Parvoviruses" Virology 194(2):491-508 (1993).
Chen et al. "Efficient Transduction of Vascular Endothelial Cells with Recombinant Adeno-Associated Virus Serotype 1 and 5 Vectors" Human Gene Therapy, 16(2):235-247 (2005).
Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).
Chiorini et al. "Cloning and Characterization of adeno-Associated Virus Type 5" Journal of Virology 73(2):1309-1319 (1999).
Chiorini et al. "Cloning of adeno-Associated Virus Type 4 (AAV4). and Generation of Recombinant AAV4 Particles" Journal of Virology 71(9):6823-6833 (1997).
Chipman et al. "Cryo-electron microscopy studies of empty capsids of human parvovirus 819 complexed with its cellular receptor" Proceedings of the National Academy of Sciences 93:7502-7506 (1996).
Chirmule et al., "Humoral immunity to adeno-associated virus type 2 vectors following administration to murine and nonhuman primate muscle," Journal of Virology, The American Society for Microbiology, , 74(5):2420-2425 (2000).
Choi et al., "Optimization of AAV expression cassettes to improve packaging capacity and transgene expression in neurons," Molecular Brain, Biomed Central Ltd, London UK, 7(1):17 pp. 1-10 (2014).
Clark, KR et al., 'Highly Purified Recombinant Adeno-Associated Virus Vectors Are Biologically Active and Free of Detectable Helper and Wild-Type Viruses,' Hum. Gene Ther., 10(6):1031-1039, (Apr. 1999).
Cleves, Ann E. "Protein transport: The nonclassical ins and outs" Current Biology7:R318-R320 (1997).
Conway et al. "High-titer recombinant adeno-associated virus production utilizing a recombinant herpes simplex virus type 1 vector expressing AAV-2 Rep and Cap" Gene Therapy 6:986-993 (1999).
Corpet, F et al., 'Multiple sequence alignment with hierarchical clustering,' vol. 16 No. 22, pp. 10881-10890, (Oct. 1988).
Cotmore et al.,"The Family Parvoviridae," Archives of Virology 159:1239-1247 (2014).
DataBase GenBank: ABS91093.1, Aug. 10, 2007, [online] [retrieved on Feb. 14, 2020] Retrieved from Internet: https://www.ncbi.nlm.nih.gov/protein/ABS91093.1.
DataBase GenBank: ACW56705.1, Sep. 24, 2009, [online] [retrieved on May 7, 2019] Retrieved from Internet:https://www.ncbi.nlm.nih.gov/protein/ACW56705.1?report=genbank&log$=prottop&blast_rank= 1&RID=D2CZ8TP9014, 1 page.

de Jesus et al., "Telomerase gene therapy in adult and old mice delays aging and increases longevity without increasing cancer," EMBO Mol. Med. 4(8): 691-704 (2012).
Devereux et al. "A comprehensive set of sequence analysis programs for the VAX" Nucleic Acids Research 12(1):387-395 (1984).
Deverman, BE, Cre-dependent selection yields AAV variants for widespread gene transfer to the adult brain, Nat. Biotechnol., 34(2) :204-209. doi: 10.1038/nbt.3440. PubMed PMID: 26829320 (Epub Feb. 1, 2016).
Dimattia et al. "Structural Insight into the Unique Properties of Adeno-Associated Virus Serotype 9," Journal of Virology, 86(12):6947-6958 (2012).
Dipasquale et al. "Identification of PDGFR as a receptor for MV-5 transduction" Nature Medicine, 9:1306-1312 (2003). (Abstract only).
Diprimo, et al., "Surface loop dynamics in adeno-associated virus capsid assembly", Journal of Virology (2008); vol. 82, No. 11, pp. 5178-5189.
Emsley et al. "Features and development of Coot" Acta Crystallographica Section D: Biological Crystallography, D66:486-501 (2010).
European Search Report for European Application No. EP19760157.8 dated Nov. 18, 2021, 6 pages.
Extended European Search Report corresponding to European Patent Application No. 16737901.5 (6 pages). (dated May 15, 2018).
Extended European Search Report corresponding to European Patent Application No. 20212583.7, dated May 3, 2021, 10 pages.
Extended European Search Report issued by the European Patent Office for Application No. 16852471.8, dated Jul. 29, 2019, 13 pages.
Extended European Search Report issued by the European Patent Office for Application No. 18754551, dated Jun. 4, 2021, 11 pages.
Fang et al., "Stable antibody expression at therapeutic levels using the 2A peptide," Nature Biotechnology 23:584-590 (2005).
Felsenstein, Joseph "Confidence Limits on Phylogenies: An Approach Using the Bootstrap" Evolution, 39 (4):783-791 (1985).
Ferrari et al. "New developments in the generation of Ad-free high-titer rAAV gene therapy vectors" Nature Medicine 3(11):1295-1297 (1997).
Fisher, KJ et al., 'Transduction with Recombinant Adeno-Associated Virus for Gene Therapy Is Limited by Leading-Strand Synthesis,' J. Virol., 70(1):520-532 (LFU assay) (Jan. 1996).
Foster et al., "Emerging Immunotherapies for Autoimmune Kidney Disease," Hyman Vaccines & Immunotherapeutics 15(4):876-890 (2019).
Foust et al. "Intravascular AAV9 preferentially targets neonatal neurons and adult astrocytes" Nature Biotechnology, 27(1):59-65 (2009).
Gao et al. "Adeno-associated viruses undergo substantial evolution in primates during natural infections" Proceedings of the National Academy of Sciences, 100(10):6081-6086 (2003).
Gao et al. "Clades of adeno-Associated Vires are Widely Disseminated in Human Tissues" Journal of Virology 78(12):6381-6388 (2004).
Gao et al. "Novel adeno-associated viruses from Rhesus Monkeys as Vectors for human gene therapy," Proceedings of the National Academy of Sciences 99(18):11854-11859 (2002).
Genbank Accession No. AAR26465, Bovine Adeno-Associated Virus, dated May 25, 2004, 2 pages.
Genbank Accession No. AAT46339, capsid protein [Adeno-associated virus 11], dated Nov. 30, 2004, 2 pages.
Genbank Accession No. ABI16639, VP1 [Adeno-associated virus 12, dated Feb. 20, 2008, 2 pages.
GenBank Accession No. AF028704 "Adeno-associated virus 6, complete genome," Jan. 12, 1998 [online]. (Retrieved online Feb. 21, 2019].
GenBank Accession No. AF028705 "adeno-associated Virus 3B, complete genome" NCBI (2 pages). (Jan. 12, 1998).
GenBank Accession No. AF043303 "Adeno-associated virus 2, complete genome," May 20, 2010 [online]. (Retrieved online Feb. 21, 2019].
GenBank Accession No. AF063497 "Adeno-associated virus 1, complete genome," Apr. 27, 1999 [online]. (Retrieved online Feb. 21, 2019].

(56) References Cited

OTHER PUBLICATIONS

Genbank Accession No. AF085716, Adeno-associated virus 5 DNA binding trs helicase (Rep22) and capsid protein (VP1) genes, complete cds., dated Feb. 9, 1999, 3 pages.
GenBank Accession No. AF258783.1 'Felis catus Niemann-Pick type C1 disease protein (NPC1) mRNA, complete eds' (2000).
GenBank Accession No. AF288061 "Hamster parvovirus 5' terminal hairpin gene sequence" NCBI (1 page). (Apr. 13, 2001), replaced by AH009962.
GenBank Accession No. AF513851 "Adeno-associated virus 7 nonstructural protein and capsid protein genes, complete cds," Sep. 5, 2002 [online]. (Retrieved online Feb. 21, 2019].
GenBank Accession No. AF513852 "Adeno-associated virus 8 nonstructural protein and capsid protein genes, complete cds," Sep. 5, 2002 [online]. (Retrieved online Feb. 21, 2019].
GenBank Accession No. AH009962 "Hamster parvovirus" NCBI (1 page). (Aug. 25, 2016), replaced AF288061.
GenBank Accession No. AY028223 "B19 Virus isolate patient_A. 1.1 genomic sequence" NCB/ (1 page). (Apr. 16, 2001).
GenBank Accession No. AY028226 "819 Virus isolate patient_A. 2.1 genomic sequence" NCB/ (1 page). (Apr. 16, 2001).
Genbank Accession No. AY186198, Avian adeno-associated virus ATCC VR-865, complete genome, dated Jun. 5, 2003, 3 pages.
Genbank Accession No. AY242997, Non-Human primate Adeno-associated virus isolate AAVrh.8 capsid protein (VP1) gene, complete cds, dated May 14, 2003, 2 pages.
Genbank Accession No. AY242998, Non-Human primate Adeno-associated virus isolate AAVrh.37 capsid protein (VP1) gene, complete cds, dated May 14, 2003, 2 pages.
Genbank Accession No. AY242999, Non-Human primate Adeno-associated virus isolate AAVrh.36 capsid protein (VP1) gene, complete cds, dated May 14, 2003, 2 pages.
Genbank Accession No. AY243000, Non-Human primate Adeno-associated virus isolate AAVrh.35 capsid protein (VP1) gene, complete cds, dated May 14, 2003, 2 pages.
Genbank Accession No. AY243001, Non-Human Primate Adeno-associated Virus Isolate AAVrh.34 capsid protein (VP1) gene, complete cds., dated May 14, 2003, 2 pages.
Genbank Accession No. AY243002, Non-Human Primate Adeno-associated Virus Isolate AAVrh.33 capsid protein (VP1) gene, complete cds. dated May 14, 2003, 2 pages.
Genbank Accession No. AY243003, Non-Human Primate Adeno-associated Virus Isolate AAVrh.32 capsid protein (VP1) gene, complete cds, dated May 14, 2003, 2 pages.
Genbank Accession No. AY243007, Non-Human Primate Adeno-associated Virus Isolate AAVrh.2 capsid protein (VP1) gene, complete cds, dated May 14, 2003, 2 pages.
Genbank Accession No. AY243013, Non-Human primate Adeno-associated virus isolate AAVrh.13 capsid protein (VP1) gene, complete cds, dated May 14, 2003, 2 pages.
Genbank Accession No. AY243015, Non-Human primate Adeno-associated virus isolate AAVrh.10 capsid protein (VP1) gene, complete cds dated May 14, 2003, 2 pages.
Genbank Accession No. AY243016, Non-Human primate Adeno-associated virus isolate AAVcy.6 capsid protein (VP1) gene, complete cds dated May 14, 2003, 2 pages.
Genbank Accession No. AY243017, Non-Human primate Adeno-associated virus isolate AAVcy.5 capsid protein (VP1) gene, complete cds, dated May 14, 2003, 2 pages.
Genbank Accession No. AY243018, Non-Human primate Adeno-associated virus isolate AAVcy.4 capsid protein (VP1) gene, complete cds, dated May 14, 2003, 2 pages.
Genbank Accession No. AY243019, Non-Human primate Adeno-associated virus isolate AAVcy.3 capsid protein (VP1) gene, complete cds, dated May 14, 2003, 2 pages.
Genbank Accession No. AY243020, Non-Human primate Adeno-associated virus isolate AAVcy.2 capsid protein (VP1) gene, complete cds, dated May 14, 2003, 2 pages.
Genbank Accession No. AY243021, Non-Human primate Adeno-associated virus isolate AAVch.5 capsid protein (VP1) gene, complete cds, dated May 14, 2003, 2 pages.
Genbank Accession No. AY243022, Non-Human primate Adeno-associated virus isolate AAVbb.2 capsid protein (VP1) gene, complete cds, dated May 14, 2003, 2 pages.
Genbank Accession No. AY243023, Non-Human primate Adeno-associated virus isolate AAVbb.1 capsid protein (VP1) gene, complete cds, dated May 14, 2003, 2 pages.
Genbank Accession No. AY388617, Bovine adeno-associated virus, complete genome, dated May 25, 2004, 3 pages.
Genbank Accession No. AY530553, Adeno-associated virus isolate pi.1 capsid protein VP1 (cap) gene, complete cds, dated Jun. 24, 2004, 2 pages.
Genbank Accession No. AY530554, Adeno-associated virus isolate pi.2 capsid protein VP1 (cap) gene, complete cds, dated Jun. 24, 2004, 2 pages.
Genbank Accession No. AY530555, Adeno-associated virus isolate pi.3 capsid protein VP1 (cap) gene, complete cds, dated Jun. 24, 2004, 2 pages.
Genbank Accession No. AY530556, Adeno-associated virus isolate rh.1 capsid protein VP1 (cap) gene, complete cds, dated Jun. 24, 2004, 2 pages.
Genbank Accession No. AY530557, Adeno-associated virus isolate rh.25 capsid protein VP1 (cap) gene, complete cds, dated Jun. 24, 2004, 2 pages.
Genbank Accession No. AY530558, Adeno-associated virus isolate rh.38 capsid protein VP1 (cap) gene, complete cds, dated Jun. 24, 2004, 2 pages.
Genbank Accession No. AY530559, Adeno-associated virus isolate rh.40 capsid protein VP1 (cap) gene, complete cds, dated Jun. 24, 2004, 2 pages.
Genbank Accession No. AY530560, Adeno-associated virus isolate rh.43 capsid protein VP1 (cap) gene, complete cds, dated Jun. 24, 2004, 2 pages.
Genbank Accession No. AY530561, Adeno-associated virus isolate rh.48 capsid protein VP1 (cap) gene, complete cds, dated Jun. 24, 2004, 2 pages.
Genbank Accession No. AY530562, Adeno-associated virus isolate rh.49 capsid protein VP1 (cap) gene, complete cds, dated Jun. 24, 2004, 2 pages.
Genbank Accession No. AY530563, Adeno-associated virus isolate rh.50 capsid protein VP1 (cap) gene, complete cds, dated Jun. 24, 2004, 2 pages.
Genbank Accession No. AY530564, Adeno-associated virus isolate rh.51 capsid protein VP1 (cap) gene, complete cds, dated Jun. 24, 2004, 2 pages.
Genbank Accession No. AY530565, Adeno-associated virus isolate rh.52 capsid protein VP1 (cap) gene, complete cds, dated Jun. 24, 2004, 2 pages.
Genbank Accession No. AY530566, Adeno-associated virus isolate rh.53 capsid protein VP1 (cap) gene, complete cds, dated Jun. 24, 2004, 2 pages.
Genbank Accession No. AY530567, Adeno-associated virus isolate rh.54 capsid protein VP1 (cap) gene, complete cds, dated Jun. 24, 2004, 2 pages.
Genbank Accession No. AY530568, Adeno-associated virus isolate rh.55 capsid protein VP1 (cap) gene, complete cds, dated Jun. 24, 2004, 2 pages.
Genbank Accession No. AY530569, Adeno-associated virus isolate rh.57 capsid protein VP1 (cap) gene, complete cds, dated Jun. 24, 2004, 2 pages.
Genbank Accession No. AY530570, Adeno-associated virus isolate rh.58 capsid protein VP1 (cap) gene, complete cds, dated Jun. 24, 2004, 2 pages.
Genbank Accession No. AY530572, Adeno-associated virus isolate rh.61 capsid protein VP1 (cap) gene, complete cds, dated Jun. 24, 2004, 2 pages.
Genbank Accession No. AY530573, Adeno-associated virus isolate rh.62 capsid protein VP1 (cap) gene, complete cds, dated Jun. 24, 2004, 2 pages.

(56) References Cited

OTHER PUBLICATIONS

Genbank Accession No. AY530574, Adeno-associated virus isolate rh.64 capsid protein VP1 (cap) gene, complete cds, dated Jun. 24, 2004, 2 pages.
Genbank Accession No. AY530575, Adeno-associated virus isolate hu.1 capsid protein VP1 (cap) gene, complete cds, dated Jun. 24, 2004, 2 pages.
Genbank Accession No. AY530576, Adeno-associated virus isolate hu.10 capsid protein VP1 (cap) gene, complete cds, dated Jun. 24, 2004, 2 pages.
Genbank Accession No. AY530577, Adeno-associated virus isolate hu.11 capsid protein VP1 (cap) gene, complete cds, dated Jun. 24, 2004, 2 pages.
Genbank Accession No. AY530578, Adeno-associated virus isolate hu.13 capsid protein VP1 (cap) gene, complete cds, dated Jun. 24, 2004, 2 pages.
GenBank Accession No. AY530579 "adeno-associated Virus 9 isolate hu.14 capsid protein VP1 (cap). gene, complete eds" NCBI (2 pages). (Jun. 24, 2004).
Genbank Accession No. AY530580, Adeno-associated virus isolate hu.15 capsid protein VP1 (cap) gene, complete cds, dated Jun. 24, 2004, 2 pages.
Genbank Accession No. AY530581, Adeno-associated virus isolate hu.16 capsid protein VP1 (cap) gene, complete cds, dated Jun. 24, 2004, 2 pages.
Genbank Accession No. AY530582, Adeno-associated virus isolate hu.17 capsid protein VP1 (cap) gene, complete cds, dated Jun. 24, 2004, 2 pages.
Genbank Accession No. AY530583, Adeno-associated virus isolate hu.18 capsid protein VP1 (cap) gene, complete cds, dated Jun. 24, 2004, 2 pages.
Genbank Accession No. AY530584, Adeno-associated virus isolate hu.19 capsid protein VP1 (cap) gene, complete cds, dated Jun. 24, 2004, 2 pages.
Genbank Accession No. AY530585, Adeno-associated virus isolate hu.2 capsid protein VP1 (cap) gene, complete cds, dated Jun. 24, 2004, 2 pages.
Genbank Accession No. AY530586, Adeno-associated virus isolate hu.20 capsid protein VP1 (cap) gene, complete cds, dated Jun. 24, 2004, 2 pages.
Genbank Accession No. AY530587, Adeno-associated virus isolate hu.21 capsid protein VP1 (cap) gene, complete cds, dated Jun. 24, 2004, 2 pages.
Genbank Accession No. AY530588, Adeno-associated virus isolate hu.22 capsid protein VP1 (cap) gene, complete cds, dated Jun. 24, 2004, 2 pages.
Genbank Accession No. AY530589, Adeno-associated virus isolate hu.23 capsid protein VP1 (cap) gene, complete cds, dated Jun. 24, 2004, 2 pages.
Genbank Accession No. AY530590, Adeno-associated virus isolate hu.24 capsid protein VP1 (cap) gene, complete cds, dated Jun. 24, 2004, 2 pages.
Genbank Accession No. AY530591, Adeno-associated virus isolate hu.25 capsid protein VP1 (cap) gene, complete cds, dated Jun. 24, 2004, 2 pages.
Genbank Accession No. AY530592, Adeno-associated virus isolate hu.27 capsid protein VP1 (cap) gene, complete cds, dated Jun. 24, 2004, 2 pages.
Genbank Accession No. AY530593, Adeno-associated virus isolate hu.28 capsid protein VP1 (cap) gene, complete cds, dated Jun. 24, 2004, 2 pages.
Genbank Accession No. AY530594, Adeno-associated virus isolate hu.29 capsid protein VP1 (cap) gene, complete cds, dated Jun. 24, 2004, 2 pages.
Genbank Accession No. AY530595, Adeno-associated virus isolate hu.3 capsid protein VP1 (cap) gene, complete cds, dated Jun. 24, 2004, 2 pages.
Genbank Accession No. AY530596, Adeno-associated virus isolate hu.31 capsid protein VP1 (cap) gene, complete cds, dated Jun. 24, 2004, 2 pages.
Genbank Accession No. AY530597, Adeno-associated virus isolate hu.32 capsid protein VP1 (cap) gene, complete cds, dated Jun. 24, 2004, 2 pages.
Genbank Accession No. AY530598, Adeno-associated virus isolate hu.34 capsid protein VP1 (cap) gene, complete cds, dated Jun. 24, 2004, 2 pages.
Genbank Accession No. AY530599, Adeno-associated virus isolate hu.35 capsid protein VP1 (cap) gene, complete cds, dated Jun. 24, 2004, 2 pages.
Genbank Accession No. AY530600, Adeno-associated virus isolate hu.37 capsid protein VP1 (cap) gene, complete cds, dated Jun. 24, 2004, 2 pages.
Genbank Accession No. AY530601, Adeno-associated virus isolate hu.39 capsid protein VP1 (cap) gene, complete cds, dated Jun. 24, 2004, 2 pages.
Genbank Accession No. AY530602, Adeno-associated virus isolate hu.4 capsid protein VP1 (cap) gene, complete cds, dated Jun. 24, 2004, 2 pages.
Genbank Accession No. AY530603, Adeno-associated virus isolate hu.40 capsid protein VP1 (cap) gene, complete cds, dated Jun. 24, 2004, 2 pages.
Genbank Accession No. AY530604, Adeno-associated virus isolate hu.41 capsid protein VP1 (cap) gene, complete cds, dated Jun. 24, 2004, 2 pages.
Genbank Accession No. AY530605, Adeno-associated virus isolate hu.42 capsid protein VP1 (cap) gene, complete cds, dated Jun. 24, 2004, 2 pages.
Genbank Accession No. AY530606, Adeno-associated virus isolate hu.43 capsid protein VP1 (cap) gene, complete cds, dated Jun. 24, 2004, 2 pages.
Genbank Accession No. AY530607, Adeno-associated virus isolate hu.44 capsid protein VP1 (cap) gene, complete cds, dated Jun. 24, 2004, 2 pages.
Genbank Accession No. AY530608, Adeno-associated virus isolate hu.45 capsid protein VP1 (cap) gene, complete cds, dated Jun. 24, 2004, 2 pages.
Genbank Accession No. AY530609, Adeno-associated virus isolate hu.46 capsid protein VP1 (cap) gene, complete cds, dated Jun. 24, 2004, 2 pages.
Genbank Accession No. AY530610, Adeno-associated virus isolate hu.47 capsid protein VP1 (cap) gene, complete cds, dated Jun. 24, 2004, 2 pages.
Genbank Accession No. AY530611, Adeno-associated virus isolate hu.48 capsid protein VP1 (cap) gene, complete cds, dated Jun. 24, 2004, 4 pages.
Genbank Accession No. AY530612, Adeno-associated virus isolate hu.49 capsid protein VP1 (cap) gene, complete cds, dated Jun. 24, 2004, 2 pages.
Genbank Accession No. AY530613, Adeno-associated virus isolate hu.51 capsid protein VP1 (cap) gene, complete cds, dated Jun. 24, 2004, 2 pages.
Genbank Accession No. AY530614, Adeno-associated virus isolate hu.52 capsid protein VP1 (cap) gene, complete cds, dated Jun. 24, 2004, 2 pages.
Genbank Accession No. AY530615, Adeno-associated virus isolate hu.53 capsid protein VP1 (cap) gene, complete cds, dated Jun. 24, 2004, 2 pages.
Genbank Accession No. AY530616, Adeno-associated virus isolate hu.54 capsid protein VP1 (cap) gene, complete cds, dated Jun. 24, 2004, 2 pages.
Genbank Accession No. AY530617, Adeno-associated virus isolate hu.55 capsid protein VP1 (cap) gene, complete cds, dated Jun. 24, 2004, 2 pages.
Genbank Accession No. AY530618, Adeno-associated virus isolate hu.56 capsid protein VP1 (cap) gene, complete cds, dated Jun. 24, 2004, 2 pages.
Genbank Accession No. AY530619, Adeno-associated virus isolate hu.57 capsid protein VP1 (cap) gene, complete cds, dated Jun. 24, 2004, 2 pages.
Genbank Accession No. AY530620, Adeno-associated virus isolate hu.58 capsid protein VP1 (cap) gene, complete cds, dated Jun. 24, 2004, 2 pages.

(56) References Cited

OTHER PUBLICATIONS

Genbank Accession No. AY530621, Adeno-associated virus isolate hu.6 capsid protein VP1 (cap) gene, complete cds, dated Jun. 24, 2004, 2 pages.
Genbank Accession No. AY530622, Adeno-associated virus isolate hu.60 capsid protein VP1 (cap) gene, complete cds, dated Jun. 24, 2004, 2 pages.
Genbank Accession No. AY530623, Adeno-associated virus isolate hu.61 capsid protein VP1 (cap) gene, complete cds, dated Jun. 24, 2004, 2 pages.
Genbank Accession No. AY530624, Adeno-associated virus isolate hu.63 capsid protein VP1 (cap) gene, complete cds, dated Jun. 24, 2004, 2 pages.
Genbank Accession No. AY530625, Adeno-associated virus isolate hu.64 capsid protein VP1 (cap) gene, complete cds, dated Jun. 24, 2004, 2 pages.
Genbank Accession No. AY530626, Adeno-associated virus isolate hu.66 capsid protein VP1 (cap) gene, complete cds, dated Jun. 24, 2004, 2 pages.
Genbank Accession No. AY530627, Adeno-associated virus isolate hu.67 capsid protein VP1 (cap) gene, complete cds, dated Jun. 24, 2004, 2 pages.
Genbank Accession No. AY530628, Adeno-associated virus isolate hu.7 capsid protein VP1 (cap) gene, complete cds, dated Jun. 24, 2004, 2 pages.
Genbank Accession No. AY530629, Adeno-associated virus isolate hu.9 capsid protein VP1 (cap) gene, complete cds, dated Jun. 24, 2004, 2 pages.
Genbank Accession No. AY629583, Avian adeno-associated virus strain DA-1, complete genome, dated Sep. 10, 2004, 3 pages.
Genbank Accession No. AY631966, Adeno-associated virus 11 nonstructural protein and capsid protein genes, complete cds, dated Nov. 30, 2004, 3 pages.
Genbank Accession No. AY695370, Adeno-associated virus isolate hu.T17 capsid protein VP1 (cap) gene, complete cds, dated Nov. 15, 2005, 3 pages.
Genbank Accession No. AY695371, Adeno-associated virus isolate hu.T32 Rep 78 protein and capsid protein VP1 (cap) genes, complete cds, dated Nov. 15, 2005, 3 pages.
Genbank Accession No. AY695372, Adeno-associated virus isolate hu.T40 Rep 78 protein and capsid protein VP1 (cap) genes, complete cds, dated Nov. 15, 2005, 3 pages.
Genbank Accession No. AY695373, Adeno-associated virus isolate hu.T70 Rep 78 protein and capsid protein VP1 (cap) genes, complete cds, dated Nov. 15, 2005, 3 pages.
Genbank Accession No. AY695374, Adeno-associated virus isolate hu.T32 Rep 71 protein and capsid protein VP1 (cap) genes, complete cds, dated Nov. 15, 2005, 3 pages.
Genbank Accession No. AY695375, Adeno-associated virus isolate hu.T88 Rep 78 protein and capsid protein VP1 (cap) genes, complete cds, dated Nov. 15, 2005, 3 pages.
Genbank Accession No. AY695376, Adeno-associated virus isolate hu.S17 Rep 78 protein and capsid protein VP1 (cap) genes, complete cds, dated Nov. 15, 2005, 3 pages.
Genbank Accession No. AY695377, Adeno-associated virus isolate hu.LG15 capsid protein VP1 (cap) gene, complete cds, dated Nov. 15, 2005, 3 pages.
Genbank Accession No. AY695378, Adeno-associated virus isolate hu.T41 capsid protein VP1 (cap) gene, complete cds, dated Nov. 15, 2005, 2 pages.
Genbank Accession No. BC045895 'Dania rerio Niemann-Pick disease, type C2, mRNA (cDNA clone MGC:56070 IMAGE:5409780), complete eds' (2003).
Genbank Accession No. BC054539 'Mus musculus Niemann Pick type C1, mRNA (cDNA clone MGC:62352 IMAGE:6405214), complete eds' (2006).
GenBank Accession No. BC090541 'Dania rerio Niemann-Pick disease, type C1, mRNA (cDNA clone IMAGE:7149020), partial eds' (2016).
GenBank Accession No. BC102504 'Bos taurus Niemann-Pick disease, type C2, mRNA (cDNA clone MGC:127986 IMAGE:7954223), complete eds' (2007).
GenBank Accession No. BC117178 '*Homo sapiens* NPC1 (Niemann-Pick disease, type C1, gene)-like 1, mRNA (cDNA clone MGC:150787 IMAGE:40125729), complete eds' (2006).
GenBank Accession No. BC143756 '*Homo sapiens* NPC1 (Niemann-Pick disease, type C1, gene)-like 1, mRNA (cDNA clone MGC:177287 IMAGE:9052270), complete eds' (2009).
GenBank Accession No. BC151276 'Bos taurus Niemann-Pick disease, type C1, mRNA (cDNA clone MGC:152602 IMAGE:8433293), complete eds' (2007).
Genbank Accession No. DQ813647, Adeno-Associated Virus 12 Rep 78 and VP1 genes, complete cds., dated Feb. 20, 2008, 3 pages.
GenBank Accession No. J00306 "Human somatostatin I gene and flanks" NCBJ (2 pages). (Jan. 13, 1995).
GenBank Accession No. J01901 "adeno-associated Virus 2, complete genome" NCBJ (3 pages). (Apr. 27, 1993).
GenBank Accession No. J02275 "Minute Virus of mice, complete genome" NCBJ (4 pages). (May 22, 1995).
GenBank Accession No. KJ893081 'Synthetic construct Homo sapiens clone ccsb BroadEn_02475 NPC2 qene, encodes complete protein' (2015).
Genbank Accession No. MI332400.1, Sequence 20 from patent U.S. Pat. No. 9,839,696, dated Feb. 12, 2018, 2 pages.
Genbank Accession No. MI332401.1, Sequence 21 from patent U.S. Pat. No. 9,839,696, dated Feb. 12, 2018, 2 pages.
Genbank Accession No. MI332402.1, Sequence 22 from patent U.S. Pat. No. 9,839,696, dated Feb. 12, 2018, 2 pages.
Genbank Accession No. MI332403.1, Sequence 23 from patent U.S. Pat. No. 9,839,696, dated Feb. 12, 2018, 2 pages.
Genbank Accession No. MI332404.1, Sequence 24 from patent U.S. Pat. No. 9,839,696, dated Feb. 12, 2018, 2 pages.
Genbank Accession No. MI332405.1, Sequence 25 from patent U.S. Pat. No. 9,839,696, dated Feb. 12, 2018, 2 pages.
Genbank Accession No. MI332406.1, Sequence 26 from patent U.S. Pat. No. 9,839,696, dated Feb. 12, 2018, 2 pages.
Genbank Accession No. MI332407.1, Sequence 27 from patent U.S. Pat. No. 9,839,696, dated Feb. 12, 2018, 2 pages.
Genbank Accession No. MI332408.1, Sequence 28 from patent U.S. Pat. No. 9,839,696, dated Feb. 12, 2018, 2 pages.
Genbank Accession No. MI332409.1, Sequence 29 from patent U.S. Pat. No. 9,839,696, dated Feb. 12, 2018, 2 pages.
Genbank Accession No. MI332410.1, Sequence 30 from patent U.S. Pat. No. 99,839,696, dated Feb. 12, 2018, 2 pages.
Genbank Accession No. MI332411.1, Sequence 31 from patent U.S. Pat. No. 9,839,696, dated Feb. 12, 2018, 2 pages.
Genbank Accession No. MI332412.1, Sequence 32 from patent U.S. Pat. No. 9,839,696, dated Feb. 12, 2018, 2 pages.
Genbank Accession No. MI332413.1, Sequence 33 from patent U.S. Pat. No. 9,839,696, dated Feb. 12, 2018, 2 pages.
Genbank Accession No. MI332414.1, Sequence 34 from patent U.S. Pat. No. 9,839,696, dated Feb. 12, 2018, 2 pages.
Genbank Accession No. MI332415.1, Sequence 35 from patent U.S. Pat. No. 9,839,696, dated Feb. 12, 2018, 2 pages.
GenBank Accession No. NC_000883 "Human parvovirus 819, complete genome" NCBI (4 pages). (Feb. 10, 2015).
GenBank Accession No. NC_001358 "Parvovirus H1, complete genome" NCBI (3 pages). (Feb. 10, 2015).
GenBank Accession No. NC_001401 "adeno-associated Virus—2, complete genome" NCBI (5 pages). (Dec. 2, 2014).
GenBank Accession No. NC_001510 "Minute Virus of mice, complete genome" NCBI (5 pages). (Mar. 28, 2016).
GenBank Accession No. NC_001701 "Goose parvovirus, complete genome" NCBI (4 pages). (Jan. 28, 2010).
GenBank Accession No. NC_001729 "adeno-associated virus—3, complete genome" NCBI (3 pages). (Jun. 28, 2010).
Genbank Accession No. NC_001729, Adeno-associated virus'3, complete genome, dated Aug. 13, 2018, 3 pages.
Genbank Accession No. NC_001829, Adeno-associated virus'4, complete genome, dated Aug. 13, 2018, 3 pages.
GenBank Accession No. NC_001829 "adeno-associated Virus—4, complete genome" NCBI (3 pages). (Jan. 28, 2010).

(56) References Cited

OTHER PUBLICATIONS

GenBank Accession No. NC_001862 "adeno-associated Virus 6, complete genome" NCBJ (3 pages). (Jan. 12, 2004).
GenBank Accession No. NC_001863 "adeno-associated Virus 38, complete genome" NCB/ (3 pages). (Jan. 12, 2014).
Genbank Accession No. NC_001863, Adeno-associated virus 3B, complete genome, dated Jan. 12, 2004, 4 pages.
GenBank Accession No. NC_002077 "adeno-associated Virus—1, complete genome" NCBI (3 pages). (Mar. 11, 2010).
Genbank Accession No. NC_004828, Avian adeno-associated virus ATCC VR-865, complete genome, dated Aug. 13, 2018, 3 pages.
Genbank Accession No. NC_005889, Bovine adeno-associated virus, complete genome, dated Aug. 13, 2018, 3 pages.
Genbank Accession No. NC_006148.1, Snake parvovirus 1, complete genome, dated Aug. 13, 2018, 3 pages.
GenBank Accession No. NC_006152 "adeno-associated Virus 5, complete genome" NCBI (3 pages). (Dec. 8, 2008).
GenBank Accession No ;: NC_006261 "adeno-associated Virus—8, complete genome" NCBI (3 pages). (Mar. 11, 2010).
Genbank Accession No. NC_006263, Avian adeno-associated virus strain DA-1, complete genome, dated Aug. 13, 2018, 3 pages.
GenBank Accession No. NM 000271.4 'Homo sapiens cholesterol transporter 1 (NPC1), mRNA' (2017).
GenBank Accession No. NM 008720.2 'Mus musculus cholesterol transporter 1 (Npc1), mRNA' (2017).
GenBank Accession No. NM 023409.4 'Mus musculus NPC intracellular cholesterol transporter 2 (Npc2 mRNA' (2017).
GenBank Accession No. NM 173918 'Bos taurus NPC intracellular cholesterol transporter 2 (NPC2), mRNA -;-(2017).
GenBank Accession No. NM_006432.3 'Homo sapiens NPC intracellular cholesterol transporter 2 (NPC2), mRNA' (2017).
GenBank Accession No. NM_214206 "Sus scrofa NPC intracellular cholesterol transporter 2 (NPC2), mRNA," dated Jun. 20, 2021, 2 pages.
GenBank Accession No. NP_044927 "capsid [Adeno-associated Virus—4]" NCBI (2 pages). (Jan. 28, 2010).
GenBank Accession No. P01166 "Somatostatin precursor [Contains-:Somatostatin 28; Somatostatin-14]" NCBI (2 pages). (Sep. 15, 2003).
GenBank Accession No. P61278 "Somatostatin precursor [Contains: Somatostatin 28; Somatostatin-14]" NCBI (2 pages). (Nov. 13, 2019).
GenBank Accession No. U89790 "Adeno-associated virus 4, complete genome," Aug. 21, 1997 [online]. (Retrieved online Feb. 21, 2019].
GenBank Accession No. X01457 "Parvovirus h-1, complete genome" NCBI (3 pages). (Apr. 18, 2005).
Genbank Accession No. Y18065, adeno-associated virus type 5 partial genome (cap and rep genes complete), dated Jan. 15, 1999, 3 pages.
Genbank Accession No. NC_001401, Adeno-associated virus—2, complete genome, dated Aug. 13, 2018, 6 pages.
Genbank Accession No. NC_002077, Adeno-associated virus—1, dated Aug. 13, 2018, 3 pages.
GenBank Accession No. BC002532 'Homo sapiens Niemann-Pick disease, type C2, mRNA (cDNA clone MGC:1333 IMAGE:3140870), complete eds' (2006).
GenBank Accession No. NC_001540 "Bovine parvovirus complete genome" NCBI (4 pages). (Nov. 30, 2009).
Gonzales, "Cross-Species Evolution of Synthetic AAV Strains for clinical Translation," ASGCT, 23 pages. (2020).
Gorman et al. "Stable alteration of pre-mRNA splicing patterns by modified U7 small nuclear RNAs" Proceedings of the National Academy of Sciences 95:4929:4934 (1998).
Govindasamy et al., "Structural Insights into Adeno-Associated Virus Serotype 5," J. Virology 87: 11187-11199 (2013).
Govindasamy et al., "Structurally mapping the diverse phenotype of adeno-associated virus serotype 4," J. Virol 80:11556-11570 (2006).

Gray et al. "Preclinical Differences of Intravascular MV9 Delivery to Neurons and Glia: A Comparative Study of Adult Mice and Nonhuman Primates" Molecular Therapy, 19(6):1058-1069 (2011).
Gregorevic et al. "Systemic Microdystrophin Gene Delivery Improves Skeletal Muscle Structure and Function in Old Dystrophic mdx Mice" Molecular Therapy 16(4):657-664 (2008).
Grieger, et al., "Separate Basic Region Motifs within the Adeno-Associated Virus Capsid Proteins Are Essential for infectivity and Assembly." J. Virol. (2006), 80(11): 5199-5210.
Grifman, et al., "Incorporation of tumor-targeting peptides into recombinant adeno-associated virus capsids". Molecular Therapy (2001); vol. 3, No. 6, pp. 964-975.
Grimm D., et al., "In Vitro and in Vivo Gene Therapy Vector Evolution Via Multispecies Interbreeding and Retargeting of Adeno-Associated Viruses," Journal of Virology, Jun. 2008, vol. 82(12), pp. 5887-5911, XP002610286.
Gurda et al. "Capsid Antibodies to Different adeno-Associated Virus Serotypes Bind Common Regions" Journal of Virology, 87(16):9111-9124 (2013).
Gurda et al., "Mapping a Neutralizing Epitope onto the Capsid of Adeno-Associated Virus Serotype 8," Journal of Virology 86(15): 7739-7751 (2012).
Hadaczek et al. "Transduction of Nonhuman Primate Brain with Adeno-Associated Virus Serotype 1: Vector Trafficking and Immune Response" Human Gene Therapy, 20(3):225-237 (2009).
Hajitou et al., "Vascular targeting: recent advances and therapeutic perspectives," TCM 16:80-88 (2006).
Hauck et al. "Characterization of Tissue Tropism Determinants of Adeno-Associated Virus Type 1" Journal of Virology 77(4):2768-2774 (2003).
Havlik, Engineering A Humanized AAV8 Capsid Through Iterative Structure-Guided Evolution ASGCT, 24 pages. (2019).
Havlik et al., "Co-Evolution of AAV Capsid Antigenicity and Tropism Through a Structure-Guided Approach," ASGCT, 39 pages (2020).
Higgins, Desmond G., and Sharp, Paul M. "CLUSTAL: a package for performing multiple sequence alignment on a microcomputer." Gene (1988); 73.1: 237-244.
Higgins, DG et al., 'Fast and sensitive multiple sequence alignments on a microcomputer,' Comput Appl Biosci., 5(2):151-3, (Apr. 1989).
Hoshijima et al. "Chronic suppression of heart-failure progression by a pseudo phosphorylated mutant of phospholamban via in vivo cardiac rAAV gene delivery" Nature Medicine 8:864-871 (2002).
Huang et al. "Characterization of the adeno-Associated Virus 1 and 6 Sialic Acid Binding Site" Journal of Virology, 9 (11):5219-5230 (2016).
Huang et al. "Parvovirus qlycan interactions" Current Opinion in Virology 7:108-118 (2014).
Huang, X et al., 'Dynamic programming algorithms for restriction map comparison,' Cabios, Vol.8, No. 5., pp. 511-520, (1992).
Hughes et al., "AAV9 intracerebroventricular gene therapy improves lifespan, locomotor function and pathology in a mouse model of Niemann-Pick type C1 disease," Human Molecular Genetics 27(17)3079-3098 (2018).
International Search Report and the Written Opinion of the International Searching Authority corresponding to International Patent Application No. PCT/2018/018381 (14 pages) (mailed Jul. 5, 2018).
International Search Report and the Written Opinion of the International Searching Authority corresponding to International Patent Application No. PCT/US2019/020053 (10 pages) (mailed Jun. 6, 2019).
International Search Report and Written Opinion issued by the International Searching Authority for Application No. PCT/2016/013460, dated May 12, 2016, 11 pages.
International Search Report and Written Opinion issued by the International Searching Authority for Application No. PCT/2016/054143, dated Mar. 23, 2017, 33 pages.
International Search Report and Written Opinion issued by the International Searching Authority for Application No. PCT/2020/023877, dated Aug. 3, 2020, 21 pages.

(56) References Cited

OTHER PUBLICATIONS

International Search Report and Written Opinion issued by the International Searching Authority for Application No. PCT/US20/15386, dated Apr. 27, 2020, 14 pages.
International Search Report and Written Opinion issued by the International Searching Authority for Application No. PCT/US2016/026524, dated Jan. 9, 2016, 10 pages.
International Search Report and Written Opinion issued by the International Searching Authority for Application No. PCT/US2018/038584 dated Aug. 24, 2018, 11 pages.
International Search Report and Written Opinion issued by the International Searching Authority for Application No. PCT/US2019/062531, dated Apr. 1, 2020, 12 pages.
International Search Report and Written Opinion issued by the International Searching Authority for Application No. PCT/US2020/032978, dated Oct. 15, 2020, 14 pages.
International Search Report and Written Opinion issued by the International Searching Authority for Application No. PCT/US2020/056015, dated Feb. 12, 2021, 17 pages.
International Search Report and Written Opinion issued by the International Searching Authority for Application No. PCT/US2020/056031, dated Feb. 15, 2021, 18 pages.
International Search Report and Written Opinion issued by the International Searching Authority for Application No. PCT/US2021/030937, dated Oct. 29, 2021, 14 pages.
International Search Report of International PCT/US2016/026524, mailed Sep. 1, 2016.
Invitation to Pay issued by the International Searching Authority for Application No. PCT/US21/30937, dated Aug. 16, 2021, 3 pages.
Invitation to Pay issued by the International Searching Authority for Application No. PCT/US2019/062531, dated Feb. 3, 2020, 2 pages.
Janson, C. et al., 'Clinical protocol. Gene therapy of Canavan disease: AAV-2 vector for neurosurgical delivery of aspartoacylase gene (ASPA) to the human brain,' Hum. Gene Ther., 13(11):1391-1412 (Jul. 2002).
Kailasan et al., "Structure of an enteric pathogen, bovine parvovirus," Virology 89:2603-2614 (2015).
Kaplitt, M.G. et al. (1994). "Long-term gene expression and phenotypic correction using adeno- associated virus vectors in the mammalian brain," Nature Genetics 6:148-154.
Karlin et al. "Applications and statistics for multiple high-scoring segments in molecular sequences" Proceedings of National Academy of Sciences 90:5873-5877 (1993).
Kashiwakura et al. "Hepatocyte Growth Factor Receptor Is a Coreceptor for Adeno-Associated Virus Type 2 Infection" Journal of Virology, 79(1).609-614 (2005).
Kauffman et al., "Mechanism Matters: A Taxonomy of Cell Penetrating Peptides," Trends in Biochemical Sciences, Elsevier, Amsterdam, NL 40(12):749-764 (2015).
Kawakami et al. "Cloning of the gene coding for a shared human melanoma antigen recognized by autologous T cells infiltrating into tumor" Proceedings of the National Academy of Sciences 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).
Koivunen et al., "Identification of Receptor Ligands with Phase Display Peptide Libraries," J. Nucl. Med. 40:883-888 (1999).
Krissinel et al. "Secondary-structure matching (SSM)., a new tool for fast protein structure alignment in three dimensions" Acta Crystallographica Section D: Biological Crystallography, D60:2256-2268 (2004).
Kumar et al. "MEGA7: Molecular Evolutionary Genetics Analysis Version 7.0 for Bigger Datasets" Molecular Biology and Evolution, 33(7):1870-1874 (2016).
Lein et al. "Genome-wide atlas of gene expression in the adult mouse brain" Nature, 445(7124):168-176 (2007). (Abstract only).

Lerch et al., "The structure of adeno-associated virus serotype 3B (AAV-3B): insights into receptor binding and immune evasion," Virology 403(1):26-36 (2010).
Levine et al. "The Tumor Suppressor Genes" Annual Review of Biochemistry 62:623-651 (1993).
Li et al. "Construction of phospholamban antisense RNA recombinant adeno-associated Virus vector and its effects in rat cardiomyocytes" Acta Pharmacologica Sinica 26(1).51-55 (2005).
Li et al. "Development of Patient-specific AAV Vectors After Neutralizing Antibody Selection for Enhanced Muscle Gene Transfer" Molecular Therapy, 24(1):53-65 (2016).
Li et al. "Engineering and Selection of Shuffled AAV Genomes: A New Strategy for Producing Targeted Biological Nanoparticles" Molecular Therapy, 16(7):1252-1260 (2008).
Li et al. "Single Amino Acid Modification of adeno-Associated Virus Capsid Changes Transduction and Humeral Immune Profiles" Journal of Virology, 86(15):7752-7759 (2012).
Lisowski L., et al., "Selection and Evaluation of Clinically Relevant AAV Variants in a Xenograft Liver Model," Nature, Feb. 2014, vol. 506 (7488), pp. 382-386, XP055573596.
Loftus, SK et al., 'Murine Model of Niemann-Pick C Disease: Mutation in a Cholesterol Homeostasis Gene,' Science, 277(5323):232-235 (Jul. 1997).
Madigan et al. "Engineering AAV receptor footprints for gene therapy" Current Opinion in Virology, 18:89-96 (2016).
Margolskee, R. F. "Epstein-Barr Virus Based Expression Vectors" Current Topics in Microbiology and Immunology 158:67-95 (1992).
Mauro et al., "A critical analysis of codon optimization in human therapeutics," Trends in Molecular Medicine, Nov. 2014, vol. 20, No. 11, pp. 604-613.
McCarty, D.M., et al., "Self-complementary recombinant adeno-associated virus (scAAV) vectors promote efficient transduction independently of DNA synthesis," Gene Therapy 8, 1248-1254 (2001).
McLaughlin et al., "Adeno-associated virus general transduction vectors: analysis of proviral structures," J. Virol., (1988) 62:1963-1973.
Miller et al. "Production, purification and preliminary X-ray crystallographic studies of adeno-associated virus serotype 1" Acta Crystallographica Section F: Structural Biology and Crystallization Communications, 62(Pt 12):1271-1274 (2006).
Mingozzi et al. "Immune responses to AAV vectors: overcoming barriers to successful gene therapy" Blood, 122 (1):23-36 (2013).
Mingozzi et al., "Overcoming the Host Immune Response to Adeno—Associated Virus Gene Delivery Vectors: The Race Between Clearance, Tolerance, Neutralization, and Escape," Annual Review of Virology 1(1):511-534 (2017).
Miyamura et al. "Parvovirus particles at platforms for protein presentation" Proceedings of National Academy of Sciences 91:8507-8511 (1995).
Mller et al. "Random peptide libraries displayed on adeno-associated virus to select for targeted gene therapy vectors", Nat Biotechnol, Sep. 2003; 21(9):1040-6. Epub Aug. 3, 2003.
Mori et al. "Two novel adeno-associated viruses from cynomolgus monkey: pseudotyping characterization of capsid protein" Virology 330:375-383 (2004).
Muramatsu et al. "Nucleotide Sequencing and Generation of an Infectio Clone of adeno-Associated Virus 3", Virology, 221(0367):208-217 (1996).
Murlidharan et al. "Polysialic Acid as a Novel Regulator of AAV Tropism in the Developing Brain" Molecular Therapy 23(Supplement 1):S106 (2015), 1 page.
Murlidharan et al. "Biology of adeno-associated viral vectors in the central nervous system" Frontiers in Molecular Neuroscience, 7(76):1-9 (2014).
Murlidharan et al. "CNS-restricted Transduction and CRISPR/Cas9-mediated Gene Deletion with an Engineered AAV Vector" Molecular Therapy: Nucleic Acids, 5:e338 (2016).
Murlidharan et al. "Glymphatic fluid transport controls paravascular clearance of MV vectors from the brain" JCI Insight, 1(14):e88034 (2016).

(56) References Cited

OTHER PUBLICATIONS

Murlidharan et al. "Unique Glycan Signatures Regulate adeno-Associated Virus Tropism in the Developing Brain" Journal of Virology 89(7):3976-3987 (2015).
Muzyczka, N. "Use of adeno-Associated Virus as a General Transduction Vector for Mammalian Cells," Current Topics in Microbiology and Immunology 158:97-129 (1992).
Nam et al. "Structure of Adeno-Associated Virus Serotype 8, a Gene Therapy Vector" Journal of Virology, 81 (22):12260-12271 (2007).
Nathwani et al. "Long-Term Safety and Efficacy of Factor IX Gene Therapy in Hemophilia B" The New England Journal of Medicine, 371(21):1994-2004 (2014).
Needleman and Wunsch, "A general method applicable to the search for similarities in the amino acid sequence of two proteins." J Mol Biol. (1970); 48(3): 443-453.
Newton & Deutscher, Phage Peptide Display in Handbook of Experimental Pharmacology, pp. 145-163, Springer-Verlag, Berlin (2008).
Ng et al. "Structural Characterization of the Dual Glycan Binding adeno-Associated Virus Serotype 6" Journal of Virology, 84(24):12945-12957 (2010).
Nguyen Vu et al., "Cerebellar Purkinje cell activity drives motor learning", Nature Neuroscience 16(12):1734-1736 (2013).
Padron et al. "Structure of adeno-Associated Virus Type 4" Journal of Virology 79(8):5047-5058 (2005).
Palombo et al. "Site-Specific Integration in Mammalian Cells Mediated by a New Hybrid Baculovirus-Adeno-Associated Virus Vector" Journal of Virology72(6):5025-5034 (1998).
Papadakis, ED et al., 'Promoters and Control Elements: Designing Expression Cassettes for Gene Therapy,' Curr. Gene Therapy, vol. 4, No. 1, pp. 89-113, (Mar. 2004).
Partial Supplementary European Search Report issued by the European Patent Office for Application No. 16852471.8, dated Apr. 24, 2019, 17 pages.
Passini, MA et al., 'Distribution of a Lysosomal Enzyme in the Adult Brain by Axonal Transport and by Cells of the Rostral Migratory Stream,' J. Neuroscience, 22(15):6437-6446 (Aug. 2002).
Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).
Pillay et al. "An essential receptor for adeno-associated virus infection" Nature, 530(7588):108-112 (2016).
Pulicherla et al. "Engineering Liver-detargeted AAV9 Vectors for Cardiac and Musculoskeletal Gene Transfer" Molecular Therapy, 19(6):1070-1078 (2011).
Puttaraju et al. "Spliceosome-mediated RNA trans-splicing as a tool for gene therapy" Nature Biotechnology 17:246-252 (1999).
Robbins et al. "Recognition of Tyrosinase by Tumor-infiltrating Lymphocytes from a Patient Responding to Immunotherapy" Cancer Research 54:3124-3126 (1994).
Rosenberg et al. "A New Era for Cancer Immunotherapy Based on the Genes that Encode Cancer Antigens" Immunity 10:281-287 (1999).
Rosenberg et al. "Comparative Efficacy and Safety of Multiple Routes of Direct CNS Administration of Adeno—Associated Virus Gene Transfer Vector Serotype rh.10 Expressing the Human Arylsulfatase A cDNA to Nonhuman Primates" Human Gene Therapy Clinical Development, 25(3):164-177 (2014).
Rosenberg "The Immunotherapy of Solid Cancers Based on Cloning the Genes Encoding Tumor-Rejection Antigens" Annual Review of Medicine 47:481-491 (1996).
Saitou, N. et al. (1987). "The neighbor-joining method: A new method for reconstructing phylogenetic trees," Mol. Biol. Evol. 4:406-425.
Salinas et al. "A hitchhiker's guide to the nervous system: the complex journey of viruses and toxins" Nature Reviews Microbiology, 8(9):645-655 (2010). (Abstract only).
Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12).1072-1082 (2013).
Shade et al. "Nucleotide Sequence and Genome Organization of Human Parvovirus B19 Isolated from the Serum of a Child during Aplastic Crisis" Journal of Virology 28(3):921-936 (1986).
Sharp et al. "RNA Interference" Science 287(5462):2431-2433 (2000).
Shen et al. "Engraftment of a Galactose Receptor Footprint onto adeno-associated Viral Capsids Improves Transduction Efficiency" The Journal of Biological Chemistry, 288(40):28814-28823 (2013).
Shen et al., Multiple Roles for Sialylated Glycans in Determining the Cardiopulmonary Tropism of Adeno-Associated Virus 4, Journal of Virology 87(24):13206-13213 (2013).
Shi et al. "Insertional Mutagenesis at Positions 520 and 584 of adeno-Associated Virus Type 2 (AAV2). Capsid Gene and Generation of AAV2 Vectors with Eliminated Heparin- Binding Ability and Introduced Novel Tropism" Human Gene Therapy 17:353-361 (2006).
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.
Smith et al, "Comparison of Biosequences", Advanced in Applied Mathematics, vol. 2, Issue 4, Dec. 1981, pp. 482-489.
Smith et al., "Structural Mapping of AAV9 Antigenic Sites and the Engineering of Immune Escape Variants," Molecular Therapy; 20th Annual Meeting of the American Society of Gene and Cell Therapy (ASGCT).; Washington, DC, A; May 10-13, 2017, Nature Publishing Group, GB vol. 25, No. 5, Suppl 1 (2017).
Smith, TF et al., 'Identification of Common Molecular Subsequences,' Journal of Molecular Biology, 147:195-197, PMID 7265238. doi: 10.1016/0022-2836(81)90087-5, (1981).
Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).
Srivastava et al. "Nucleotide Sequence and Organization of the Adeno Associated Virus 2 Genome." Journal of Virology (1983); 45:2, p. 555-564.
Summerford et al. "Membrane-Associated Heparan Sulfate Proteoglycan Is a Receptor for adeno-Associated Virus Type 2 Virions" Journal of Virology, 72(2):1438-1445 (1998).
Tellez et al. "Characterization of Naturally-Occurring Humoral Immunity to AAV in Sheep" PLoS ONE, 8(9):e75142 (2013).
Tinsley et al. "Amelioration of the dystrophic phenotype of mdx mice using a truncated utrophin transgene" Nature 384(6607):349-353 (1996).
Titeux et al., "SIN Retroviral Vectors Expressing COL7A1 Under Human Promoters for Ex Vivo Gene Therapy of Recessive Dystrophic Epidermolysis Bullosa," Mol. Ther., 2010 18:1509-1518.
Tsao et al. The Three-Dimensional Structure of Canine Parvovirus and Its Functional Implications Science 251(5000):1456-1464 (1991).
Tse et al., "Strategies to Circumvent Humoral Immunity to Adeno-Associated Viral Vectors," Expert Opinion on Biological Therapy 15(6):845-855 (2015).
Tse L.V., et al., "Structure-Guided Evolution of Antigenically Distinct Adeno-Associated Virus Variants for Immune Evasion," Proceedings of the National Academy of Sciences, Jun. 2017, vol. 114(24), pp. E4812-E4821, XP055590029.
Tseng et al. "Adeno-Associated Virus Serotype 1 (AAV1).- and AAV5-Antibody Complex Structures Reveal Evolutionary Commonalities in Parvovirus Antigenic Reactivity" Journal of Virology, 89(3):1794-1808 (2015).
Tseng et al. "Generation and characterization of anti-adeno-associated Virus serotype 8 (AAV8). and anti-AAV9 monoclonal antibodies" Journal of Virological Methods, 236:105-110 (2016).
Tseng et al. "Mapping the AAV capsid host antibody response toward the development of second generation gene delivery vectors" Frontiers in Immunology, 5(9):1-11 (2014).
UniProt Accession No. O15118, dated May 30, 2000, 21 pages.
Urabe et al. "Insect Cells as a Factory to Produce adeno-Associated Virus Type 2 Vectors" Human Gene Therapy 13:1935-1943 (2002).

(56) References Cited

OTHER PUBLICATIONS

Various: Abstracts, 20th Annual Meeting of the American-Society-of-Gene-and-Cell-Therapy (ASGCT); Washington, DC, USA; May 10-13, 2017, Molecular Therapy : The Journal of the American Society of Gene Therapy 25:1-363 (2017).
Veldwijk, MR et al., 'Development and optimization of a real-time quantitative PCR-based method for the titration of AAV-2 vector stocks,' Mal. Ther., 6(2):272-8 (Aug. 2002).
Vincent et al. "Long-term correction of mouse dystrophic degeneration by adenovirus-mediated transfer of a minidystrophin gene" Nature Genetics 5:130-134 (1993).
Walters et al. "Structure of adeno-Associated Virus Serotype 5" Journal of Virology 78(7):3361-3371 (2004).
Wang et al. "Adeno-associated Virus vector carrying human minidystrophin genes effectively ameliorates muscular dystrophy in mdx mouse model" Proceedings of the National Academy of Sciences 97(25):13714-13719 (2000).
Wang et al., "Selection of neutralizing antibody-resistant AAV8 variants with structure-guided site-specific saturated mutagenesis," Molecular Therapy, 2011, vol. 19 Suppl. 1, S129.
Wang et al. "Expanding the genetic code" Annual Review of Biophysics and Biomolecular Structure 35:225-249 (2006).
Wassif, CA et al., 'High Incidence of Unrecognized Visceral/Neurological Late onset Niemann-Pick Disease, type C1 Predicted by Analysis of Massively Parallel Sequencing Data Sets,' Genet Med., 18(1):41-48 (Jan. 2016).
Weller et al. "Epidermal growth factor receptor is a co-receptor for adeno-associated virus serotype 6" Nature Medicine, 16(6):662-664 (2010).
Williams et al. "Monocyte maturation, HIV susceptibility, and transmigration across the blood brain barrier are critical in HIV neuropathogenesis" Journal of Leukocyte Biology, 91(3):401-415 (2012).
Winkler et al., "Changing the Antigen Binding Specificity by Single Point Mutations of an Anti-p24 (HIV-1) Antibody", The Journal of Immunology, 165: 4505-4514 (2000).
Work, et al., "Vascular bed-targeted in vivo gene delivery using tropism-modified adeno-associated viruses." Mol. Ther.; vol. 13, No. 4, pp. 683-693 (Apr. 2006).
Wu et al. "alpha2,3 and alpha2,6 N-Linked Sialic Acids Facilitate Efficient Binding and Transduction by Adeno—Associated Virus Types 1 and 6" Journal of Virology, 80(18):9093-9103 (2006).
Wu et al. "Single Amino Acid Changes Can Influence Titer, Heparin Binding, and Tissue Tropism in Different adeno—Associated Virus Serotypes" Journal of Virology, 80(22):11393-11397 (2006).
Xiao et al. "Gene Therapy Vectors Based on adeno-Associated Virus Type 1" Journal of Virology 73(5):3994-4003 (1999).
Xiao et al., "Gene transfer by adeno-associated virus vectors into the central nervous system," Exp. Neurobiol., (1997) 144:113-124.
Xiao et al. "Interpretation of Electron Density with Stereographic Roadmap Projections" Journal of Structural Biology, 158(2):182-187 (2007).
Xie et al. "Canine Parvovirus Capsid Structure, Analyzed at 2.9 A Resolution" Journal of Molecular Biology 264(3):497-420 (1996).
Xie et al. "The atomic structure of adeno-associated Virus (AAV-2)., a vector for human gene therapy" Proceeding of the National Academy of Sciences 99(16):10405-10410 (2002).
Xie, J. et al., "Short DNA Hairpins Compromise Recombinant Adeno-Associated Virus Genome Homogeneity," Mol. Ther., 25(6): 1363-1374 (2017).
Yang et al. "Global CNS Transduction of Adult Mice by Intravenously Delivered rAAVrh.8 and rAAVrh.10 and Nonhuman Primates by rAAVrh.1O" Molecular Therapy, 22(7):1299-1309 (2014).
Zhang, "Endocytic mechanisms and drug discovery in neurodegenerative diseases," Frontiers in Bioscience 13:6086-6105 (2008).
Zhang et al. "Several rAAV Vectors Efficiently Cross the Blood-brain Barrier and Transduce Neurons and Astrocytes in the Neonatal Mouse Central Nervous System" Molecular Therapy, 19(8):1440-1448 (2011).
Zhang et al. "Recombinant adenovirus expressing adeno-associated Virus cap and rep proteins supports production of high-titer recombinant adeno-associated virus" Gene Therapy 8:704-712 (2001).
Zinn, E. et al., "In Silico Reconstruction of the Viral Evolutionary Lineage Yields a Potent Gene Therapy Vector," Cell Reports, Aug. 2015; 12:1056-1068.
Zolotukhin, et al., "Recombinant adeno-associated virus purification using novel methods improves infectious titer and yield." Gene Therapy (1999); vol. 6, pp. 973-985.
Extended European Search Report issued by the European Patent Office for Application No. 19887003.2, dated Jul. 12, 2022, 10 pages.
Frankei, A.E. et al. (2000). Characterization of diphtheria fusion proteins targeted to the human interleukin-3 receptor, Protein Engineering 13:575-581.
Pakula A.A., et al., "Genetic Analysis of Protein Stability and Function," Annual Review of Genetics, 1989, vol. 23, pp. 289-310.
Asokan et al., "The AVV Vector Toolkit: Poised at the Clinical Crossroads," Molecular Therapy 20(4):699-708 (2012).
Bennett et al. "AAV6 K531 serves a dual function in selective receptor and antibody ADK6 recognition" Virology, 18:369-376 (2018).
Clapcote SJ, et al., " Mutation 1810N in the alpha3 isoform of Na+, K+-ATPase causes impairments in the sodium pump and hyperexcitability in the CNS," Proc Natl Acad Sci USA. 106(33):14085-14090 (2009).
Piguet Françoise et al., "Rapid and Complete Reversal of Sensory Ataxia by Gene Therapy in a Novel Model of Friedreich Ataxia", Molecular Therapy, Nature Publishing Group, GB 26(8), pp. 1-13 (2018).
Ghusayni R, et al., "Magnetic resonance imaging volumetric analysis in patients with Alternating hemiplegia of childhood: A pilot study," Eur J Paediatr Neurol. 26:15-19 (2020).
Heinzen EL, et al., "De nova mutations in ATP1A3 cause alternating hemiplegia of childhood," Nat Genet. 44 (9):1030-1034 (2012).
Helseth AR, et al., "Novel E815K knock-in mouse model of alternating hemiplegia of childhood," Neurobiol Dis. 119:100-112 (2018).
Holm R, et al., "B. Neurological disease mutations of a3 Na+, K+-ATPase: Structural and functional perspectives and rescue of compromised function," Biochim Biophys Acta. 1857(11):1807-1828 (2016).
Hunanyan AS, et al., Knock-in mouse model of alternating hemiplegia of childhood: behavioral and electrophysiologic characterization. Epilepsia. 56(1):82-93 (2015).
Hunanyan AS, et al., "Mechanisms of increased hippocampal excitability in the Mashl+/− mouse model of Na+ /K+ -ATPase dysfunction," Epilepsia 59(7):1455-1468 (2018).
Ikeda K, et al., " Knockout of sodium pump a3 subunit gene(Atp1a3-/-) results in perinatal seizure and defective respiratory rhythm generation," Brain Res. 1666:27-37 (2017).
Isaksen TJ, et al., "Hypothermia-induced dystonia and abnormal cerebellar activity in a mouse model with a single disease-mutation in the sodium-potassium pump," PLoS Genet. 13(5):e1006763, pp. 1-23 (2017).
Kells, A.P., et al., "AAV-Mediated Gene Delivery of BDNF or GDNF is Neuroprotective in a Model of Huntington Disease," Molecular Therapy, May 2004, vol. 9(5), pp. 682-688.
Kirshenbaum GS, et al., "Alternating hemiplegia of childhood-related neural and behavioural phenotypes in Na +, K+-ATPase a3 missense mutant mice," PLoS One. 8(3):e60141, pp. 1-15 (2013).
Kuck et al. "Development of AAV serotype-specific ELISAs using novel monoclonal antibodies" Journal of Virological Methods, 140(1-2):17-24 (2007) (Abstract only).
Lux et al. "Green Fluorescent Protein-Tagged Adeno-Associated Virus Particles Allow the Study of Cytosolic and Nuclear Trafficking" Journal of Virology, 79{18):11776-11787 (2005).
Masoud M, et al., " Diagnosis and Treatment of Alternating Hemiplegia of Childhood," Curr Treat Options Neurol. 19(2):8 (2017).
McCraw et al. "structurE of adeno-associated virus-2 In Complex with Neutralizing Monoclonal antibodY A20" Virology, 431(1-2):40-49 (2012).

(56) References Cited

OTHER PUBLICATIONS

Mikati MA, et al., " Alternating hemiplegia of childhood: clinical manifestations and long-term outcome," Pediatr Neurol. 23(2):134-141 (2000).
Mori, et al., "Two novel adeno-associated viruses from cynomolgus monkey: pseudotyping characterization of capsid protein." Virology, Dec. 2004; 330: 375-383.
Piguet Françoise et al., "Rapid and Complete Reversal of Sensory Ataxia by Gene Therapy in a Novel Model of Friedreich Ataxia", Molecular Therapy, Nature Publishing Group, GB, vol. 26, No. 8, Aug. 1, 2018 (Aug. 1, 2018), pp. 1-13.
Powell et al. Characterization of a Novel Adeno-Associated Viral Vector with Preferential Oligodendrocyte Tropism. Gene Therapy, 2016. 23:807-814.
Severino, M. et al., "White matter and cerebellar involvement in alternating hemiplegia of childhood," J Neurol. 267 (5):1300-1311 (2020).
Veron et al. "Humeral and Cellular Capsid-Specific Immune Responses to Adeno-Associated Virus Type 1 in randomized Healthy Donors" The Journal of Immunology, 188:6418-6424 (2012).
Wang; Q. et al., "Identification of an adeno-associated Virus binding epitope for AVB sepharose affinity resin," Molecular Therapy—Methods & Clinical Development vol. 2, pp. 1-6 (2015).
Wobus et al. "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection," J. of Virology, 74(19):9281-9293 (2000).
Ye Q, et al., "The AAA+ ATPase TRIP13 remodels HORMA domains through N-terminal engagement and unfolding," EMBO J. 36(16):2419-2434 (2017).
Zhong et al. "Next generation of adeno-associated virus 2 vectors: Point mutations in tyrosines lead to high-efficiency transduction at lower doses" Proceedings of the National Academy of Sciences USA, 105(22):7827-7832 (2008).
Zhong et al. "Tyrosine-phosphorylation of AAV2 vectors and its consequences on viral intracellular trafficking and transgene expression" Virology, 381(2):194-202 (2008).
Zolotukhin et al. "Production and purification of serotype 1, 2, and 5 recombinant adeno-associated viral vectors" Methods, 28(2):158-167 (2002) {Abstract only).

* cited by examiner

C - mScar - bGH

C - dmScar - longUTR

C - dmScar - bGH

AD - dmScar - shortUTR

ADENO-ASSOCIATED VIRUS VECTORS FOR TREATMENT OF RETT SYNDROME

CROSS-REFERENCE TO RELATED APPLICATIONS

This application claims priority to U.S. Provisional Application No. 63/067,668, filed Aug. 19, 2020, the contents of which are incorporated herein by reference in their entirety.

FIELD

The instant disclosure relates to the fields of molecular biology and gene therapy. More specifically, disclosure relates to compositions and methods for producing recombinant viral vectors.

INCORPORATION OF THE SEQUENCE LISTING

The contents of the text file submitted electronically herewith are incorporated herein by reference in their entirety: A computer readable format copy of the Sequence Listing (STRD_020_01US_Sequence Listing.txt, date recorded: Aug. 19, 2021, file size about 89,555 bytes).

BACKGROUND

Rett Syndrome is a genetic neurological disorder manifesting at about 6 months to 18 months of age primarily in girls and women. Affecting about 1 in 8,500 females, Rett Syndrome is a rare disease. Patients with Rett Syndrome often exhibit a wide range of symptoms including language disability, reduced coordination, microcephaly, repetitive movements, seizures, scoliosis, and cognitive disability. While the life expectancy for women with Rett Syndrome is in the mid-40s, males with Rett Syndrome often die in infancy.

Rett Syndrome is caused by mutations in the mecp2 gene, and is correlated with defects in neuronal function. Many cases of Rett syndrome result from new mutations in the mecp2 gene. However, in a small number of cases, mecp2 mutations show an X-linked, dominant pattern of inheritance. Mutations in mecp2 also cause other diseases such as MECP2 duplication syndrome and PPM-X syndrome, and may be associated with Autism Spectrum disorder.

There is no known treatment for Rett Syndrome, or other mecp2-associated diseases. Rett Syndrome symptoms are typically managed using anticonvulsants, special education, physiotherapy, and braces. Gene therapy is a potentially useful method to treat Rett Syndrome. However, gene therapy targeted to the nervous system often faces several technical hurdles, including identifying the right neuronal target genes that would alleviate symptoms upon expression, promoting high levels of expression of these genes in a regulated manner, and delivering the gene therapy constructs in a targeted manner to neurons. Accordingly, there is an unmet need for compositions and methods that treat Rett Syndrome, and other mecp2-associated diseases.

SUMMARY

The disclosure provides nucleic acids comprising an adeno-associated virus (AAV) expression cassette, wherein the AAV expression cassette comprises, from 5' to 3': a 5' inverted terminal repeat (ITR); a synthetic, activity-dependent promoter; a Rett Syndrome-associated gene; and a 3' ITR. In some embodiments, the promoter drives expression of the Rett-syndrome-associated gene. In some embodiments, the promoter is a MECP2-independent promoter. In some embodiments, the promoter comprises a nucleic acid sequence derived from a promoter of a neuronal immediate early gene. In some embodiments, the neuronal immediate early gene is selected from the group consisting of the Arc gene, the c-fos gene, and the egr-1 gene. In some embodiments, the promoter comprises a minimal Arc gene promoter (ArcMin).

In some embodiments, the ArcMin is a human ArcMin (hArcMin). In some embodiments, the hArcMin comprises a nucleic acid sequence of SEQ ID NO: 12, or a sequence at least 90% identical thereto. In some embodiments, the promoter comprises a cyclic AMP response element (CRE), a serum response element (SRE), a synaptic activity response element (SARE), a MEF2 response element, or a combination thereof. In some embodiments, the promoter comprises a synaptic activity response element (SARE). In some embodiments, the synaptic activity response element (SARE) is a human synaptic activity response element (hSARE). In some embodiments, the hSARE comprises a nucleic acid sequence of SEQ ID NO: 11, or a sequence at least 90% identical thereto. In some embodiments, the promoter comprises a human ArcMin (hArcMin) and at least one hSARE. In some embodiments, the promoter comprises hArcMin and one hSARE. In some embodiments, the promoter comprises a nucleic acid sequence of SEQ ID NO: 6, or a sequence at least 90% identical thereto. In some embodiments, the promoter comprises hArcMin and five hSAREs. In some embodiments, the promoter comprises a nucleic acid sequence of SEQ ID NO: 16, or a sequence at least 90% identical thereto.

In some embodiments, the promoter binds to a neuronal activity dependent transcription factor. In some embodiments, the neuronal activity dependent transcription factor is cAMP-responsive element binding protein (CREB), myocyte enhancer factor 2 (MEF2), serum response factor (SRF), or Elk-1. In some embodiments, the Rett-syndrome-associated gene encodes brain-derived neurotrophic factor (BDNF), insulin-like growth factor 1 (IGF1), methyl-CpG-binding protein 2 (MECP2), Huntingtin protein, Huntington-associated protein 1, Orthodenticle homeobox 2 (OTX-2), FXYD Domain Containing Ion Transport Regulator 1 (FXYD1), Neurexin-2-alpha (NRXN2), or Protein Kinase C Gamma (PRKCG). In some embodiments, the Rett-syndrome-associated gene encodes brain-derived neurotrophic factor (BDNF). In some embodiments, the BDNF is a human BDNF. In some embodiments, the BDNF is encoded by a nucleic acid sequence of SEQ ID NO: 7, or a sequence at least 90% identical thereto.

In some embodiments, at least one of the 5' ITR and the 3' ITR is about 110 to about 160 nucleotides in length. In some embodiments, the 5' ITR is the same length as the 3' ITR. In some embodiments, the 5' ITR and the 3' ITR have different lengths. In some embodiments, at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the 5' ITR comprises the sequence of SEQ ID NO: 1. In some embodiments, the 3' ITR comprises the sequence of SEQ ID NO: 2.

In some embodiments, the AAV cassette comprises a brain-derived neurotrophic factor (BDNF) short 3' UTR, or a BDNF long 3' UTR. In some embodiments, the BDNF short 3' UTR, or the BDNF long 3' UTR is located between the Rett-syndrome-associated gene and the 3' ITR. In some embodiments, the AAV cassette comprises a BDNF short 3' UTR. In some embodiments, the BDNF short 3' UTR comprises a nucleic acid sequence of SEQ ID NO: 8, or a sequence at least 90% identical thereto. In some embodiments, the AAV cassette comprises a BDNF long 3' UTR. In some embodiments, the BDNF long 3' UTR comprises a nucleic acid sequence of SEQ ID NO: 10, or a sequence at least 90% identical thereto.

In some embodiments, the AAV cassette comprises a polyadenylation signal. In some embodiments, the polyadenylation signal is a polyadenylation signal isolated or derived from one or more of the following genes: simian virus 40 (SV40), rBG, α-globin, β-globin, human collagen, human growth hormone (hGH), polyoma virus, human growth hormone (hGH) or bovine growth hormone (bGH). In some embodiments, the AAV cassette comprises a bGH polyadenylation signal. In some embodiments, the bGH polyadenylation signal comprises a nucleic acid sequence of SEQ ID NO: 9, or a sequence at least 90% identical thereto.

In some embodiments, the AAV cassette comprises at least one stuffer sequence. In some embodiments, the at least one stuffer sequence comprises a nucleic acid sequence of SEQ ID NO: 13, or a sequence at least 90% identical thereto. In some embodiments, the AAV expression cassette comprises a Kozak sequence, wherein the Kozak sequence overlaps with the start codon of the Rett-syndrome-associated gene. In some embodiments, the Kozak sequence comprises a nucleic acid sequence of SEQ ID NO: 14, or a sequence at least 90% identical thereto; or a nucleic acid sequence of SEQ ID NO: 15, or a sequence at least 90% identical thereto. In some embodiments, the AAV expression cassette comprises a nucleic acid sequence SEQ ID NO: 3, or a sequence at least 90% identical thereto; SEQ ID NO: 4 or a sequence at least 90% identical thereto; or SEQ ID NO: 5 or a sequence at least 90% identical thereto.

The disclosure provides plasmids comprising any one of the nucleic acids disclosed herein. The disclosure also provides cells comprising any one of the nucleic acids disclosed herein or any one of the plasmids disclosed herein. The disclosure further provides methods of producing a recombinant AAV vector, the method comprising contacting an AAV producer cell with any one of the nucleic acids disclosed herein, or any one of the plasmids disclosed herein. The disclosure provides recombinant AAV vectors produced by any one of the methods of producing a recombinant AAV vector disclosed herein. In some embodiments, the vector is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV. In some embodiments, the recombinant AAV vector is a single-stranded AAV (ssAAV). In some embodiments, the recombinant AAV vector is a self-complementary AAV (scAAV). In some embodiments, the AAV vector comprises a capsid protein of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the AAV vector comprises a capsid protein with one or more substitutions or mutations, as compared to a wildtype AAV capsid protein.

The disclosure provides compositions, comprising: (a) any one of the nucleic acids disclosed herein, any one of the plasmids disclosed herein, any one of the cells disclosed herein, or any one of the recombinant AAV vectors disclosed herein; and (b) a pharmaceutically acceptable carrier. The disclosure provides methods for expressing a Rett-syndrome-associated gene in a subject in need thereof, comprising administering to the subject a therapeutically effective amount of any one of the nucleic acids disclosed herein, any one of the plasmids disclosed herein, any one of the cells disclosed herein, or any one of the recombinant AAV vectors disclosed herein, or any one of the compositions disclosed herein. In some embodiments, the subject has Rett syndrome.

The disclosure provides methods for treating or delaying the onset of Rett syndrome in a subject, comprising administering to the subject a therapeutically effective amount of any one of the nucleic acids disclosed herein, any one of the plasmids disclosed herein, any one of the cells disclosed herein, or any one of the recombinant AAV vectors disclosed herein, or any one of the compositions disclosed herein. The disclosure provides methods for expressing brain-derived neurotrophic factor (BDNF) in a subject in need thereof, comprising administering to the subject a therapeutically effective amount of any one of the nucleic acids disclosed herein, any one of the plasmids disclosed herein, any one of the cells disclosed herein, or any one of the recombinant AAV vectors disclosed herein, or any one of the compositions disclosed herein.

In some embodiments, the subject has a cognitive disorder, or a stress-related disorder. In some embodiments, the subject has depression, obsessive-compulsive disorder, Alzheimer's disease, Huntington's disease, and dementia, anorexia nervosa and bulimia nervosa, schizophrenia, epilepsy, post-traumatic stress disorder, obesity, Rett syndrome, or post-chemotherapy cognitive impairment.

The disclosure provides methods for treating or delaying the onset of a BDNF-associated disease in a subject, comprising administering to the subject a therapeutically effective amount of any one of the nucleic acids disclosed herein, any one of the plasmids disclosed herein, any one of the cells disclosed herein, or any one of the recombinant AAV vectors disclosed herein, or any one of the compositions disclosed herein. In some embodiments, the BDNF-associated disease is a cognitive disorder, and/or a stress-related disorder. In some embodiments, the BDNF-associated disease is depression, obsessive-compulsive disorder, Alzheimer's disease, Huntington's disease, and dementia, anorexia nervosa, bulimia nervosa, schizophrenia, epilepsy, post-traumatic stress disorder, bipolar disease, Rett syndrome, major depressive disorder, or post-chemotherapy cognitive impairment.

The disclosure provides methods for treating or delaying the onset of a MECP2-associated disease in a subject, comprising administering to the subject a therapeutically effective amount of any one of the nucleic acids disclosed herein, any one of the plasmids disclosed herein, any one of the cells disclosed herein, or any one of the recombinant AAV vectors disclosed herein, or any one of the compositions disclosed herein. In some embodiments, the MECP2-associated disease is MECP2 duplication syndrome, MECP2-related severe neonatal encephalopathy, PPM-X syndrome, or Rett syndrome. In some embodiments, the subject is a human subject. In some embodiments, the nucleic acid, the plasmid, the cell, the recombinant AAV vector, or composition is administered by injection into the central nervous system. In some embodiments, the Rett Syndrome-associated gene is expressed in the neurons of the subject. In some embodiments, the neurons are active neurons.

These and other embodiments are addressed in more detail in the detailed description set forth below.

BRIEF DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
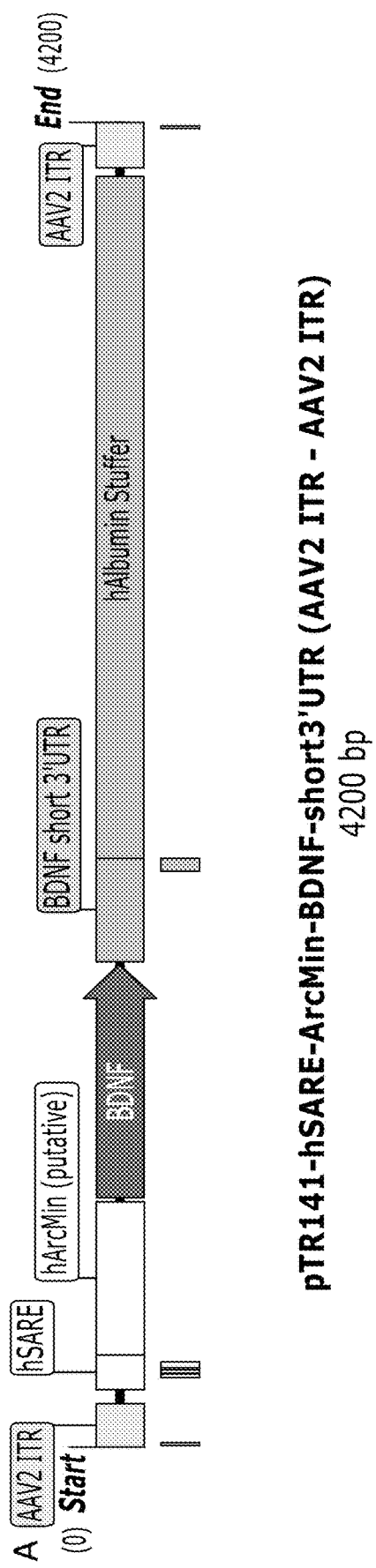
FIG. 1 shows an AAV expression cassette, comprising the hSARE-hArcMin promoter (SEQ ID NO: 6), BDNF gene (SEQ ID NO: 7), the BDNF short 3' UTR (SEQ ID NO: 8) and a stuffer sequence (SEQ ID NO: 13), all of which are flanked by a 5' ITR (SEQ ID NO: 1) and a 3' ITR (SEQ ID NO: 2).

Rett Syndrome is a rare genetic neurological disorder that occurs primarily in girls. The symptoms of the syndrome, which are apparent after 6 months to 18 months of age, may include one or more of the following: problems with language, problems with coordination, repetitive movements, slower growth, problems walking, smaller head size, seizures, scoliosis, cognitive disability, and sleeping problems. Patients with Rett Syndrome may exhibit any combination of these symptoms, with varying degrees of severity of each symptom.

Rett Syndrome is caused by a genetic mutation in the mecp2 gene, which encodes the methyl CpG binding protein 2 (MECP2) protein. See UniProt Accession No. P51608, incorporated herein by reference in its entirety. More than 620 mutations in the mecp2 gene, many of which are single base pair insertions or deletions, have been identified in females with Rett syndrome. MECP2 contributes to the normal functioning of nerve cells and is present in high levels in mature nerve cells. The methyl-CpG binding (MBD) of MECP2 domain can recognize DNA regions with 5-methyl cytosine modification. Mutations in the mecp2 gene can also cause other diseases such as MECP2 duplication syndrome, MECP2-related severe neonatal encephalopathy, and PPM-X syndrome. There are no approved therapies to treat any of the diseases associated with mutations in the mecp2 gene.

The disclosure provides nucleic acids (comprising AAV expression cassettes), AAV vectors, and compositions for use in methods for treating and/or delaying the onset of diseases associated with mutations in the mecp2 gene, such as Rett Syndrome. Also, provided herein are methods for treating and/or delaying the onset of brain-derived neurotrophic factor (BDNF)-associated diseases.

Definitions

The following terms are used in the description herein and the appended claims:

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

The term "wild type" is a term of the art understood by skilled persons and means the typical form of an organism, strain, gene, protein, or characteristic as it occurs in nature as distinguished from mutant or variant forms. For example, a wild type protein is the typical form of that protein as it occurs in nature.

The term "mutant protein" is a term of the art understood by skilled persons and refers to a protein that is distinguished from the wild type form of the protein on the basis of the presence of amino acid modifications, such as, for example, amino acid substitutions, insertions and/or deletions. The term "mutant gene" is a term of the art understood by skilled persons and refers to a gene that is distinguished from the wild type form of the gene on the basis of the presence of nucleic acid modifications, such as, for example, nucleic acid substitutions, insertions and/or deletions. In some embodiments, the mutant gene encodes a mutant protein.

A "nucleic acid" or "polynucleotide" is a sequence of nucleotide bases, for example RNA, DNA or DNA-RNA hybrid sequences (including both naturally occurring and non-naturally occurring nucleotides). In some embodiments, the nucleic acids of the disclosure are either single or double stranded DNA sequences. A nucleic acid may be 1-1,000, 1,000-10,000, 10,000-100,000, 100,000-1 million or greater than 1 million nucleotides in length. A nucleic acid will generally contain phosphodiester bonds, although in some cases nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones, non-ionic backbones, and non-ribose backbones. Nucleic acids containing one or more carbocyclic sugars are also included within the definition of nucleic acids. These modifications of the ribose-phosphate backbone may facilitate the addition of labels, or to increase the stability and half-life of such molecules in physiological environments. Nucleic acids of the disclosure may be linear, or may be circular (e.g., a plasmid).

As used herein, the term "promoter" refers to one or more nucleic acid control sequences that direct transcription of an operably linked nucleic acid. Promoters may include nucleic acid sequences near the start site of transcription, such as a TATA element. Promoters may also include cis-acting polynucleotide sequences that can be bound by transcription factors.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "AAV expression cassette" is a nucleic acid that gets packaged into a recombinant AAV vector, and comprises a sequence encoding one or more transgenes. When the AAV vector is contacted with a target cell, the transgenes are expressed by the target cell.

As used herein, the terms "virus vector," "viral vector," or "gene delivery vector" refer to a virus particle that functions as a nucleic acid delivery vehicle, and which comprises a nucleic acid (e.g., an AAV expression cassette) packaged within a virion. Exemplary virus vectors of the disclosure include adenovirus vectors, adeno-associated virus vectors (AAVs), lentivirus vectors, and retrovirus vectors.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV218, AAV2g9, AAV-LK03, AAV7m8, AAV Anc80, AAV PHP.B, and any other AAV now known or later discovered. See, e.g., Table 1.

TABLE 1

Adeno-Associated Virus Serotypes

| | GenBank Accession Number | | GenBank Accession Number | | GenBank Accession Number |
|---|---|---|---|---|---|
| Complete Genomes | | Clade C | | Rh57 | AY530569 |

TABLE 1-continued

Adeno-Associated Virus Serotypes

| | GenBank Accession Number | | GenBank Accession Number | | GenBank Accession Number |
|---|---|---|---|---|---|
| Adeno-associated virus 1 | NC_002077, AF063497 | Hu9 | AY530629 | Rh50 | AY530563 |
| Adeno-associated virus 2 | NC_001401 | Hu10 | AY530576 | Rh49 | AY530562 |
| Adeno-associated virus 3 | NC_001729 | Hu11 | AY530577 | Hu39 | AY530601 |
| Adeno-associated virus 3B | NC_001863 | Hu53 | AY530615 | Rh58 | AY530570 |
| Adeno-associated virus 4 | NC_001829 | Hu55 | AY530617 | Rh61 | AY530572 |
| Adeno-associated virus 5 | Y18065, AF085716 | Hu54 | AY530616 | Rh52 | AY530565 |
| Adeno-associated virus 6 | NC_001862, AAB95450.1 | Hu7 | AY530628 | Rh53 | AY530566 |
| Avian AAV ATCC VR-865 | AY186198, AY629583, NC_004828 | Hu18 | AY530583 | Rh51 | AY530564 |
| Avian AAV strain DA-1 | NC_006263, AY629583 | Hu15 | AY530580 | Rh64 | AY530574 |
| Bovine AAV | NC_005889, AY388617, AAR26465 | Hu16 | AY530581 | Rh43 | AY530560 |
| AAV11 | AAT46339, AY631966 | Hu25 | AY530591 | AAV8 | AF513852 |
| AAV12 | ABI16639, DQ813647 | Hu60 | AY530622 | Rh8 | AY242997 |
| Clade A | | Ch5 | AY243021 | Rh1 | AY530556 |
| AAV1 | NC_002077, AF063497 | Hu3 | AY530595 | Clade F | |
| AAV6 | NC_001862 | Hu1 | AY530575 | Hu14 (AAV9) | AY530579 |
| Hu.48 | AY530611 | Hu4 | AY530602 | Hu31 | AY530596 |
| Hu 43 | AY530606 | Hu2 | AY530585 | Hu32 | AY530597 |
| Hu 44 | AY530607 | Hu61 | AY530623 | HSC1 | MI332400.1 |
| Hu 46 | AY530609 | Clade D | | HSC2 | MI332401.1 |
| Clade B | | Rh62 | AY530573 | HSC3 | MI332402.1 |
| Hu. 19 | AY530584 | Rh48 | AY530561 | HSC4 | MI332403.1 |
| Hu. 20 | AY530586 | Rh54 | AY530567 | HSC5 | MI332405.1 |
| Hu 23 | AY530589 | Rh55 | AY530568 | HSC6 | MI332404.1 |
| Hu22 | AY530588 | Cy2 | AY243020 | HSC7 | MI332407.1 |
| Hu24 | AY530590 | AAV7 | AF513851 | HSC8 | MI332408.1 |
| Hu21 | AY530587 | Rh35 | AY243000 | HSC9 | MI332409.1 |
| Hu27 | AY530592 | Rh37 | AY242998 | HSC11 | MI332406.1 |
| Hu28 | AY530593 | Rh36 | AY242999 | HSC12 | MI332410.1 |
| Hu 29 | AY530594 | Cy6 | AY243016 | HSC13 | MI332411.1 |
| Hu63 | AY530624 | Cy4 | AY243018 | HSC14 | MI332412.1 |
| Hu64 | AY530625 | Cy3 | AY243019 | HSC15 | MI332413.1 |
| Hu13 | AY530578 | Cy5 | AY243017 | HSC16 | MI332414.1 |
| Hu56 | AY530618 | Rh13 | AY243013 | HSC17 | MI332415.1 |
| Hu57 | AY530619 | Clade E | | Hu68 | |
| Hu49 | AY530612 | Rh38 | AY530558 | Clonal Isolate | |
| Hu58 | AY530620 | Hu66 | AY530626 | AAV5 | Y18065, AF085716 |
| Hu34 | AY530598 | Hu42 | AY530605 | AAV 3 | NC_001729 |
| Hu35 | AY530599 | Hu67 | AY530627 | AAV 3B | NC_001863 |
| AAV2 | NC_001401 | Hu40 | AY530603 | AAV4 | NC_001829 |
| Hu45 | AY530608 | Hu41 | AY530604 | Rh34 | AY243001 |
| Hu47 | AY530610 | Hu37 | AY530600 | Rh33 | AY243002 |
| Hu51 | AY530613 | Rh40 | AY530559 | Rh32 | AY243003 |
| Hu52 | AY530614 | Rh2 | AY243007 | Others | |
| Hu T41 | AY695378 | Bb1 | AY243023 | Rh74 | |
| Hu S17 | AY695376 | Bb2 | AY243022 | Bearded Dragon AAV | |
| Hu T88 | AY695375 | Rh10 | AY243015 | Snake AAV | NC_006148.1 |
| Hu T71 | AY695374 | Hu17 | AY530582 | | |
| Hu T70 | AY695373 | Hu6 | AY530621 | | |
| Hu T40 | AY695372 | Rh25 | AY530557 | | |
| Hu T32 | AY695371 | Pi2 | AY530554 | | |
| Hu T17 | AY695370 | Pi1 | AY530553 | | |
| Hu LG15 | AY695377 | Pi3 | AY530555 | | |

The terms "viral production cell", "viral production cell line," or "viral producer cell" refer to cells used to produce viral vectors. HEK293 and 239T cells are common viral production cell lines. Table 2, below, lists exemplary viral production cell lines for various viral vectors.

TABLE 2

Exemplary viral production cell lines

| Virus Vector | Exemplary Viral Production Cell Line(s) |
|---|---|
| Adenovirus | HEK293, 911, pTG6559, PER.C6, GH329, N52.E6, HeLa-E1, UR, VLI-293 |
| Adeno-Associated Virus (AAV) | HEK293, Sf9 |
| Retrovirus | HEK293 |
| Lentivirus | 293T |

"HEK293" refers to a cell line originally derived from human embryonic kidney cells grown in tissue culture. The HEK293 cell line grows readily in culture, and is commonly used for viral production. As used herein, "HEK293" may also refer to one or more variant HEK293 cell lines, i.e., cell lines derived from the original HEK293 cell line that additionally comprise one or more genetic alterations. Many variant HEK293 lines have been developed and optimized for one or more particular applications. For example, the 293T cell line contains the SV40 large T-antigen that allows for episomal replication of transfected plasmids containing the SV40 origin of replication, leading to increased expression of desired gene products.

"Sf9" refers to an insect cell line that is a clonal isolate derived from the parental Spodoptera frugiperda cell line IPLB-Sf-21-AE. Sf9 cells can be grown in the absence of serum and can be cultured attached or in suspension.

A "transfection reagent" means a composition that enhances the transfer of nucleic acid into cells. Some transfection reagents commonly used in the art include one or more lipids that bind to nucleic acids and to the cell surface (e.g., Lipofectamine™).

Methods of determining sequence similarity or identity between two or more amino acid sequences are known in the art. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85,2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

As used herein, "treatment" or "treating," or "palliating" or "ameliorating" are used interchangeably. These terms refer to an approach for obtaining beneficial or desired results including but not limited to a therapeutic benefit and/or a prophylactic benefit. Therapeutic benefit refers to any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The terms "subject," "individual," and "patient" are used interchangeably herein to refer to a vertebrate, such as a mammal. The mammal may be, for example, a mouse, a rat, a rabbit, a cat, a dog, a pig, a sheep, a horse, a non-human primate (e.g., cynomolgus monkey, chimpanzee), or a human. A subject's tissues, cells, or derivatives thereof, obtained in vivo or cultured in vitro are also encompassed. A human subject may be an adult, a teenager, a child (2 years to 14 years of age), an infant (1 month to 24 months), or a neonate (up to 1 month). In some embodiments, the adults are seniors about 65 years or older, or about 60 years or older. In some embodiments, the subject is a pregnant woman or a woman intending to become pregnant.

The term "effective amount" or "therapeutically effective amount" refers to the amount of an agent that is sufficient to achieve an outcome, for example, to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, the term "gene therapy" refers to the process of introducing genetic material into cells to compensate for abnormal genes, or to make a therapeutic protein.

As used herein, a neuron is said to be an "active" neuron or to have "neuronal activity" when at least a part of the neuronal plasma membrane is depolarized. In some embodiments, the depolarization is caused by opening of voltage-gated $Na^+$ channels. In some embodiments, the depolarization of the neuronal plasma membrane leads to the influx of $Ca^{2-}$ ions into the cell and triggers downstream transcription of immediate early genes (IEG). In vivo, depolarization of at least a part of the plasma membrane of a post-synaptic neuron may be triggered by a signal from a pre-synaptic neuron. In vitro, depolarization may be induced by treating neurons with KCl. Depolarization may also be promoted in vitro by using small molecules (e.g. bicuculline) to inactivate signal receptors, such as γ-Aminobutyric acid type A (GABAA) receptor, which normally slows down depolarization by opening $Cl^-$ or $K^+$ channels.

As used herein, a neuron is said to be a "resting" neuron when there is no net flow of ions across the plasma membrane of the neuron. In some embodiments, no part of the resting neuronal plasma membrane is depolarized. In some embodiments, the resting neuron has a resting membrane potential of about −70 mV.

AAV Expression Cassettes

The disclosure provides nucleic acid sequences comprising one or more adeno-associated virus (AAV) expression cassettes. In some embodiments, the AAV expression cassette comprises a 5' inverted terminal repeat (ITR), a promoter, a transgene, and a 3' ITR. In some embodiments, the transgene is a Rett Syndrome-associated gene. In some embodiments, the AAV expression cassette comprises a Kozak sequence, a polyadenylation sequence, and/or a stuffer sequence.

In some embodiments, the AAV expression cassette comprises a nucleic acid sequence of SEQ ID NO: 3, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie therebetween). In some embodiments, the AAV expression cassette comprises a nucleic acid sequence of SEQ ID NO: 4, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie there between). In some embodiments, the AAV expression cassette comprises a nucleic acid sequence of SEQ ID NO: 5, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie therebetween).

(i) Inverted Terminal Repeat

Inverted Terminal Repeat or ITR sequences are sequences that mediate AAV proviral integration and packaging of AAV DNA into virions. ITRs are involved in a variety of activities in the AAV life cycle. For example, the ITR sequences, which can form a hairpin structure, play roles in excision from the plasmid after transfection, replication of the vector genome and integration and rescue from a host cell genome.

The AAV expression cassettes of the disclosure may comprise a 5' ITR and a 3' ITR. The ITR sequences may be about 110 to about 160 nucleotides in length, for example 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159 or 160 nucleotides in length. In some embodiments, the ITR sequences may be about 141 nucleotides in length. In some embodiments, the 5' ITR is the same length as the 3' ITR. In some embodiments, the 5' ITR and the 3' ITR have different lengths. In some embodiments, the 5' ITR is longer than the 3' ITR, and in other embodiments, the 3' ITR is longer than the 5' ITR.

The ITRs may be isolated or derived from the genome of any AAV, for example the AAVs listed in Table 1. In some embodiments, at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, at least one of the 5' ITR and the 3'ITR may be a wildtype or mutated ITR isolated derived from a member of another parvovirus species besides AAV. For example, in some embodiments, an ITR may be a wildtype or mutant ITR isolated or derived from bocavirus or parvovirus B19.

In some embodiments, the ITR comprises a modification to promote production of a scAAV. In some embodiments, the modification to promote production of a scAAV is deletion of the terminal resolution sequence (TRS) from the ITR. In some embodiments, the 5' ITR is a wildtype ITR, and the 3' ITR is a mutated ITR lacking the terminal resolution sequence. In some embodiments, the 3' ITR is a wildtype ITR, and the 5' ITR is a mutated ITR lacking the terminal resolution sequence. In some embodiments, the terminal resolution sequence is absent from both the 5' ITR and the 3'ITR. In other embodiments, the modification to promote production of a scAAV is replacement of an ITR with a different hairpin-forming sequence, such as a shRNA-forming sequence.

In some embodiments, the 5' ITR may comprise the sequence of SEQ ID NO: 1, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie there between). In some embodiments, the 3' ITR may comprise the sequence of SEQ ID NO: 2, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie there between). In some embodiments, the 5' ITR comprises the sequence of SEQ ID NO: 1, and the 3' ITR comprises the sequence of SEQ ID NO: 2.

In some embodiments, the AAV expression cassettes comprise one or more "surrogate" ITRs, i.e., non-ITR sequences that serve the same function as ITRs. See, e.g., Xie, J. et al., Mol. Ther., 25(6): 1363-1374 (2017). In some embodiments, an ITR in an AAV expression cassette is replaced by a surrogate ITR. In some embodiments, the surrogate ITR comprises a hairpin-forming sequence. In some embodiments, the surrogate ITR is a short hairpin (sh)RNA-forming sequence.

(ii) Activity-Dependent Promoters

In some embodiments, the AAV expression cassettes described herein comprise a promoter. In some embodiments, the promoter is a tissue-specific promoter. In some embodiments, the promoter is a synthetic promoter. In some embodiments, the promoter may comprise a nucleic acid sequence derived from an endogenous promoter and/or an endogenous enhancer. In some embodiments, the promoter may comprise a nucleic acid sequence derived from the region upstream of the initiation codon of a gene. The nucleic acid sequence may lie within 1 base pair (bp) to within about 8000 bps upstream of the initiation codon, for example, within about 10 bps, 50 bps, 100 bps, 500 bps, 1000 bps, 1500 bps, 2000 bps, 2500 bps, 3000 bps, 3500 bps, 4000 bps, 4500 bps, 5000 bps, 5500 bps, 6000 bps, 6500 bps, 7000 bps, 7500 bps, or 8000 bps, inclusive of all subranges and values that lie therebetween, upstream of the initiation codon.

Without being bound by any theory, it is thought that MECP2 function contributes to expression of target genes involved in neuronal function. The expression of these target genes is affected when MECP2 is mutated. Restoring the expression of these target genes in a MECP2 independent manner may alleviate the symptoms of diseases associated with, or caused by, MECP2 mutations. Accordingly, in some embodiments, the promoter is a MECP2-independent promoter. As used herein, a "MECP2-independent promoter" refers to a promoter whose function is not impaired by reduced MECP2 function, or loss of MECP2 function.

Without being bound by any theory, it is thought that constitutive expression of target genes involved in neuronal function may be detrimental. Accordingly, in some embodiments, the promoter is an inducible promoter. In some embodiments, the function of the promoter is dependent on the presence of one or more stimuli. In some embodiments, the promoter is an activity-dependent promoter. As used herein, the function of an "activity-dependent promoter", interchangeably used with "neuronal activity-dependent promoter", is induced by neuronal activity. In some embodiments, the activity-dependent promoter is induced by the influx of calcium ions into the neuron. In some embodiments, the activity-dependent promoter is used to drive the expression of any target gene that when expressed constitutively in a cell (such as, a neuron), is detrimental.

In some embodiments, the promoter comprises a nucleic acid sequence derived from a promoter and/or an enhancer of a neuronal immediate early gene. The identity of the neuronal immediate early gene is not limited, and may refer to any neuronal immediate early gene known in the art, or identified in the future. Non-limiting examples of neuronal immediate early genes include Arc gene, the c-fos gene, and the egr-1 gene. Therefore, in some embodiments, the promoter comprises a nucleic acid sequence derived from the promoter and/or an enhancer of Arc gene, the c-fos gene, or the egr-1 gene. In some embodiments, the promoter comprises a nucleic acid sequence derived from the promoter and/or an enhancer of a neurotrophin gene. Non-limiting examples of neurotrophin genes include bdnf (brain-derived neurotrophic factor) gene, ngf (nerve growth factor) gene, neutrophin-3 gene and neurotrophin-4 gene.

In some embodiments, the promoter is capable of binding to one or more neuronal activity-dependent transcription factors. As used herein, a "neuronal activity dependent transcription factor" is a transcription factor that is activated in response to neuronal activity. In some embodiments the neuronal activity-dependent transcription factor promotes gene expression in response to neuronal activity. In some embodiments, the neuronal activity-dependent transcription factor represses gene expression in response to neuronal activity. In some embodiments, the neuronal activity-dependent transcription factor is activated by calcium-dependent kinase cascades.

In some embodiments, the promoter comprises one or more nucleic acid sequences that are capable of binding to one or more neuronal activity-dependent transcription factors. Non-limiting examples of neuronal activity-dependent transcription factors include cAMP-responsive element binding protein (CREB), myocyte enhancer factor 2

(MEF2), serum response factor (SRF), or Elk-1. In some embodiments, the promoter is capable of binding to more than one neuronal activity-dependent transcription factor, for example, the promoter is capable of binding to 2, 3, 4, or 5 neuronal activity-dependent transcription factors. In some embodiments, the promoter is capable of binding to two neuronal activity-dependent transcription factors. In some embodiments, the promoter is capable of binding to three neuronal activity-dependent transcription factors. In some embodiments, the promoter is capable of binding to the following neuronal activity-dependent transcription factors: CREB, MEF2 and SRF.

In some embodiments, the promoter comprises one or more response elements. As used herein, a "response element" is a region of the promoter that contributes to driving gene expression in the presence of a stimulant. In some embodiments, the response element is critical for the promoter to drive gene expression in the presence of the stimulant. Non-limiting examples of stimulant include hormones; environmental cues, such as heat or light; and chemical ions such as calcium. In some embodiments, the promoter comprises a response element that drives gene expression in the presence of calcium. In some embodiments, the promoter comprises a response element that is present in the promoters of neuronal immediate early genes. In some embodiments, the promoters comprises a response element that is present in the promoter of the Arc gene, the c-fos gene, and/or the egr-1 gene.

In some embodiments, the response element comprises one or more of the following: cyclic AMP response element (CRE), a serum response element (SRE), a synaptic activity response element (SARE), and a MEF2 response element (MRE). In some embodiments, the promoter comprises one or more CREs; one or more SREs; one or more SAREs; one or more MREs, or any combination thereof. In some embodiments, the response element binds to one or more neuronal activity dependent transcription factors. In some embodiments, the CRE binds to CREB. In some embodiments, the SRE binds to SRF. In some embodiments, the MRE binds to MEF2. In some embodiments, the SARE binds to CREB, MEF2 and SRF.

In some embodiments, the promoter comprises 1-20 SAREs, for example, 1, 2, 3, 4, 5, 6, 7, 8, 9, 10, 11, 12, 13, 14, 15, 16, 17, 18, 19, or 20 SAREs. In some embodiments, the promoter comprises 1 SARE. In some embodiments, the promoter comprises 5 SAREs. In some embodiments, the SARE is a mouse SARE. In some embodiments, the SARE is a human synaptic activity response element (hSARE). In some embodiments, the hSARE comprises a nucleic acid sequence with at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 11. In some embodiments, the hSARE comprises a nucleic acid sequence of SEQ ID NO: 11, or a sequence at least 90% identical thereto.

In some embodiments, the promoter comprises a nucleic acid sequence derived from the promoter of the Arc gene. In some embodiments, the Arc gene is the mouse Arc gene. In some embodiments, the Arc gene is the human Arc gene. In some embodiments, the promoter comprises a region spanning nucleic acids −300 to +300 of the Arc gene, or any subregion thereof. In some embodiments, the promoter comprises a minimal Arc gene promoter (ArcMin). In some embodiments, the human ArcMin (hArcMin) comprises a short upstream sequence and 5' UTR (−276 to +208) of the Arc gene. In some embodiments, the mouse ArcMin (mArcMin) comprises a short upstream sequence and 5' UTR (−222 to +198) of the Arc gene. In some embodiments, the hArcMin comprises a nucleic acid sequence with at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 12. In some embodiments, the hArcMin comprises a nucleic acid sequence of SEQ ID NO: 12, or a sequence at least 90% identical thereto.

In some embodiments, the promoter comprises hArcMin and at least one hSARE. The number of hSAREs in the promoter is not limited, and may be in the range of 1 hSARE to 20 hSAREs, such as, 1, 2, 3, 4, 5, 6, 7, 8, 9, 10, 11, 12, 13, 14, 15, 16, 17, 18, 19, or 20 hSARES. In some embodiments, the promoter comprises hArcMin and one hSARE (called SARE-ArcMin). In some embodiments, the SARE-ArcMin comprises a nucleic acid sequence with at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 6. In some embodiments, the SARE-ArcMin comprises a nucleic acid sequence of SEQ ID NO: 6, or a sequence at least 90% identical thereto. In some embodiments, the promoter comprises hArcMin and 5 hSAREs (called E-SARE). In some embodiments, the E-SARE comprises a nucleic acid sequence with at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie there between) to the nucleic acid sequence of SEQ ID NO: 16. In some embodiments, the E-SARE comprises a nucleic acid sequence of SEQ ID NO: 16, or a sequence at least 90% identical thereto. Further details regarding hArcMin and hSARE are provided in Kawashima et al., *Nat Methods* 10, 889-895 (2013), Kawashima et al., *Front Neural Circuits* 2014 Apr. 23; 8:37, and Kawashima et al., PNAS Jan. 6, 2009 106 (1) 316-32, each of which is incorporated herein by reference in its entirety.

In some embodiments, the promoter induces a level of gene expression that higher than an endogenous promoter of a neuronal immediate early gene, such as Arc gene, the c-fos gene, or the egr-1 gene. In some embodiments, the promoter induces a level of gene expression that is at least 1.5 fold higher than an endogenous promoter of a neuronal immediate early gene, such as Arc gene, the c-fos gene, or the egr-1 gene. In some embodiments, the promoter induces a level of gene expression that is about 1.5-fold to about 100-fold (for example, about 2-fold, about 3-fold, about 4-fold, about 5-fold, about 10-fold, about 15-fold, about 20-fold, about 30-fold, about 40-fold, about 50-fold, about 60-fold, about 70-fold, about 80-fold, about 90-fold, or about 100-fold) higher than an endogenous promoter of a neuronal immediate early gene, such as Arc gene, the c-fos gene, or the egr-1 gene.

In some embodiments, the promoter comprises a nucleic acid sequence derived from one or more promoters commonly used in the art for gene expression. For instance, in some embodiments, the promoter further comprises a nucleic acid sequence derived from the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the dihydrofolate reductase (DHFR) promoter, and the phosphoglycerol kinase (PGK) promoter. In some embodiments, the promoter comprises a nucleic acid sequence derived from the chicken β-actin (CBA) promoter, the EF-1 alpha promoter, or the EF-1 alpha short promoter. In some embodiments, the promoter comprises a sequence selected from any one of SEQ ID NOs: 17-20, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie there between).

In some embodiments, the AAV expression cassettes described herein further comprise an enhancer. The enhancer may be, for example, the CMV enhancer. In some embodiments, the enhancer comprises the sequence of SEQ ID NO: 21, or a sequence at least 70% identical thereto (for example, at least 75%, at least 80%, at least 85%, at least 90%, at least 95%, at least 96%, at least 97%, at least 98%, at least 99%, at least 99.5%, or 100% identical thereto, inclusive of all values and subranges that lie therebetween).

In some embodiments, the promoter further comprises a nucleic acid sequence derived from any one or more of the following promoters: HMG-COA reductase promoter; sterol regulatory element 1 (SRE-1); phosphoenol pyruvate carboxy kinase (PEPCK) promoter; human C-reactive protein (CRP) promoter; human glucokinase promoter; cholesterol 7-alpha hydroylase (CYP-7) promoter; beta-galactosidase alpha-2,6 sialyltransferase promoter; insulin-like growth factor binding protein (IGFBP-1) promoter; aldolase B promoter; human transferrin promoter; collagen type I promoter; prostatic acid phosphatase (PAP) promoter; prostatic secretory protein of 94 (PSP 94) promoter; prostate specific antigen complex promoter; human glandular kallikrein gene promoter (hgt-1); the myocyte-specific enhancer binding factor MEF-2; muscle creatine kinase promoter; pancreatitis associated protein promoter (PAP); elastase 1 transcriptional enhancer; pancreas specific amylase and elastase enhancer promoter; pancreatic cholesterol esterase gene promoter; uteroglobin promoter; cholesterol side-chain cleavage (SCC) promoter; gamma-gamma enolase (neuron-specific enolase, NSE) promoter; neurofilament heavy chain (NF-H) promoter; human CGL-1/granzyme B promoter; the terminal deoxy transferase (TdT), lambda 5, VpreB, and lck (lymphocyte specific tyrosine protein kinase p56lck) promoter; the humans CD2 promoter and its 3' transcriptional enhancer; the human NK and T cell specific activation (NKG5) promoter; pp60c-src tyrosine kinase promoter; organ-specific neoantigens (OSNs), mw 40 kDa (p40) promoter; colon specific antigen-P promoter; human alpha-lactalbumin promoter; phosphoeholpyruvate carboxykinase (PEPCK) promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, alpha or beta globin promoter, T-cell receptor promoter, the osteocalcin promoter the IL-2 promoter, IL-2 receptor promoter, whey (wap) promoter, and the MHC Class II promoter.

(iii) Rett Syndrome-Associated Gene

As used herein, a "Rett Syndrome-associated gene" refers to any gene in a subject with Rett syndrome which can be targeted by gene therapy to alleviate at least one sign or symptom of Rett Syndrome. In some embodiments, the level of the protein encoded by the Rett Syndrome-associated gene is reduced or undetectable in subjects with Rett syndrome. In some embodiments, the levels of the protein encoded by the Rett Syndrome-associated gene decreases upon the onset of at least one symptom of Rett Syndrome. In some embodiments, the levels of the protein encoded by the Rett Syndrome-associated gene increases in normal post-natal development and/or neuronal development. In some embodiments, the Rett Syndrome-associated gene encodes a protein that contributes to normal neuronal function. In some embodiments, the Rett Syndrome-associated gene encodes a protein that is involved in promoting and/or maintaining synaptic plasticity. In some embodiments, the Rett Syndrome-associated gene is a neurotrophin. In some embodiments, mutations in the Rett Syndrome-associated gene, or loss of function of the Rett Syndrome-associated gene, is present in subjects with Rett Syndrome. In some embodiments, mutations in the Rett Syndrome-associated gene, or loss of function of the Rett Syndrome-associated gene, causes Rett Syndrome. In some embodiments, mutations in the Rett Syndrome-associated gene, or loss of function of the Rett Syndrome-associated gene, particularly in forebrain excitary neurons, causes symptoms similar to the loss of mecp2 gene. The type of mutation is not limited, and may be an insertion, deletion, duplication and/or substitution.

The disclosure provides AAV expression cassettes comprising a Rett Syndrome-associated gene. In some embodiments, an AAV expression cassette comprises a Rett Syndrome-associated gene which encodes a protein, including therapeutic (e.g., for medical or veterinary uses) or immunogenic (e.g., for vaccines) polypeptide. In some embodiments, AAV expression cassette comprises a mammalian Rett Syndrome-associated gene. In some embodiments, the AAV expression cassette comprises a human Rett Syndrome-associated gene. In some embodiments, the AAV expression cassette comprises a Rett Syndrome-associated gene that encodes brain-derived neurotrophic factor (BDNF), insulin-like growth factor 1 (IGF1), methyl-CpG-binding protein 2 (MECP2), Huntingtin protein, Huntington-associated protein 1, Orthodenticle homeobox 2 (OTX-2), FXYD Domain Containing Ion Transport Regulator 1 (FXYD1), Neurexin-2-alpha (NRXN2), or Protein Kinase C Gamma (PRKCG). In some embodiments, the Rett Syndrome-associated gene is a gene selected from the group consisting of KCNA1 (Potassium Voltage-Gated Channel Subfamily A Member 1), GABRA1 (Gamma-Aminobutyric Acid Type A Receptor Subunit Alpha1), MAPKI (Mitogen-Activated Protein Kinase 1), NRXN2 (Neurexin 2), RBFOX1 (RNA Binding Fox-1 Homolog 1), GNAO1 (G Protein Subunit Alpha O1), NCAN (Neurocan), PRKCG (Protein Kinase C Gamma), KCNJ4 (Potassium Inwardly Rectifying Channel Subfamily J Member 4), CAMK2B (Calcium/Calmodulin Dependent Protein Kinase II Beta), EFNB3 (Ephrin B3), GABBR1 (Gamma-Aminobutyric Acid Type B Receptor Subunit 1), LY6H (Lymphocyte Antigen 6 Family Member H), KCNA2 (Potassium Voltage-Gated Channel Subfamily A Member 2), and NEFL (Neurofilament Light Chain).

In some embodiments, the Rett-syndrome-associated gene encodes brain-derived neurotrophic factor (BDNF). BDNF is a neurotrophin that functions in supporting survival and growth of neurons, synaptic development, and plasticity. BDNF expression is altered in Rett syndrome. Loss of function of bdnf results in phenotypes similar to loss of function of mecp2, and BDNF function is affected upon loss of mecp2 function. Further details about BDNF function are provided in Eduardo E. Benarroch, *Neurology* April 2015, 84 (16) 1693-1704; Chang et al. Neuron. 2006; 49(3): 341-348; and Zhou et al., *Neuron* 52, 255-269, Oct. 19, 2006, each of which is incorporated herein by reference in its entirety. In some embodiments, the BDNF is a human BDNF. In some embodiments, the BDNF is encoded by a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie there between) to the nucleic acid sequence of SEQ ID NO: 7. In some embodiments, the BDNF is encoded by a nucleic acid sequence of SEQ ID NO: 7, or a sequence at least 90% identical thereto.

There are two alternate polyadenylated transcription stop sites in BDNF, which generate two distinct populations of bdnf mRNA, with either short 3' UTR (about 0.35 kb long), or long 3' UTR (about 2.85 kb long). The bdnf mRNA variant with the short 3' UTR is mostly localized to the cell body of neurons, whereas the bdnf mRNA variant with the long 3' UTR is also localized to dendrites. In some embodiments, the AAV expression cassette comprises BDNF short 3' UTR, or the BDNF long 3' UTR. In some embodiments, the BDNF short 3' UTR, or the BDNF long 3' UTR is present between the stop codon and the 3' ITR.

In some embodiments, the BDNF short 3' UTR comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 8. In some embodiments, the BDNF short 3' UTR comprises a nucleic acid sequence of SEQ ID NO: 8, or a sequence at least 90% identical thereto. In some embodiments, the BDNF short 3' UTR comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 10. In some embodiments, the BDNF long 3' UTR comprises a nucleic acid sequence of SEQ ID NO: 10, or a sequence at least 90% identical thereto.

In some embodiments, the AAV expression cassette comprises a Kozak sequence. The Kozak sequence is a nucleic acid sequence that functions as a protein translation initiation site in many eukaryotic mRNA transcripts. In some embodiments, the Kozak sequence overlaps with the start codon. In some embodiments, the Kozak sequence comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 14 or SEQ ID NO: 15. In some embodiments, the Kozak sequence comprises a nucleic acid sequence of SEQ ID NO: 14, or a sequence at least 90% identical thereto; or a nucleic acid sequence of SEQ ID NO: 15, or a sequence at least 90% identical thereto.

(iv) Polyadenylation (PolyA) Signal

Polyadenylation signals are nucleotide sequences found in nearly all mammalian genes and control the addition of a string of approximately 200 adenosine residues (the poly(A) tail) to the 3' end of the gene transcript. The poly(A) tail contributes to mRNA stability, and mRNAs lacking the poly(A) tail are rapidly degraded. There is also evidence that the presence of the poly(A) tail positively contributes to the translatability of mRNA by affecting the initiation of translation.

In some embodiments, the AAV expression cassettes of the disclosure comprise a polyadenylation signal. The polyadenylation signal may be selected from the polyadenylation signal of simian virus 40 (SV40), rBG. α-globin, β-globin, human collagen, human growth hormone (hGH), polyoma virus, human growth hormone (hGH) and bovine growth hormone (bGH).

In some embodiments, the AAV expression cassette comprises a bGH polyadenylation signal. In some embodiments, the bGH polyadenylation signal comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 9. In some embodiments, the bGH polyadenylation signal comprises a nucleic acid sequence of SEQ ID NO: 9, or a sequence at least 90% identical thereto.

In some embodiments, the polyadenylation signal is the SV40 polyadenylation signal. In some embodiments, the polyadenylation signal is the rBG polyadenylation signal. In some embodiments, the polyadenylation signal comprises the sequence of SEQ ID NO: 22 or SEQ ID NO: 23. In some embodiments, the polyadenylation signal comprises a sequence at least 90%, at least 95%, at least 96%, at least 97%, at least 98%, or at least 99% identical to the sequence of SEQ ID NO: 22 or SEQ ID NO: 23.

(v) Stuffer Sequences

AAV vectors typically accept inserts of DNA having a defined size range which is generally about 4 kb to about 5.2 kb, or slightly more. Thus, for shorter sequences, it may be necessary to include additional nucleic acid in the insert fragment in order to achieve the required length which is acceptable for the AAV vector. Accordingly, in some embodiments, the AAV expression cassettes of the disclosure may comprise a stuffer sequence. The stuffer sequence may be for example, a sequence between 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, or 4,500-5,000, or more nucleotides in length. The stuffer sequence can be located in the cassette at any desired position such that it does not prevent a function or activity of the vector. In some embodiments, the stuffer sequence is located upstream of the 3' UTR. For instance, in some embodiments, the stuffer sequence is present between the BDNF short 3' UTR and the 3' ITR, or between the bGH poly A signal and the 3' ITR.

In some embodiments, the AAV cassette comprises at least one stuffer sequence. In some embodiments, the stuffer sequence comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 13. In some embodiments, the stuffer sequence comprises a nucleic acid sequence of SEQ ID NO: 13, or a sequence at least 90% identical thereto.

(vi) Intronic Sequences

In some embodiments, the AAV expression cassettes of the disclosure may comprise an intronic sequence. Inclusion of an intronic sequence may enhance expression compared with expression in the absence of the intronic sequence.

In some embodiments, the intronic sequence is a hybrid or chimeric sequence. In some embodiments, the intronic sequence is isolated or derived from an intronic sequence of one or more of SV40, β-globin, chicken beta-actin, minute virus of mice (MVM), factor IX, and/or human IgG (heavy or light chain). In some embodiments, the intronic sequence is chimeric. In some embodiments, the intronic sequence comprises the sequence of SEQ ID NO: 24 or SEQ ID NO: 25. In some embodiments, the intronic sequence comprises a nucleic acid sequence having at least 70% identity (for example, at least 75%, at least 80%, at least 85%, at least 90%, at least 95%, at least 96%, at least 97%, at least 98%, at least 99%, at least 99.5%, or 100% identity, inclusive of all values and subranges that lie therebetween) to the nucleic acid sequence of SEQ ID NO: 24 or SEQ ID NO: 25.

(vii) Exemplary AAV Expression Cassettes

In some embodiments, the AAV expression cassette comprises a 5' inverted terminal repeat (ITR), a transgene, and a 3' ITR. In some embodiments, the AAV expression cassette comprises SEQ ID NO: 1 (5' ITR), SEQ ID NO: 7 (BDNF) and SEQ ID NO: 2 (3' ITR).

In some embodiments, the AAV expression cassette comprises a 5' ITR, a promoter, a transgene, and a 3' ITR. In some embodiments, the AAV expression cassette comprises SEQ ID NO: 1 (5' ITR), SEQ ID NO: 6 (hSARE-ArcMin), SEQ ID NO: 7 (BDNF) and SEQ ID NO: 2 (3' ITR). In some embodiments, the AAV expression cassette comprises SEQ ID NO: 1 (5' ITR), SEQ ID NO: 16 (E-SARE), SEQ ID NO: 7 (BDNF) and SEQ ID NO: 2 (3' ITR).

In some embodiments, the AAV expression cassette comprises a 5' ITR, a promoter, a transgene, a polyadenylation sequence and a 3' ITR. In some embodiments, the AAV expression cassette comprises SEQ ID NO: 1 (5' ITR), SEQ ID NO: 6 (hSARE-ArcMin), SEQ ID NO: 7 (BDNF), SEQ ID NO: 9 (bGH polyadenylation sequence) and SEQ ID NO: 2 (3' ITR). In some embodiments, the AAV expression cassette comprises SEQ ID NO: 1 (5' ITR), SEQ ID NO: 16 (E-SARE), SEQ ID NO: 7 (BDNF), SEQ ID NO: 9 (bGH polyadenylation sequence) and SEQ ID NO: 2 (3' ITR).

In some embodiments, the AAV expression cassette comprises a 5' ITR, a promoter, Kozak sequence, a transgene, and a 3' ITR. In some embodiments, the AAV expression cassette comprises SEQ ID NO: 1 (5' ITR), SEQ ID NO: 6 (hSARE-ArcMin), SEQ ID NO: 14 or 15 (Kozak sequence), SEQ ID NO: 7 (BDNF), and SEQ ID NO: 2 (3' ITR). In some embodiments, the AAV expression cassette comprises SEQ ID NO: 1 (5' ITR), SEQ ID NO: 16 (E-SARE), SEQ ID NO: 14 or 15 (Kozak sequence), SEQ ID NO: 7 (BDNF), and SEQ ID NO: 2 (3' ITR).

In some embodiments, the AAV expression cassette comprises a 5' ITR, a promoter, Kozak sequence, a transgene, a polyadenylation sequence and a 3' ITR. In some embodiments, the AAV expression cassette comprises SEQ ID NO: 1 (5' ITR), SEQ ID NO: 6 (hSARE-ArcMin), SEQ ID NO: 14 or 15 (Kozak sequence), SEQ ID NO: 7 (BDNF), SEQ ID NO: 9 (bGH polyadenylation sequence) and SEQ ID NO: 2 (3' ITR). In some embodiments, the AAV expression cassette comprises SEQ ID NO: 1 (5' ITR), SEQ ID NO: 16 (E-SARE), SEQ ID NO: 14 or 15 (Kozak sequence), SEQ ID NO: 7 (BDNF), SEQ ID NO: 9 (bGH polyadenylation sequence) and SEQ ID NO: 2 (3' ITR).

In some embodiments, the AAV expression cassette comprises a 5' ITR, a promoter, a transgene, a 3' UTR and a 3' ITR. In some embodiments, the AAV expression cassette comprises SEQ ID NO: 1 (5' ITR), SEQ ID NO: 6 (hSARE-ArcMin), SEQ ID NO: 7 (BDNF), SEQ ID NO: 8 (BDNF short 3'UTR), and SEQ ID NO: 2 (3' ITR). In some embodiments, the AAV expression cassette comprises SEQ ID NO: 1 (5' ITR), SEQ ID NO: 16 (E-SARE), SEQ ID NO: 7 (BDNF), SEQ ID NO: 8 (BDNF short 3'UTR), and SEQ ID NO: 2 (3' ITR). In some embodiments, the AAV expression cassette comprises SEQ ID NO: 1 (5' ITR), SEQ ID NO: 6 (hSARE-ArcMin), SEQ ID NO: 7 (BDNF), SEQ ID NO: 10 (BDNF long 3'UTR), and SEQ ID NO: 2 (3' ITR). In some embodiments, the AAV expression cassette comprises SEQ ID NO: 1 (5' ITR), SEQ ID NO: 16 (E-SARE), SEQ ID NO: 7 (BDNF), SEQ ID NO: 10 (BDNF long 3'UTR), and SEQ ID NO: 2 (3' ITR).

In some embodiments, the AAV expression cassette comprises a 5' ITR, a promoter, a transgene, a 3' UTR, a polyadenylation sequence and a 3' ITR. In some embodiments, the AAV expression cassette comprises SEQ ID NO: 1 (5' ITR), SEQ ID NO: 6 (hSARE-ArcMin), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR). In some embodiments, the AAV expression cassette comprises SEQ ID NO: 1 (5' ITR), SEQ ID NO: 16 (E-SARE), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR).

In some embodiments, the AAV expression cassette comprises a 5' ITR, a promoter, Kozak sequence, a transgene, a 3' UTR and a 3' ITR. In some embodiments, the AAV expression cassette comprises SEQ ID NO: 1 (5' ITR), SEQ ID NO: 6 (hSARE-ArcMin), SEQ ID NO: 14 or 15 (Kozak sequence), SEQ ID NO: 7 (BDNF), SEQ ID NO: 8 or 10 (BDNF short or long 3'UTR), and SEQ ID NO: 2 (3' ITR). In some embodiments, the AAV expression cassette comprises SEQ ID NO: 1 (5' ITR), SEQ ID NO: 16 (E-SARE), SEQ ID NO: 14 or 15 (Kozak sequence), SEQ ID NO: 7 (BDNF), SEQ ID NO: 8 or 10 (BDNF short or long 3'UTR), and SEQ ID NO: 2 (3' ITR).

In some embodiments, the AAV expression cassette comprises a 5' ITR, a promoter, a Kozak sequence, a transgene, a 3' UTR, a polyadenylation sequence and a 3' ITR. In some embodiments, the AAV expression cassette comprises SEQ ID NO: 1 (5' ITR), SEQ ID NO: 6 (hSARE-ArcMin), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR). In some embodiments, the AAV expression cassette comprises SEQ ID NO: 1 (5' ITR), SEQ ID NO: 16 (E-SARE), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR).

In some embodiments, the AAV expression cassette comprises a 5' ITR, a stuffer sequence, a promoter, a Kozak sequence, a transgene, a 3' untranslated region (3' UTR), a polyadenylation sequence, and a 3' ITR. In some embodiments, the AAV expression cassette comprises SEQ ID NO: 1 (5' ITR), SEQ ID NO: 13 (stuffer sequence), SEQ ID NO: 6 (hSARE-ArcMin), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR). In some embodiments, the AAV expression cassette comprises SEQ ID NO: 1 (5' ITR), SEQ ID NO: 13 (stuffer sequence), SEQ ID NO: 16 (E-SARE), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence) and SEQ ID NO: 2 (3' ITR).

In some embodiments, the AAV expression cassette comprises a 5' ITR, a promoter, a Kozak sequence, a transgene, a 3' untranslated region (3' UTR), a polyadenylation sequence, a stuffer sequence and a 3' ITR. In some embodiments, the AAV expression cassette comprises SEQ ID NO: 1 (5' ITR), SEQ ID NO: 6 (hSARE-ArcMin), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence), SEQ ID NO: 13 (stuffer sequence), and SEQ ID NO: 2 (3' ITR). In some embodiments, the AAV expression cassette comprises SEQ ID NO: 1 (5' ITR), SEQ ID NO: 13 (stuffer sequence), SEQ ID NO: 16 (E-SARE), SEQ ID NO: 14 or 15 (Kozak sequence), SEQ ID NO: 7 (BDNF), SEQ ID NO: 8 or 10 (BDNF short or long 3'UTR), SEQ ID NO: 9 (bGH polyadenylation sequence), SEQ ID NO: 13 (stuffer sequence), and SEQ ID NO: 2 (3' ITR).

AAV Production Methods

The AAV expression cassettes described herein may be incorporated into a vector (e.g., a plasmid or a bacmid) using standard molecular biology techniques. The disclosure provides vectors comprising any one of the AAV expression cassettes described herein. The vector (e.g., plasmid or bacmid) may further comprise one or more genetic elements used during production of AAV, including, for example, AAV rep and cap genes, and helper virus protein sequences.

The AAV expression cassettes, and vectors (e.g., plasmids) comprising the AAV expression cassettes described herein may be used to produce recombinant AAV vectors.

The disclosure provides methods for producing a recombinant AAV vector comprising contacting an AAV producer cell (e.g., an HEK293 cell) with an AAV expression cassette, or vector (e.g., plasmid) of the disclosure. The disclosure further provides cells comprising any one of the AAV expression cassettes, or vectors disclosed herein. In some embodiments, the method further comprises contacting the AAV producer cell with one or more additional plasmids encoding, for example, AAV rep and cap genes, and helper virus protein sequences. In some embodiments, a method for producing a recombinant AAV vector comprises contacting an AAV producer cell (e.g., an insect cell such as a Sf9 cell) with at least one insect cell-compatible vector comprising an AAV expression cassette of the disclosure. An "insect cell-compatible vector" is any compound or formulation (biological or chemical), which facilitates transformation of or transfection of an insect cell with a nucleic acid. In some embodiments, the insect cell-compatible vector is a baculoviral vector. In some embodiments, the method further comprises maintaining the insect cell under conditions such that AAV is produced.

The disclosure provides recombinant AAV vectors produced using any one of the methods disclosed herein. The recombinant AAV vectors produced may be of any serotype, for example AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

In some embodiments, the recombinant AAV vectors produced may comprise one or more amino acid modifications (e.g., substitutions and/or deletions) compared to the native AAV capsid. For example, the recombinant AAV vectors may be modified AAV vectors derived from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV. In some embodiments, the recombinant AAV vector is a single-stranded AAV (ssAAV). In some embodiments, the recombinant AAV vector is a self-complementary AAV (scAAV).

In some embodiments, the AAV vector comprises a capsid protein of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the AAV vector comprises a capsid protein with one or more substitutions or mutations, as compared to a wild type AAV capsid protein. The recombinant AAV vectors disclosed herein may be used to transduce target cells with the transgene sequence, for example by contacting the recombinant AAV vector with a target cell.

Methods of Expression and Treatment

The disclosure provides compositions comprising any one of the nucleic acids, AAV expression cassettes, plasmids, cells, or recombinant AAV vectors disclosed herein. In some embodiments, the compositions disclosed herein comprise at least one pharmaceutically acceptable carrier, excipient, and/or vehicle, for example, solvents, buffers, solutions, dispersion media, coatings, antibacterial and antifungal agents, isotonic and absorption delaying agents. In some embodiments, the pharmaceutically acceptable carrier, excipient, and/or vehicle may comprise saline, buffered saline, dextrose, water, glycerol, sterile isotonic aqueous buffer, and combinations thereof. In some embodiments, the pharmaceutically acceptable carrier, excipient, and/or vehicle comprises phosphate buffered saline, sterile saline, lactose, sucrose, calcium phosphate, dextran, agar, pectin, peanut oil, sesame oil, pharmaceutical grades of mannitol, lactose, starch, magnesium stearate, sodium saccharine, cellulose, magnesium carbonate, polyol (e.g., glycerol, propylene glycol, and liquid polyethylene glycol, and the like) or suitable mixtures thereof. In some embodiments, the compositions disclosed herein further comprise minor amounts of emulsifying or wetting agents, or pH buffering agents.

In some embodiments, the compositions disclosed herein further comprise other conventional pharmaceutical ingredients, such as preservatives, or chemical stabilizers, such as chlorobutanol, potassium sorbate, sorbic acid, sulfur dioxide, propyl gallate, the parabens, ethyl vanillin, glycerin, phenol, parachlorophenol or albumin. In some embodiments, the compositions disclosed herein may further comprise antibacterial and antifungal agents, such as, parabens, chlorobutanol, phenol, sorbic acid or thimerosal; isotonic agents, such as, sugars or sodium chloride and/or agents delaying absorption, such as, aluminum monostearate and gelatin.

The disclosure provides methods of delivering a Rett Syndrome-associated gene into a cell by contacting the cell with any one of the any one of the nucleic acids, AAV expression cassettes, plasmids, recombinant AAV vectors, or compositions disclosed herein. In some embodiments, the cell is a dividing cell, such as a cultured cell in cell culture. In some embodiments, the cell is a non-dividing cell. In some embodiments, the Rett Syndrome-associated gene is delivered to the cell in vitro, e.g., to produce the Rett Syndrome-associated polypeptide in vitro or for ex vivo gene therapy.

In some embodiments, the Rett Syndrome-associated gene is delivered to a subject in need thereof, e.g., to express an immunogenic or therapeutic polypeptide. In this manner, the polypeptide or functional RNA can be produced in vivo in the subject. Thus, the disclosure provides methods of expressing a Rett-syndrome-associated gene in a subject in need thereof, comprising administering to the subject a therapeutically effective amount of any one of the nucleic acids, AAV expression cassettes, plasmids, cells, recombinant AAV vectors, or compositions disclosed herein. The disclosure also provides methods for treating and/or delaying the onset of at least one symptom of Rett Syndrome in a subject. In some embodiments, the methods comprise administering to the subject a therapeutically effective amount of any one of the nucleic acid of any one of the nucleic acids, AAV expression cassettes, plasmids, cells, recombinant AAV vectors, or compositions disclosed herein. In some embodiments, the subject has Rett Syndrome. In some embodiments, the subject has a high risk of developing Rett Syndrome; for example, the subject is a newborn who is identified as carrying a mutation in the mecp2 gene. In some embodiments, the Rett-syndrome-associated gene is targeted by gene therapy to increase its expression and/or function. In some embodiments, the Rett-syndrome-associated gene is targeted by gene therapy to decrease its expression and/or function.

The disclosure provides methods of treating and/or delaying the onset of a MECP2-associated disease in a subject, comprising administering to the subject a therapeutically effective amount of any one of the nucleic acids, AAV expression cassettes, plasmids, cells, recombinant AAV vectors, or compositions disclosed herein. As used herein, a "MECP2-associated disease" is a disease which is correlated with, or caused by, genetic changes (for example, one or more deletions, insertions, duplications and/or substitutions) to the mecp2 gene, as compared to the wild type mecp2 gene, and/or alterations to the expression and/or activity of the MECP2 protein, as compared with a wild type MECP2 protein.

In some embodiments, the MECP2-associated disease is MECP2 duplication syndrome, MECP2-related severe neonatal encephalopathy, PPM-X syndrome, or Rett syndrome. MECP2 duplication syndrome is caused by duplication of the MECP2 gene, and is characterized by intellectual disability, delayed development, and seizures. Duplication of the MECP2 gene leads to the production of extra MECP2 protein and an increase in protein function, leading to abnormal neuronal function. MECP2-related severe neonatal encephalopathy is caused by mutations in the mecp2 gene, most of which are single base pair insertions, deletions or substitutions. This condition almost exclusively affects males, and is characterized by small head size (microcephaly), movement disorders, breathing problems, and seizures. Mutations in the mecp2 gene can alter the structure of the MECP2 protein or reduce the amount of protein that is produced. PPM-X syndrome is a disease characterized by mild to severe intellectual disability, bipolar disorder, and a pattern of movement abnormalities. Approximately half of all cases of PPM-X syndrome are caused by one of eight mutations in mecp2 gene. These mutations either cause insertions, deletions or substitutions of amino acids in the MECP2 protein, or create a premature stop signal in mecp2 mRNA.

The disclosure further provides methods of treating and/or delaying the onset of a BDNF-associated disease in a subject, comprising administering to the subject a therapeutically effective amount of any one of the nucleic acids, AAV expression cassettes, plasmids, cells, recombinant AAV vectors, or compositions disclosed herein. As used herein, a "BDNF-associated disease" is a disease which is correlated with, or caused by, genetic changes to the bdnf gene, and/or changes to the expression and/or activity of the BDNF protein. In some embodiments, the BDNF-associated disease is a cognitive disorder, and/or a stress-related disorder. In some embodiments, the BDNF-associated disease is depression, obsessive-compulsive disorder, Alzheimer's disease, Huntington's disease, dementia, anorexia nervosa, bulimia nervosa, schizophrenia, epilepsy, post-traumatic stress disorder, bipolar disease, Rett Syndrome, major depressive disorder, or post-chemotherapy cognitive impairment.

In some embodiments, the Rett Syndrome-associated gene is expressed in the neurons of the subject. In some embodiments, the level of expression of the Rett Syndrome-associated gene is higher in neurons than in non-neuronal cells of the body. In some embodiments, the expression of the Rett Syndrome-associated gene is not detectable in non-neuronal cells. In some embodiments, the level of expression of the Rett Syndrome-associated gene is higher in neurons by at least about 1.2 fold (for example, about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 15 fold, about 20 fold, about 30 fold, about 40 fold, about 50 fold, about 60 fold, about 70 fold, about 80 fold about 90 fold, or about 100 fold, including all values and subranges that lie therebetween) relative to that in non-neuronal cells of the body.

In some embodiments, the neurons are active neurons. In some embodiments, the level of expression of the Rett Syndrome-associated gene is higher in active neurons than in resting neurons of the body. In some embodiments, the expression of the Rett Syndrome-associated gene is not detectable in resting neurons. In some embodiments, the level of expression of the Rett Syndrome-associated gene is higher in active neurons by at least about 1.2 fold (for example, about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 15 fold, about 20 fold, about 30 fold, about 40 fold, about 50 fold, about 60 fold, about 70 fold, about 80 fold about 90 fold, or about 100 fold, including all values and subranges that lie therebetween) relative to that in resting neurons.

In some embodiments, the Rett Syndrome-associated gene is expressed in the central nervous system (CNS) neurons of the subject. In some embodiments, the level of expression of the Rett Syndrome-associated gene is higher in CNS neurons by at least about 1.2 fold (for example, about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 15 fold, about 20 fold, about 30 fold, about 40 fold, about 50 fold, about 60 fold, about 70 fold, about 80 fold about 90 fold, or about 100 fold, including all values and subranges that lie therebetween) relative to that in non-neuronal cells of the body.

In some embodiments, the level of expression of the Rett Syndrome-associated gene is higher in CNS neurons than in other non-CNS neurons, such as, peripheral nervous system (PNS) neurons of the body. In some embodiments, the expression of the Rett Syndrome-associated gene is not detectable in PNS neurons. In some embodiments, the level of expression of the Rett Syndrome-associated gene is higher in CNS neurons by at least about 1.2 fold (for example, about 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 15 fold, about 20 fold, about 30 fold, about 40 fold, about 50 fold, about 60 fold, about 70 fold, about 80 fold about 90 fold, or about 100 fold, including all values and subranges that lie therebetween) relative to that in other non-CNS neurons, such as, peripheral nervous system (PNS) neurons of the body.

Dosages of the recombinant AAV vector to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, about $10^6$, about $10^7$, about $10^8$, about $10^9$, about $10^{10}$, about $10^{11}$, about $10^{12}$, about $10^{13}$, about $10^{14}$, about $10^{15}$ transducing units, optionally about $10^8$ to about $10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). In some embodiments, the administration is by injection into the central nervous system. The most suitable route in any given case will depend on the nature and severity of the condition being treated and/or prevented and on the nature of the particular vector that is being used.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid.

In some embodiments, the methods disclosed herein may comprise administering to the subject a therapeutically effective amount of any one of the nucleic acids, AAV expression cassettes, plasmids, cells, recombinant AAV vectors, or compositions disclosed herein in combination with one or more secondary therapies targeting Rett syndrome. In some embodiments, the methods of treating and/or delaying the onset of at least one symptom of Rett Syndrome in a subject disclosed herein may further comprise administering one or more secondary therapies targeting Rett syndrome. In some embodiments, the secondary therapy comprises administration of glatiramer acetate. Further details regarding the use of glatiramer acetate are provided in Djukic A et al., *Pediatr Neurol.* 2016 August; 61:51-7, the contents of which are incorporated herein by reference in its entirety.

In some embodiments, the secondary therapy comprises: administration of a drug to treat seizures, administration of a drug to treat reflux, or a combination thereof. In some embodiments, the secondary therapy comprises administration of a drug to treat seizures. Non-limiting examples of drugs to treat seizures include levetiracetam, valproic acid, oxcarbazepine, and lamotrigine. In some embodiments, the secondary therapy comprises administration of a drug to treat reflux. Non-limiting examples of drugs to treat reflux include H2 blockers, such as, cimetidine, ranitidine, nizatidine, and famotidine; proton pump inhibitors, such as, omeprazole, esomeprazole, lansoprazole, rabeprazole, pantoprazole, and dexlansoprazole; and motility agents, such as, low-dose erythromycin, benzamide, domperidone, and linaclotide.

The term administered "in combination," as used herein, is understood to mean that two (or more) different treatments are delivered to the subject during the course of the subject's affliction with the disorder (such as, Rett syndrome), such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent" delivery. In other embodiments, the delivery of one treatment ends before the delivery of the other treatment begins, which may be referred to as "sequential" delivery.

In some embodiments, the treatment is more effective because of combined administration. For example, the second treatment is more effective; for e.g., an equivalent effect is seen with less of the second treatment, or the second treatment reduces symptoms to a greater extent, than would be seen if the second treatment were administered in the absence of the first treatment, or the analogous situation is seen with the first treatment. The effect of the two treatments can be partially additive, wholly additive, or greater than additive (synergistic).

All papers, publications and patents cited in this specification are herein incorporated by reference as if each individual paper, publication or patent were specifically and individually indicated to be incorporated by reference and are incorporated herein by reference to disclose and describe the methods and/or materials in connection with which the publications are cited. However, mention of any reference, article, publication, patent, patent publication, and patent application cited herein is not, and should not be taken as an acknowledgment or any form of suggestion that they constitute valid prior art or form part of the common general knowledge in any country in the world.

Unless the context indicates otherwise, it is specifically intended that the various features described herein can be used in any combination.

Unless otherwise defined, all technical and scientific terms used herein have the same meaning as commonly understood by one of ordinary skill in the art to which this disclosure belongs.

It is to be understood that the description above as well as the examples that follow are intended to illustrate, and not limit, the scope of the invention. Other aspects, advantages and modifications within the scope of the invention will be apparent to those skilled in the art to which the invention pertains.

EXAMPLES

The following examples, which are included herein for illustration purposes only, are not intended to be limiting.

Example 1: Preparation of AAV Expression Cassettes

Figure 2:
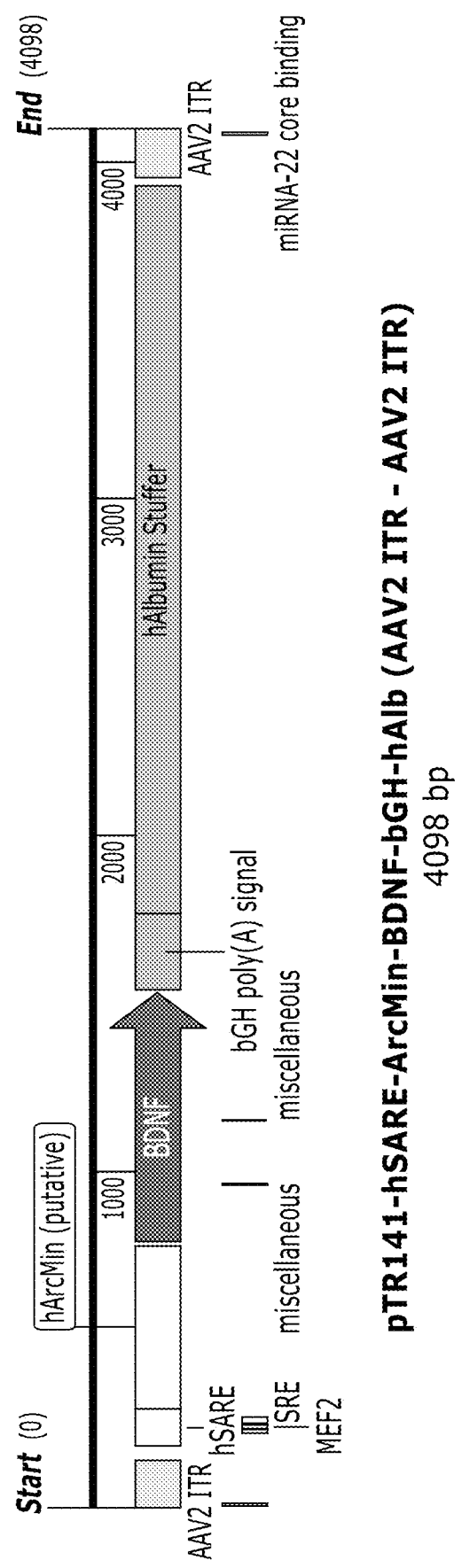
FIG. 2 shows an AAV expression cassette, comprising the hSARE-hArcMin promoter (SEQ ID NO: 6), BDNF gene (SEQ ID NO: 7), bGH polyA signal (SEQ ID NO: 9) and a stuffer sequence (SEQ ID NO: 13), all of which are flanked by a 5' ITR (SEQ ID NO: 1) and a 3' ITR (SEQ ID NO: 2).
Figure 3:
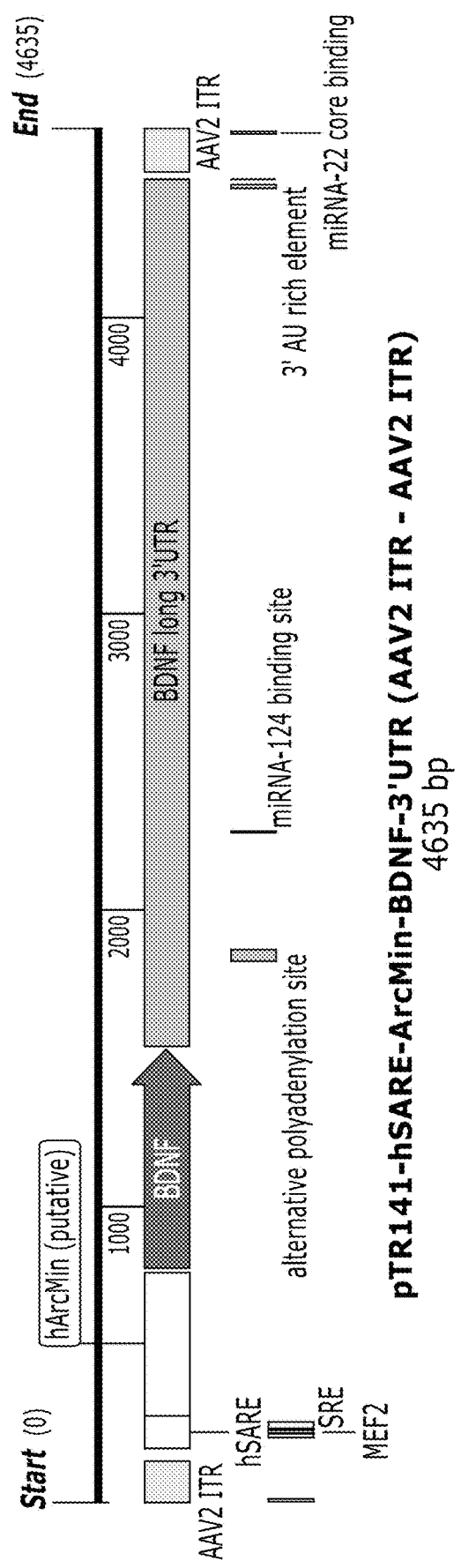
FIG. 3 shows an AAV expression cassette, comprising the hSARE-hArcMin promoter (SEQ ID NO: 6), BDNF gene (SEQ ID NO: 7), and BDNF long 3' UTR (SEQ ID NO: 10), all of which are flanked by a 5' ITR (SEQ ID NO: 1) and a 3' ITR (SEQ ID NO: 2).
Figure 4:
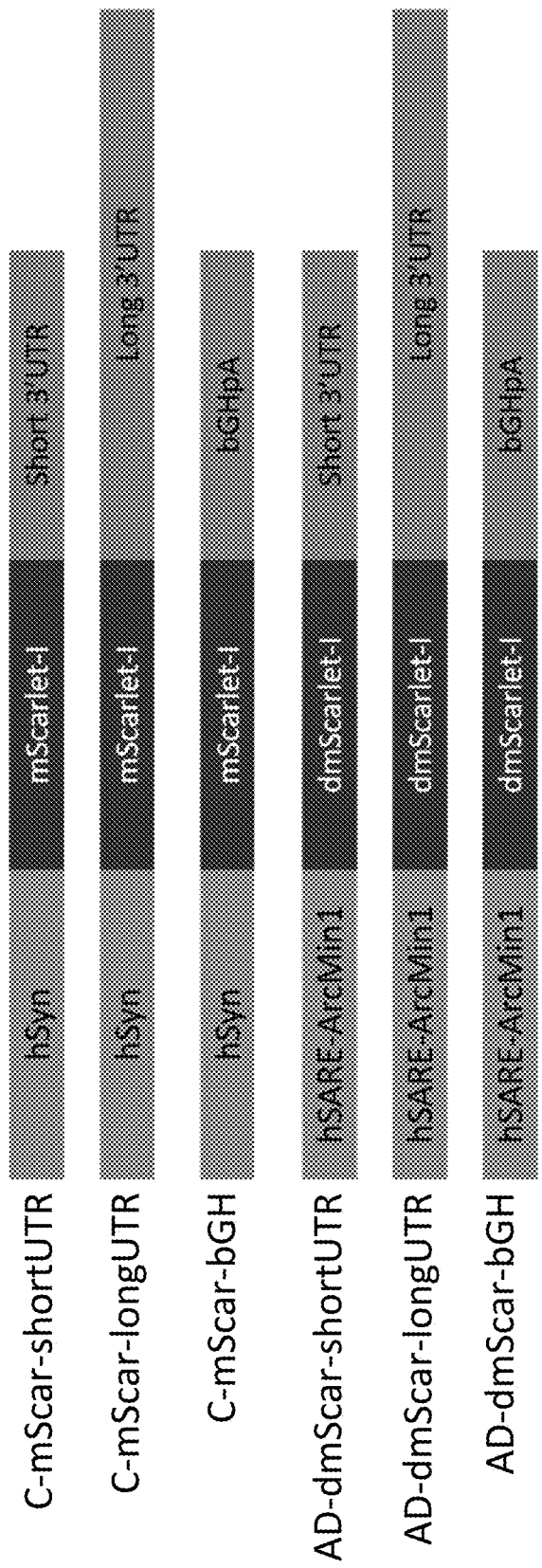
FIG. 4 shows the schematic representations of AAV expression cassettes for reporter gene expression comprising a constitutive ("C") promoter, hSyn or an activity-dependent ("AD") promoter, hSARE-hArcMin. The elements of the expression cassettes are also listed in Table 3.

Three AAV expression cassettes comprising the activity-dependent hSARE-hArcMin promoter (SEQ ID NO: 6) and BDNF gene (SEQ ID NO: 7), flanked by 5' ITR (SEQ ID NO: 1) and 3' ITR (SEQ ID NO: 2), were generated using standard cloning techniques. See FIGS. 1-3 showing a schematic representation of the three cassettes. The first cassette comprises the BDNF short 3' UTR (SEQ ID NO: 8) and a stuffer sequence (SEQ ID NO: 13). The second cassette comprises a bGH polyA signal (SEQ ID NO: 9) and a stuffer sequence (SEQ ID NO: 13). The third cassette comprises the BDNF long 3' UTR (SEQ ID NO: 10). The three AAV expression cassettes comprise the nucleic acid sequences of SEQ ID NO: 3 (FIG. 1), SEQ ID NO: 4 (FIG. 2), and SEQ ID NO: 5 (FIG. 3), respectively.

Example 2: Preparation of Recombinant AAV Vectors in Mammalian Cells

Each of the three AAV expression cassettes is incorporated into a plasmid, to give three plasmids comprising each of the three AAV expression cassettes. Each of the three plasmids is transfected into viral production cells (e.g., HEK293) using an appropriate transfection reagent (e.g., Lipofectamine™), along with a Rep/Cap plasmid encoding the Rep and Cap genes, and a helper plasmid comprising various helper sequences required for AAV production (E4, E2a and VA). After incubation at 37°C for a predetermined period of time, AAV particles are collected from the media or the cells are lysed to release the AAV particles. The AAV particles are then purified and titered, and may be stored at −80° C. for later use.

Example 3: Preparation of Recombinant AAV Vectors in Insect Cells

Each of the three AAV expression cassettes are incorporated into a baculoviral vector, to give three baculoviral vectors comprising each of the three AAV expression cassettes. Insect cells (e.g., Sf9) are co-infected in suspension culture with each of the three baculoviral vectors, and least one additional recombinant baculoviral vector comprising sequences encoding the AAV Rep and Cap proteins. After incubation at 28° C. for a predetermined period of time, AAV particles are collected from the media or the cells are lysed to release the AAV particles. The AAV particles are then purified and titered, and may be stored at −80° C. for later use.

Example 4: hSARE-hArcMin Promoter Drives Activity-Dependent Reporter Gene Expression To test whether the hSARE-hArcMin promoter is able to drive gene expression in a manner dependent on neuronal activity, the following experiments were performed.

AAV expression cassettes comprising a constitutive promoter that drives long term expression in neurons (hSyn; human synapsin 1 gene promoter, comprising the nucleic acid sequence of SEQ ID NO: 38) or an activity-dependent promoter (hSARE-hArcMin, SEQ ID NO: 6) were generated using standard cloning techniques (see Table 3). FIGS. 4, 9A-9C, 10A-10C, and 11A-11C show the schematic representation of these cassettes. The cassettes comprise one of the following 3'UTR sequences: a BDNF short 3' UTR (SEQ ID NO: 8), a bGH poly A signal (referred to as "bGHpA" or "bGH", SEQ ID NO: 9), or a BDNF long 3' UTR (SEQ ID NO: 10). The cassettes also comprise a reporter gene operably linked to the constitutive or activity-dependent promoter. The reporter gene encodes either a monomeric red fluorescent protein (mScarlet, encoded by the nucleic acid sequence of SEQ ID NO: 36), or a destabilized version of mScarlet (dmScarlet, encoded by the nucleic acid sequence SEQ ID NO: 35). The destabilized version of mScarlet comprises a C-terminal PEST degron signal (encoded by the nucleic acid sequence SEQ ID NO: 37), which promotes a faster turnover rate driven by proteasomal degradation, as compared to mScarlet. Therefore, dmScarlet fluorescence accumulates in the cell to a lower extent than mScarlet fluorescence.

TABLE 3

Expression cassettes for reporter gene expression

Figure 9A:
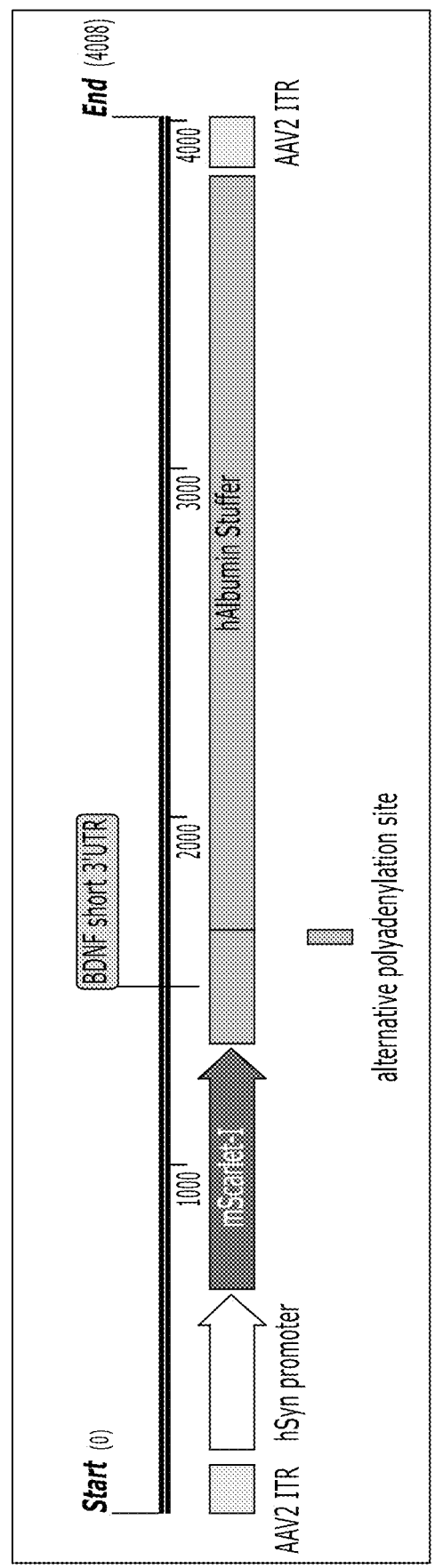
FIG. 9A shows an AAV expression cassette, comprising the nucleic acid sequence of SEQ ID NO: 26, and comprising the following elements: hSyn promoter (SEQ ID NO: 38), mScarlet gene (SEQ ID NO: 36), the BDNF short 3' UTR (SEQ ID NO: 8) and a stuffer sequence (SEQ ID NO: 13), all of which are flanked by a 5' ITR (SEQ ID NO: 1) and a 3' ITR (SEQ ID NO: 2).
Figure 9B:
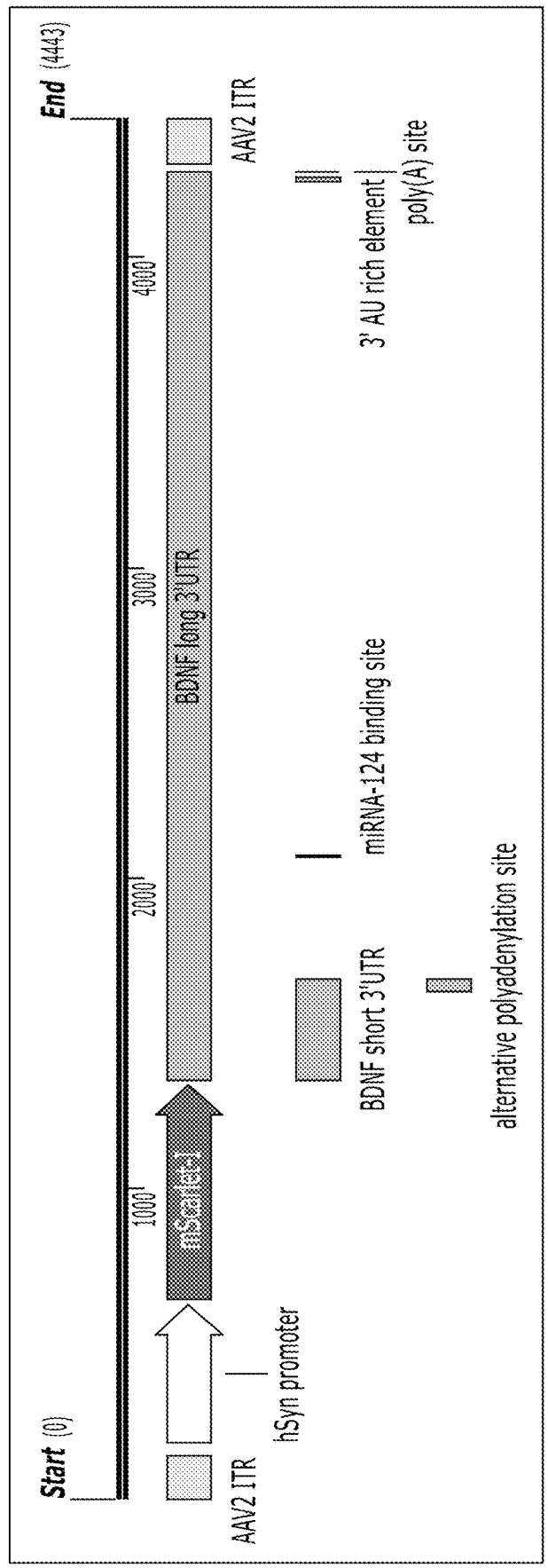
FIG. 9B shows an AAV expression cassette, comprising the nucleic acid sequence of SEQ ID NO: 27, and comprising the following elements: the hSyn promoter (SEQ ID NO: 38), mScarlet gene (SEQ ID NO: 36), and the BDNF long 3' UTR (SEQ ID NO: 10), all of which are flanked by a 5' ITR (SEQ ID NO: 1) and a 3' ITR (SEQ ID NO: 2).
Figure 9C:
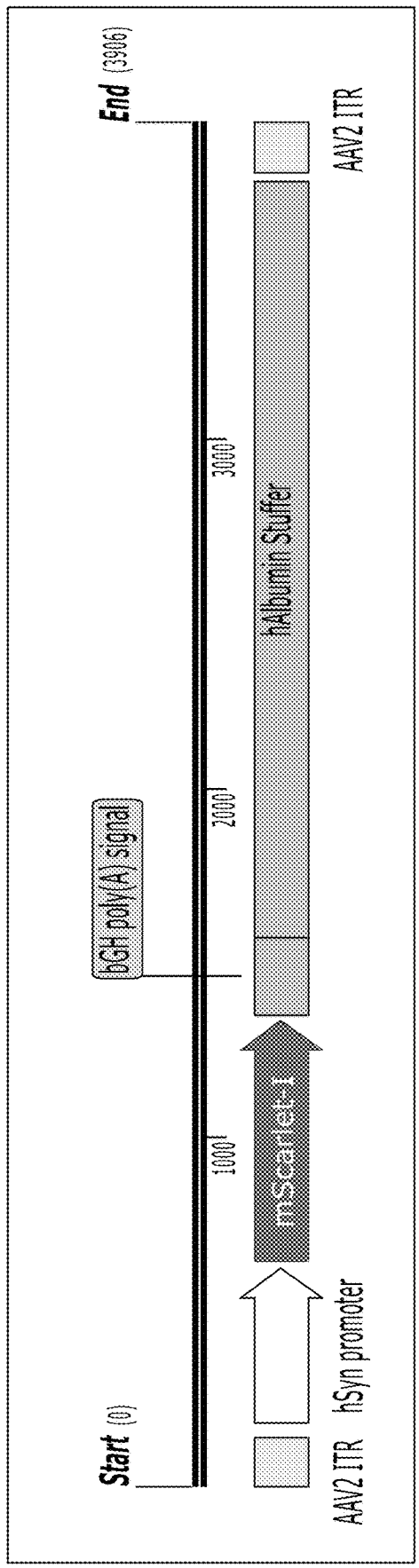
FIG. 9C shows an AAV expression cassette, comprising the nucleic acid sequence of SEQ ID NO: 28, and comprising the following elements: the hSyn promoter (SEQ ID NO: 38), mScarlet gene (SEQ ID NO: 36), the bGH polyA signal (SEQ ID NO: 9) and a stuffer sequence (SEQ ID NO: 13), all of which are flanked by a 5' ITR (SEQ ID NO: 1) and a 3' ITR (SEQ ID NO: 2).
Figure 10A:
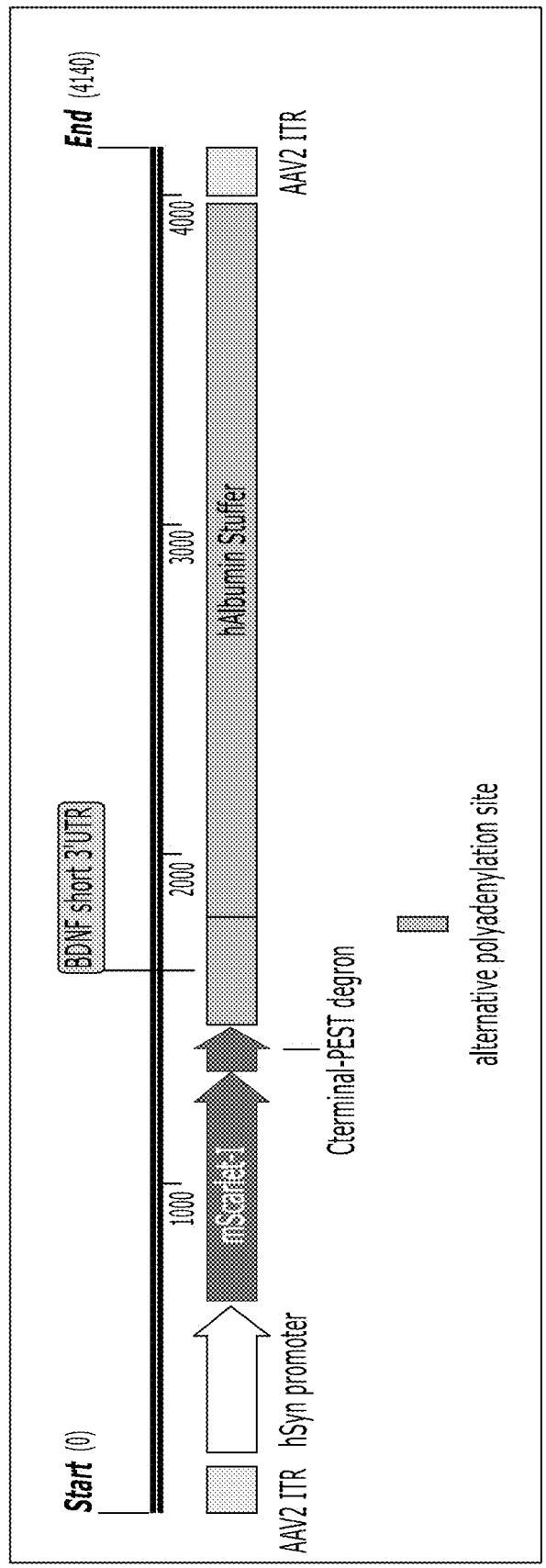
FIG. 10A shows an AAV expression cassette, comprising the nucleic acid sequence of SEQ ID NO: 29, and comprising the following elements: the hSyn promoter (SEQ ID NO: 38), dmScarlet gene (SEQ ID NO: 35), the BDNF short 3' UTR (SEQ ID NO: 8) and a stuffer sequence (SEQ ID NO: 13), all of which are flanked by a 5' ITR (SEQ ID NO: 1) and a 3' ITR (SEQ ID NO: 2).
Figure 10B:
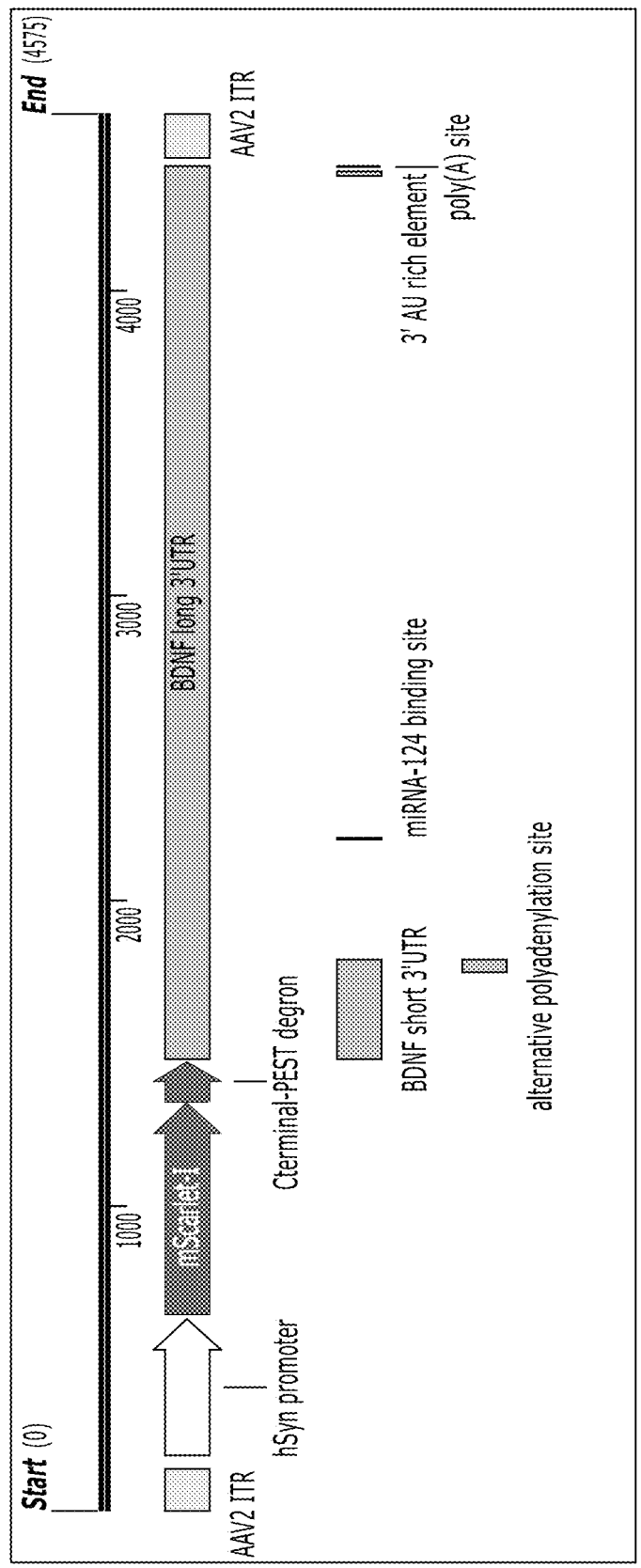
FIG. 10B shows an AAV expression cassette, comprising the nucleic acid sequence of SEQ ID NO: 30, and comprising the following elements: the hSyn promoter (SEQ ID NO: 38), dmScarlet gene (SEQ ID NO: 35), and the BDNF long 3' UTR (SEQ ID NO: 10), all of which are flanked by a 5' ITR (SEQ ID NO: 1) and a 3' ITR (SEQ ID NO: 2).
Figure 10C:
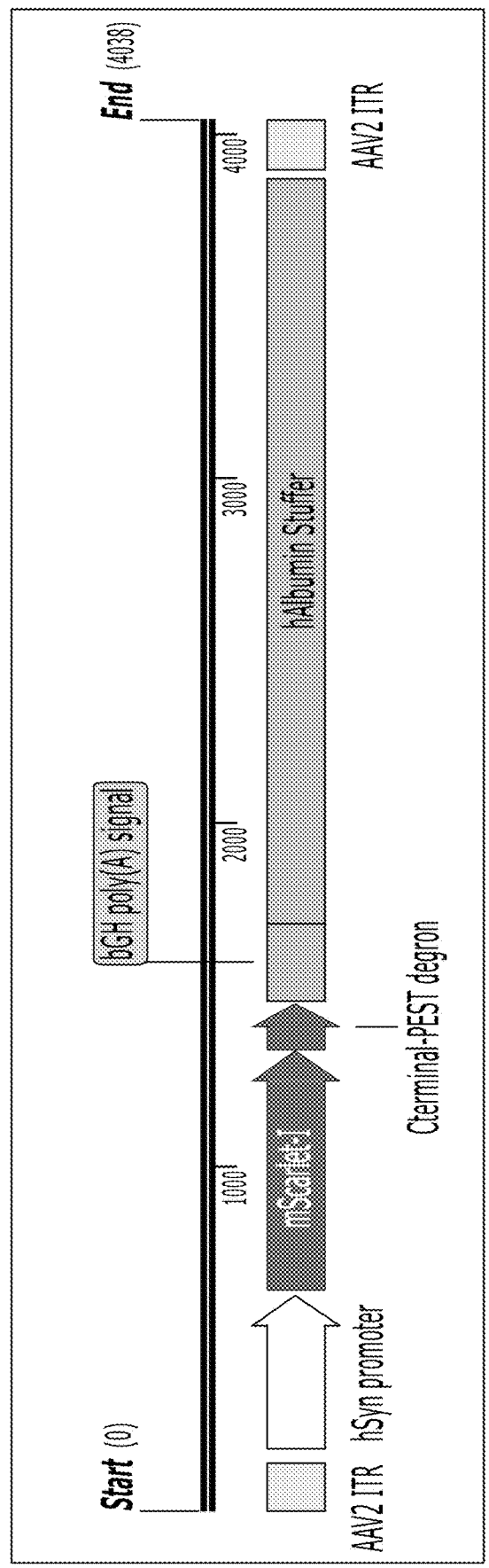
FIG. 10C shows an AAV expression cassette, comprising the nucleic acid sequence of SEQ ID NO: 31, and comprising the following elements: the hSyn promoter (SEQ ID NO: 38), dmScarlet gene (SEQ ID NO: 35), the bGH poly A signal (SEQ ID NO: 9) and a stuffer sequence (SEQ ID NO: 13), all of which are flanked by a 5' ITR (SEQ ID NO: 1) and a 3' ITR (SEQ ID NO: 2).
Figure 11A:
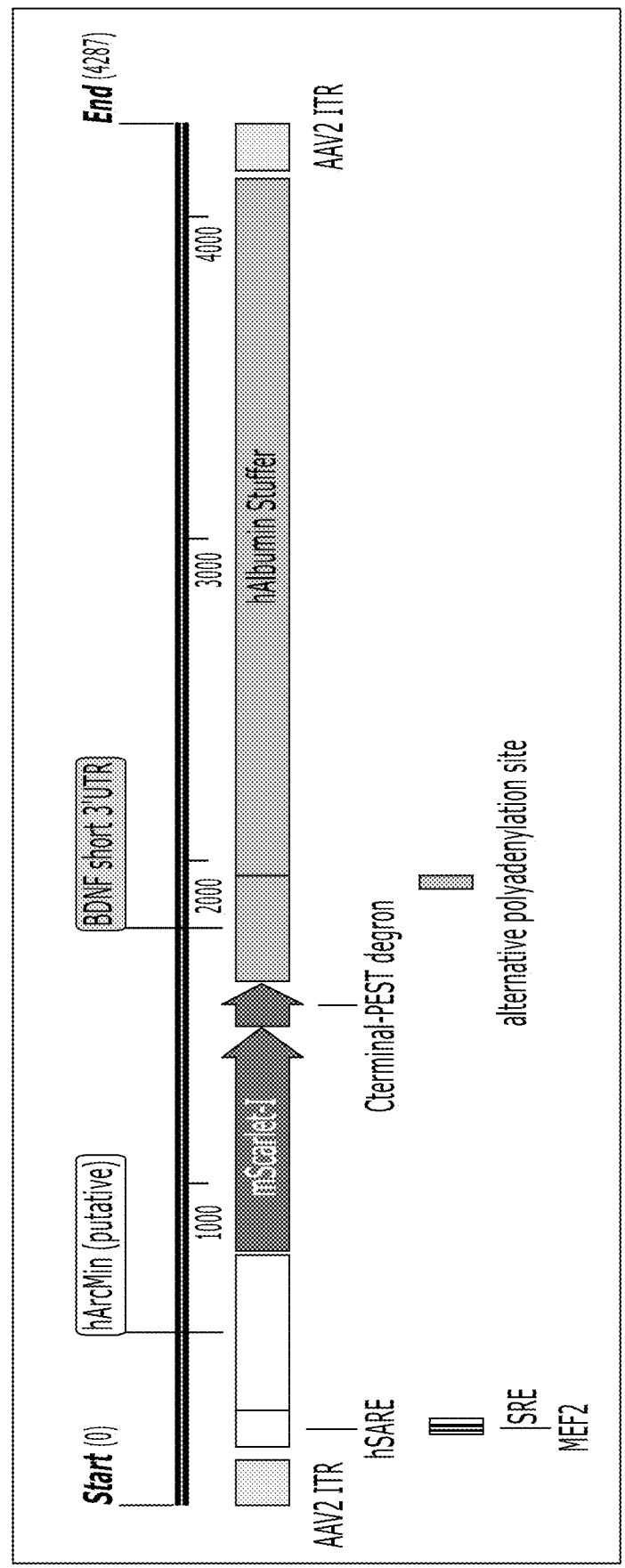
FIG. 11A shows an AAV expression cassette, comprising the nucleic acid sequence of SEQ ID NO: 32, and comprising the following elements: the hSARE-hArcMin promoter (SEQ ID NO: 6), dmScarlet gene (SEQ ID NO: 35), the BDNF short 3' UTR (SEQ ID NO: 8) and a stuffer sequence (SEQ ID NO: 13), all of which are flanked by a 5' ITR (SEQ ID NO: 1) and a 3' ITR (SEQ ID NO: 2).
Figure 11B:
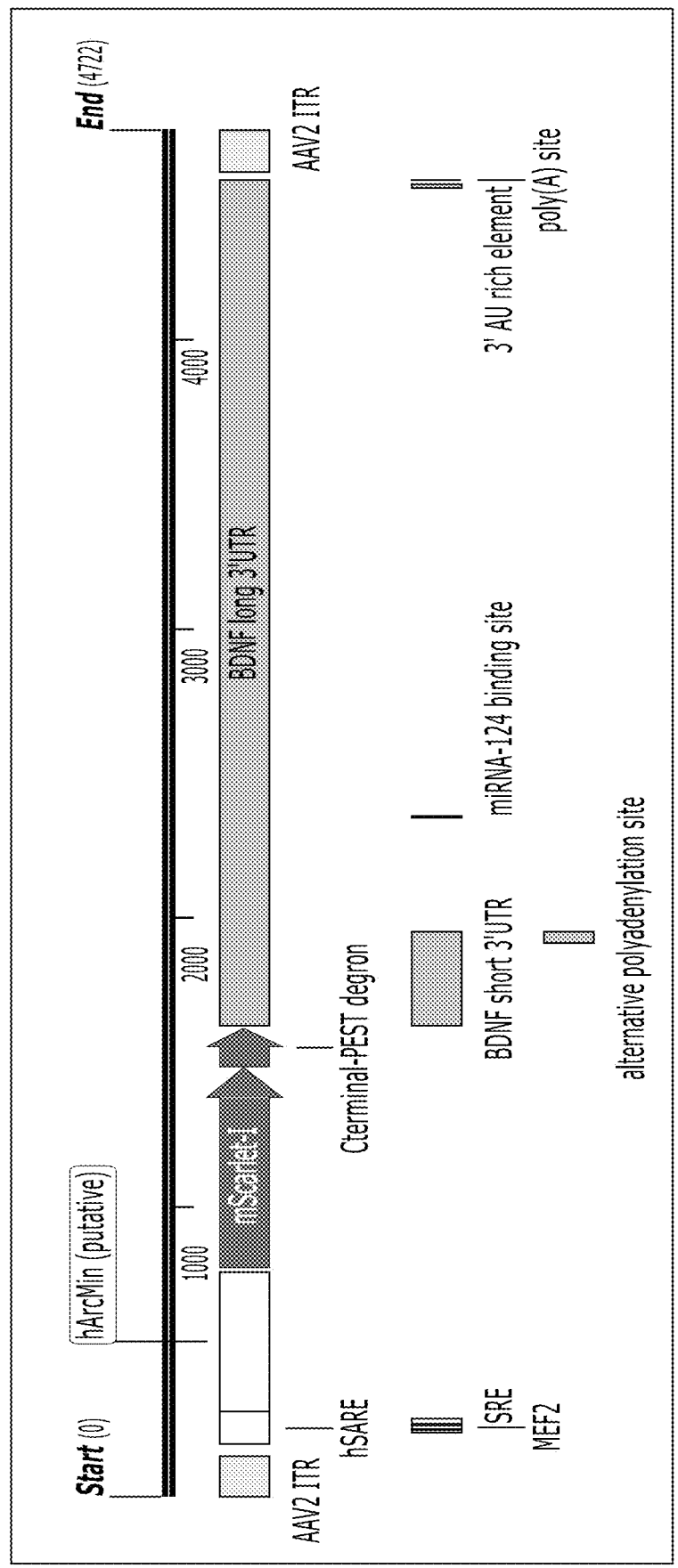
FIG. 11B shows an AAV expression cassette, comprising the nucleic acid sequence of SEQ ID NO: 33, and comprising the following elements: the hSARE-hArcMin promoter (SEQ ID NO: 6), dmScarlet gene (SEQ ID NO: 35), and the BDNF long 3' UTR (SEQ ID NO: 10), all of which are flanked by a 5' ITR (SEQ ID NO: 1) and a 3' ITR (SEQ ID NO: 2).
Figure 11C:
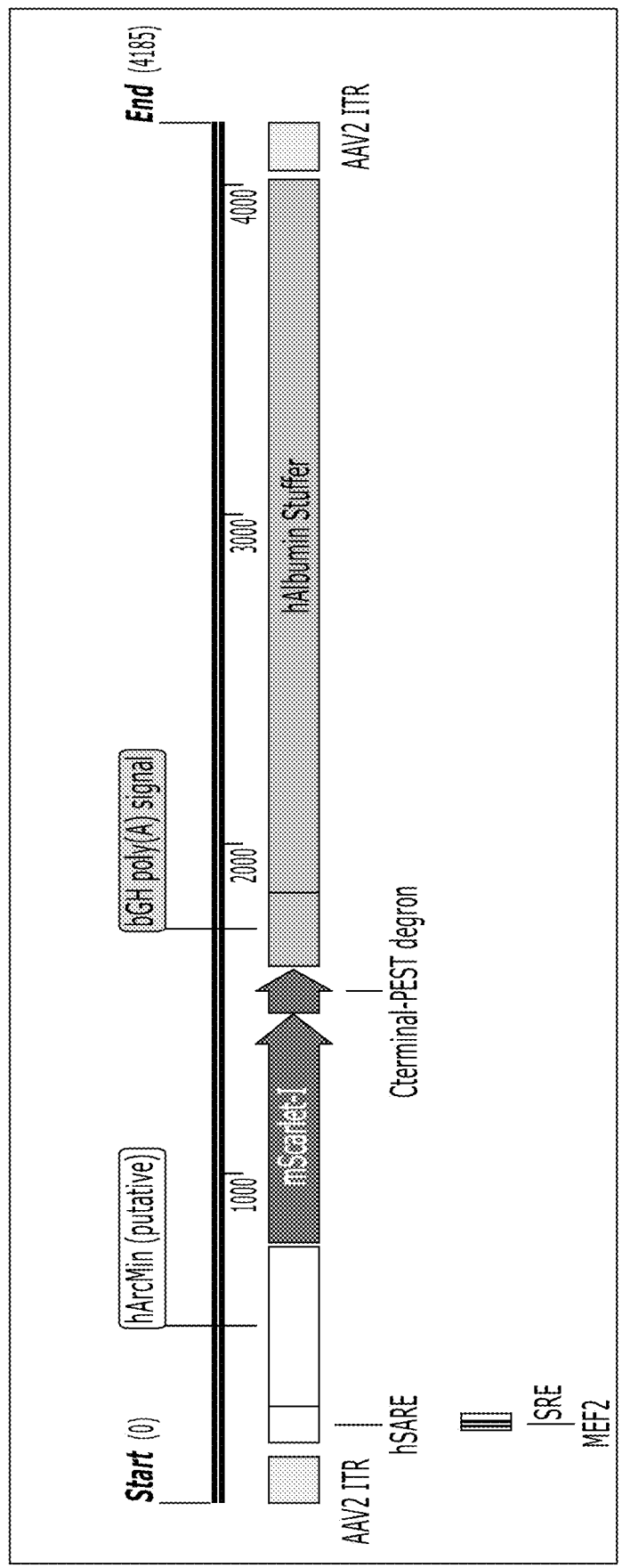
FIG. 11C shows an AAV expression cassette, comprising the nucleic acid sequence of SEQ ID NO: 34, and comprising the following elements: the hSARE-hArcMin promoter (SEQ ID NO: 6), dmScarlet gene (SEQ ID NO: 35), the bGH polyA signal (SEQ ID NO: 9) and a stuffer sequence (SEQ ID NO: 13), all of which are flanked by a 5' ITR (SEQ ID NO: 1) and a 3' ITR (SEQ ID NO: 2).

| Construct No. | Construct Name | SEQ ID NO: | Schematic representation | Promoter | Reporter Gene | Sequence downstream of coding region |
|---|---|---|---|---|---|---|
| 1 | C-mScar-shortUTR | 26 | FIG. 9A | hSyn (Constitutive or "C") | mScarlet-I (mScar) | Short 3'UTR |
| 2 | C-mScar-longUTR | 27 | FIG. 9B | hSyn (Constitutive or "C") | mScarlet-I (mScar) | Long 3'UTR |
| 3 | C-mScar-bGH | 28 | FIG. 9C | hSyn (Constitutive or "C") | mScarlet-I (mScar) | bGHpA |
| 4 | C-dmScar-shortUTR | 26 | FIG. 10A | hSyn (Constitutive or "C") | dmScarlet-I (dmScar) | Short 3'UTR |
| 5 | C-dmScar-longUTR | 27 | FIG. 10B | hSyn (Constitutive or "C") | dmScarlet-I (dmScar) | Long 3'UTR |
| 6 | C-dmScar-bGH | 28 | FIG. 10C | hSyn (Constitutive or "C") | dmScarlet-I (dmScar) | bGHpA |
| 7 | AD-dmScar-shortUTR | 32 | FIG. 11A | hSARE-hArcMin (Activity-dependent or "AD") | dmScarlet-I (dmScar) | Short 3'UTR |
| 8 | AD-dmScar-longUTR | 33 | FIG. 11B | hSARE-hArcMin (Activity-dependent or "AD") | dmScarlet-I (dmScar) | Long 3'UTR |
| 9 | AD-dmScar-bGH | 34 | FIG. 11C | hSARE-hArcMin (Activity-dependent or "AD") | dmScarlet-I (dmScar) | bGHpA |

Recombinant AAV vectors comprising the AAV expression cassettes 1, 2, 3, 7, 8, and 9 listed in Table 3 were prepared as described herein. Wild type mouse primary neurons were transduced with each of these recombinant AAV vectors. The transduced cells were treated with 2 μM of the sodium channel inhibitor, tetrodotoxin (TTX) overnight. Treatment with TTX inhibits neuronal activity. Thereafter, the media was completely aspirated and replaced with any one of the following: (a) media only, (b) media+TTX, (c) media+150 mM KCl, or (d) media+30 µM bicuculine (BIC). While KCl depolarizes neurons, BIC is a competitive antagonist of the γ-Aminobutyric acid type A (GABAA) receptor and induces disinhibition of neurons. Therefore, treating neurons with either KCl or BIC promotes neuronal activity. Control neurons placed in media alone (as per treatment (a) above) are neither inhibited nor activated, and are at rest, while the activity of the neurons placed in media containing TTX (as per treatment (b) above) is inhibited. The cells were further incubated for 2 hours at 37° C. The cells were then fixed and stained with Hoescht 33342, and imaged using a fluorescence microscope.

Figure 5A:
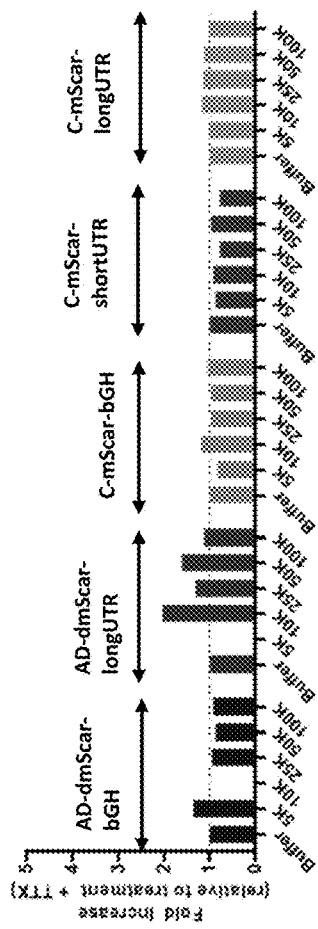
FIG. 5A is a bar graph showing the reporter protein fluorescence in cells that are not treated with tetrodotoxin (TTX), relative to the fluorescence of cells that are treated with 2 M TTX.

FIG. 5A shows the reporter protein fluorescence in cells that are not treated with TTX (that is, cells in which neuronal activity is neither promoted nor inhibited), relative to the fluorescence of cells that are treated with 2 µM TTX, which is normalized to 1. As shown in FIG. 5A, when neuronal activity is neither promoted nor inhibited, the relative fluorescence of cells transduced with AAV vectors that drive dmScarlet expression using the hSARE-hArcMin promoter is comparable to the relative fluorescence of cells transduced with AAV vectors that drive mScarlet expression using the constitutive promoter, hSyn.

Figure 5B:
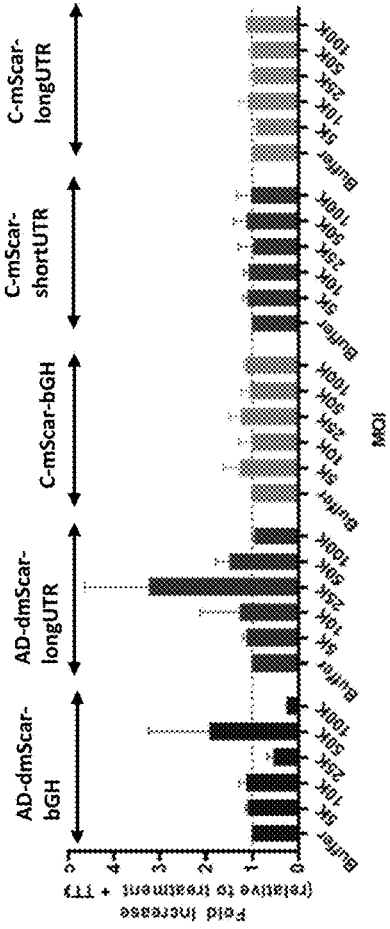
FIG. 5B is a bar graph showing the reporter protein fluorescence in cells that are treated with 150 mM KCl, relative to the fluorescence of cells that are treated with 2 µM TTX.
Figure 5C:
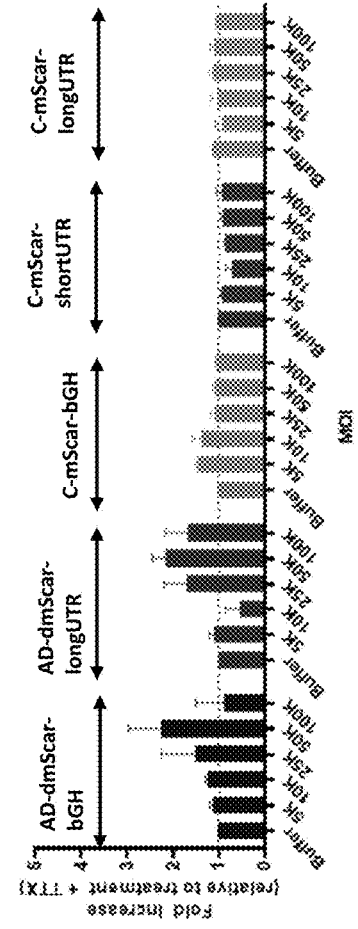
FIG. 5C is a bar graph showing the reporter protein fluorescence in cells that are treated with 30 uM bicuculine (BIC), relative to the fluorescence of cells that are treated with 2 µM TTX. Each of the bars shows the relative fluorescence of cells transduced with AAV vectors comprising the indicated AAV expression cassettes at the multiplicity of infection (MOI) indicated on the X axis.

FIG. 5B shows the reporter protein fluorescence in cells that are not treated with TTX but instead treated with 150 mM KCl (that is, cells in which neuronal activity is promoted), relative to the fluorescence of cells that are treated with 2 µM TTX, which is normalized to 1. FIG. 5C shows the reporter protein fluorescence in cells that are not treated with TTX but instead treated with 30 µM bicuculine (BIC) (that is, cells in which neuronal activity is promoted), relative to the fluorescence of cells that are treated with 2 µM TTX, which is normalized to 1.

As shown in FIGS. 5B and 5C, when neuronal activity is promoted using KCl or BIC treatment, the relative fluorescence of cells transduced with AAV vectors that drive dmScarlet expression using the activity-dependent promoter, hSARE-hArcMin is higher than the relative fluorescence of cells transduced with AAV vectors that drive mScarlet expression using the constitutive promoter (hSyn).

These results demonstrate that the hSARE-hArcMin promoter is able to drive gene expression in a manner dependent on neuronal activity. Furthermore, dmScarlet constructs comprising the bGH or the long 3'UTR were similarly expressed by the hSARE-hArcMin promoter, as shown in FIGS. 5B and 5C.

Figure 6B:
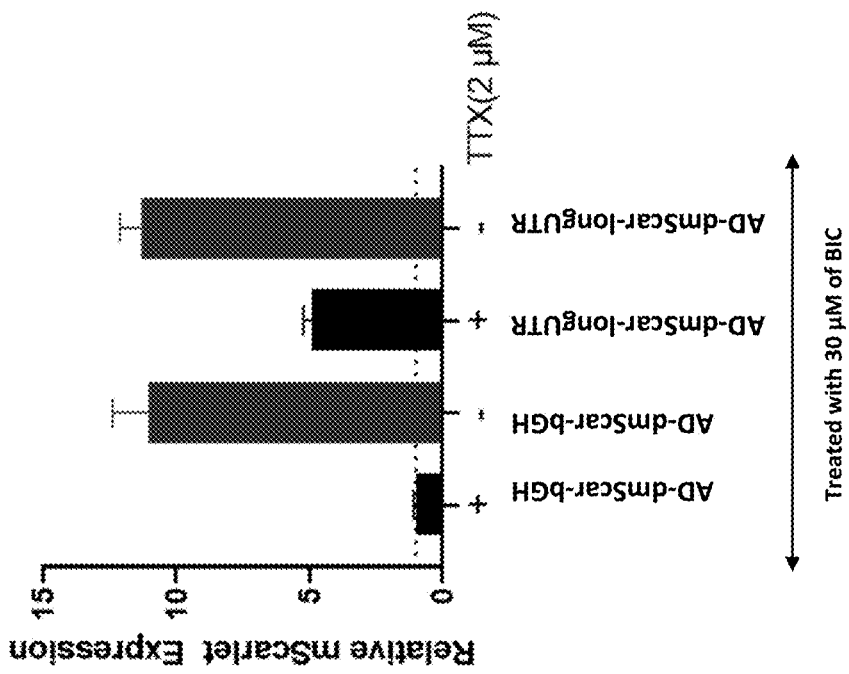
FIG. 6B is a bar graph showing the relative reporter gene expression in cells transduced with AAV vectors comprising the activity-dependent (AD) AAV expression cassettes, which were treated with 30 µM of BIC and further either treated with 2 µM TTX, or left untreated with TTX, as indicated.
Figure 6A:
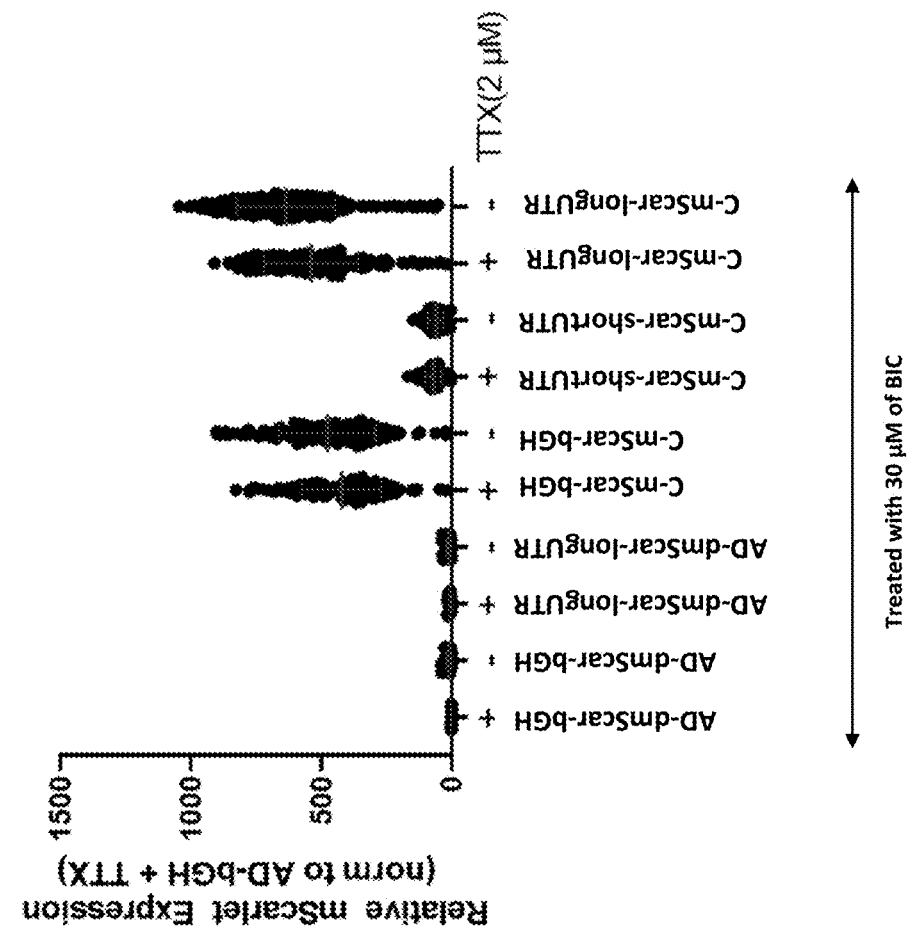
FIG. 6A is a graph showing the relative reporter gene expression in cells transduced with AAV vectors comprising the indicated AAV expression cassettes, which were treated with 30 µM of BIC and further either treated with 2 µM TTX, or left untreated with TTX, as indicated.

The activity-dependent expression of the hSARE-hArcMin promoter is further illustrated by FIG. 6A-B. As shown in FIG. 6A, the constitutive promoter, hSyn, drives high levels of mScarlet expression, irrespective of the presence of TTX. Strikingly, FIG. 6B shows that when cells are not treated with TTX, but instead treated with 30 µM of BIC to promote neuronal activity, the hSARE-hArcMin promoter drives high levels of reporter gene expression. Notably, FIG. 6B shows that the AAV expression construct comprising the hSARE-hArcMin promoter in combination with long 3'UTR resulted in about 5-fold higher level of dmScarlet expression in the presence of TTX, as compared to the AAV expression construct comprising the hSARE-hArcMin promoter in combination bGHpA. These results further demonstrates the neuronal activity-dependent induction of the hSARE-hArcMin promoter.

To determine the subcellular localization and levels of the expressed fluorescent protein, neurons expressing the reporter gene under the constitutive hSyn promoter or the activity-dependent hSARE-hArcMin promoter were observed using microscopy.

Figure 7:
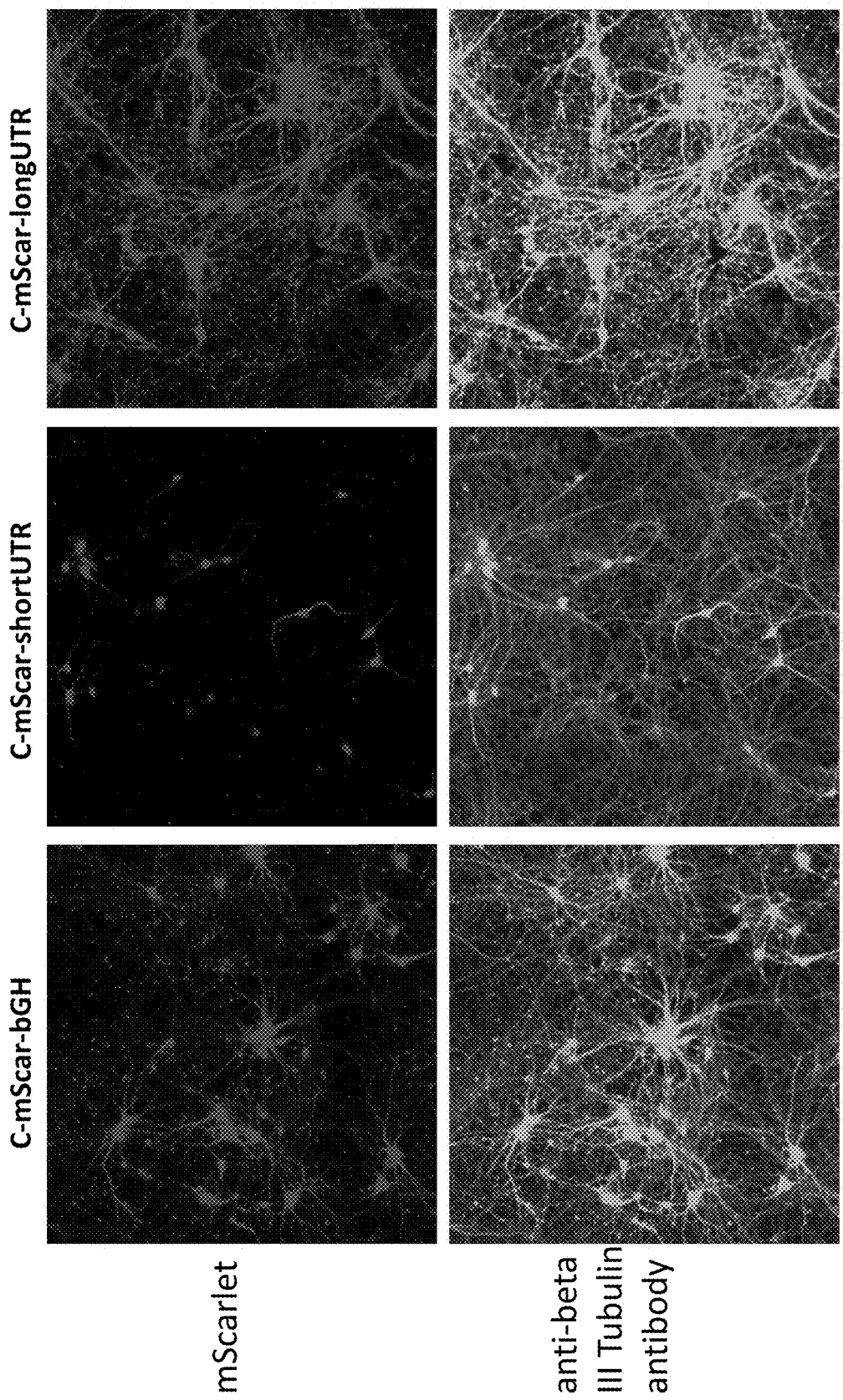
FIG. 7 depicts microscopy images showing mScarlet fluorescence (top images) and staining with the neuronal marker, anti-beta III Tubulin antibody (bottom images) of neurons transduced with AAV vectors comprising the indicated constitutive (C) AAV expression cassettes.

As shown in FIG. 7, cells expressing mScarlet using the constitutive promoter, hSyn, were fluorescent, however, the level of fluorescence varied based on the 3'UTR region or polyadenylation signal of the expression cassette. For instance, expression cassettes comprising the long 3'UTR resulted in the higher levels of mScarlet gene expression, followed by the expression cassettes comprising the short 3'UTR. Expression cassettes comprising the short 3'UTR resulted in the considerably lower levels of mScarlet gene expression. In contrast, the expression of the reporter protein under the activity-dependent hSARE-hArcMin promoter do not vary based on the type of 3'UTR used. In particular, FIGS. 5 and 6 show that AAV expression constructs comprising the hSARE-hArcMin promoter in combination with bGHpA or long 3'UTR resulted in similar levels of dmScarlet expression in the presence of neuronal activity.

Furthermore, FIG. 7 shows that the subcellular localization of mScarlet expressed from a constitutive promoter varies based on the 3'UTR region or polyadenylation signal of the expression cassette. While expression cassettes comprising the long 3'UTR and bGHpA resulted in mScarlet expression in the cell body and neurites, expression cassettes comprising the short 3'UTR resulted in mScarlet expression only in the cell body.

Figure 8:
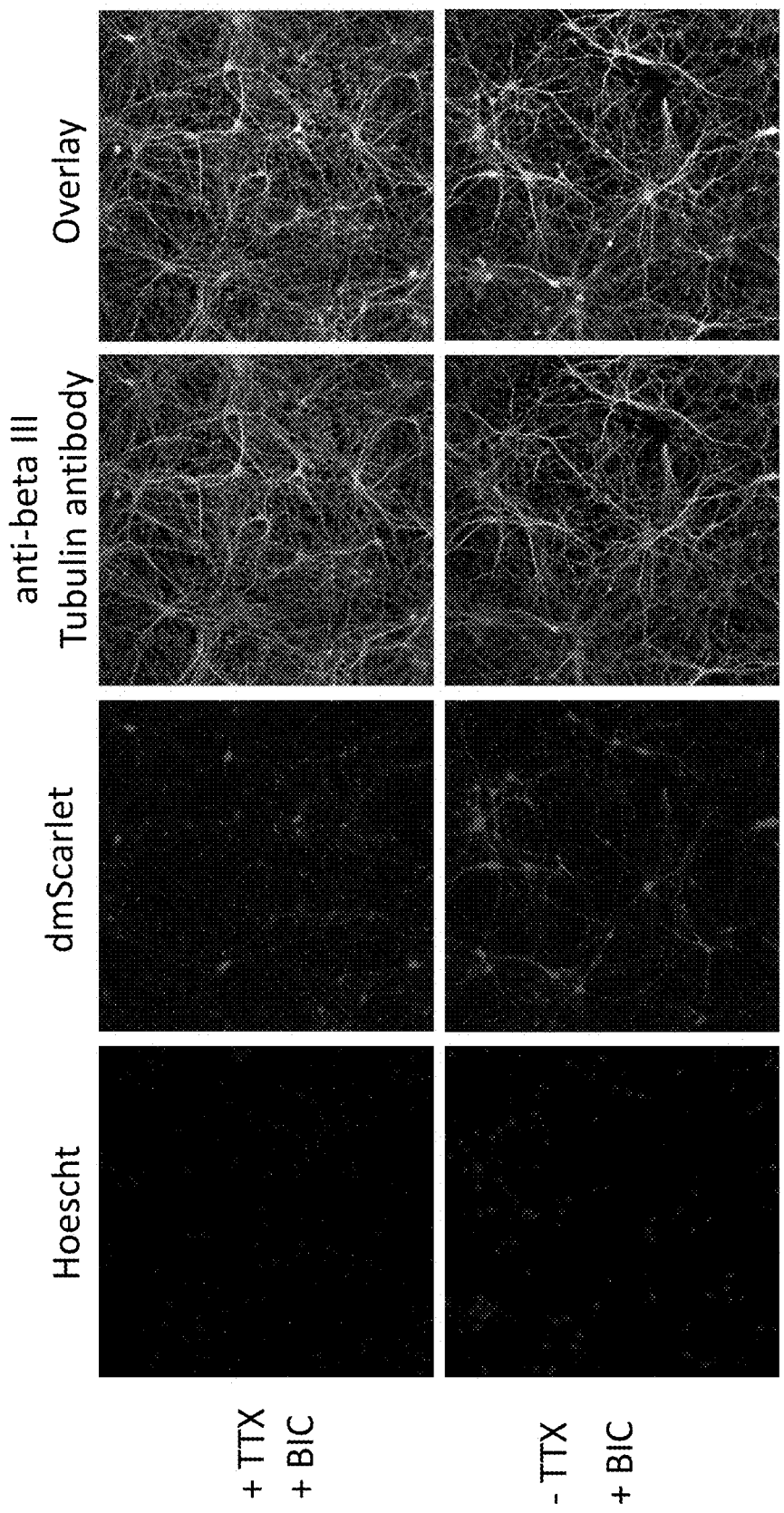
FIG. 8 depicts microscopy images showing: Hoescht DNA staining, dmScarlet fluorescence, anti-beta III Tubulin antibody staining and overlay images, of neurons transduced with AAV vectors comprising the "AD-dmScar-bGH" AAV expression cassette. The top panel shows images of cells treated with 2 µM TTX and 30 µM of BIC, and the bottom panel shows images of cells which were left untreated with TTX but treated with 30 µM of BIC.
Figure 12:
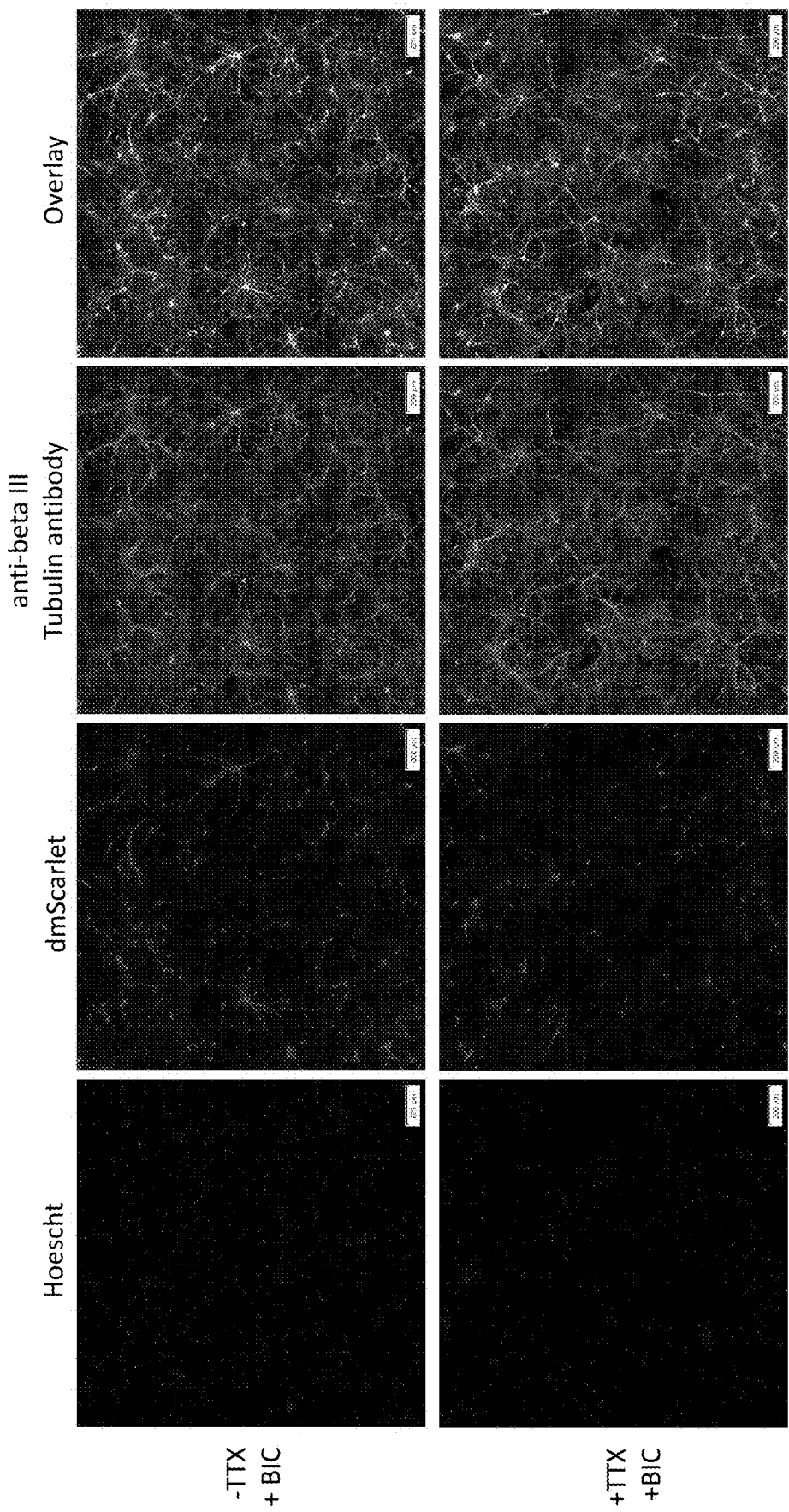
FIG. 12 depicts microscopy images showing: Hoescht DNA staining, dmScarlet fluorescence, anti-beta III Tubulin antibody staining and overlay images, of neurons transduced with AAV vectors comprising the "AD-dmScar-longUTR" AAV expression cassette. The top panel shows images of cells treated with 2 µM TTX and 30 µM of BIC, and the bottom panel shows images of cells which were left untreated with TTX but treated with 30 µM of BIC.

As shown in FIGS. 8 and 12, AAV expression constructs comprising the hSARE-hArcMin promoter in combination with bGHpA (FIG. 8) or long 3'UTR (FIG. 12) resulted in similar levels of dmScarlet expression in the presence of neuronal activity. Furthermore, cells expressing dmScarlet using the activity-dependent hSARE-hArcMin promoter showed fluorescence signal in the cell body and neurites upon neuronal activation (in the absence of TTX and presence of BIC).

In sum, the results described above demonstrate that the synthetic hSARE-hArcMin promoter promotes higher levels of gene expression in neurons that are active, as compared to in neurons that are inhibited or resting. Therefore, the synthetic hSARE-hArcMin promoter may be used to drive neuronal activity-dependent expression of any target gene, such as, a Rett Syndrome-associated gene as described herein.

Example 5: Characterization of AAV Expression Cassettes Comprising BDNF

The AAV particles generated in Example 2 or 3 are administered by injection into mecp2 mutant mice, which exhibit symptoms similar to Rett Syndrome, to test whether the expression of BDNF using the activity dependent promoter, hSARE-hArcMin, decreases the severity of one or more symptoms. The ability of activity dependent BDNF expression to delay the onset of Rett syndrome symptoms in newborn mecp2 mutant mice is also tested.

The foregoing is illustrative of the present invention, and is not to be construed as limiting thereof.

Numbered Embodiments

The following list of embodiments is included herein for illustration purposes only and is not intended to be comprehensive or limiting. The subject matter to be claimed is expressly not limited to the following embodiments.

Embodiment 1. A nucleic acid comprising an adeno-associated virus (AAV) expression cassette, wherein the AAV expression cassette comprises, from 5' to 3':
a 5' inverted terminal repeat (ITR);
a synthetic, activity-dependent promoter;
a Rett Syndrome-associated gene; and
a 3' ITR.

Embodiment 2. The nucleic acid of embodiment 1, wherein the promoter drives expression of the Rett-syndrome-associated gene.

Embodiment 3. The nucleic acid of embodiment 1 or 2, wherein the promoter is a MECP2-independent promoter.

Embodiment 4. The nucleic acid of any one of embodiments 1-3, wherein the promoter comprises a nucleic acid sequence derived from a promoter of a neuronal immediate early gene.

Embodiment 5. The nucleic acid of embodiment 4, wherein the neuronal immediate early gene is selected from the group consisting of the Arc gene, the c-fos gene, and the egr-1 gene.

Embodiment 6. The nucleic acid of any one of embodiments 1-5, wherein the promoter comprises a minimal Arc gene promoter (ArcMin).

Embodiment 7. The nucleic acid of embodiment 6, wherein the ArcMin is a human ArcMin (hArcMin).

Embodiment 8. The nucleic acid of embodiment 7, wherein the hArcMin comprises a nucleic acid sequence of SEQ ID NO: 12, or a sequence at least 90% identical thereto.

Embodiment 9. The nucleic acid of any one of embodiments 1-8, wherein the promoter comprises a cyclic AMP response element (CRE), a serum response element (SRE), a synaptic activity response element (SARE), a MEF2 response element, or a combination thereof.

Embodiment 10. The nucleic acid of embodiment 9, wherein the promoter comprises a synaptic activity response element (SARE).

Embodiment 11. The nucleic acid of embodiment 10, wherein the synaptic activity response element (SARE) is a human synaptic activity response element (hSARE).

Embodiment 12. The nucleic acid of embodiment 11, wherein the hSARE comprises a nucleic acid sequence of SEQ ID NO: 11, or a sequence at least 90% identical thereto.

Embodiment 13. The nucleic acid of any one of embodiments 1-12, wherein the promoter comprises a human ArcMin (hArcMin) and at least one hSARE.

Embodiment 14. The nucleic acid of embodiment 13, wherein the promoter comprises hArcMin and one hSARE.

Embodiment 15. The nucleic acid of embodiment 14, wherein the promoter comprises a nucleic acid sequence of SEQ ID NO: 6, or a sequence at least 90% identical thereto.

Embodiment 16. The nucleic acid of embodiment 13, wherein the promoter comprises hArcMin and five hSAREs.

Embodiment 17. The nucleic acid of embodiment 16, wherein the promoter comprises a nucleic acid sequence of SEQ ID NO: 16, or a sequence at least 90% identical thereto.

Embodiment 18. The nucleic acid of any one of embodiments 1-17, wherein the promoter binds to a neuronal activity dependent transcription factor.

Embodiment 19. The nucleic acid of embodiment 18, wherein the neuronal activity dependent transcription factor is cAMP-responsive element binding protein (CREB), myocyte enhancer factor 2 (MEF2), serum response factor (SRF), or Elk-1.

Embodiment 20. The nucleic acid of any one of embodiments 1-19, wherein the Rett-syndrome-associated gene encodes brain-derived neurotrophic factor (BDNF), insulin-like growth factor 1 (IGF1), methyl-CpG-binding protein 2 (MECP2), Huntingtin protein, Huntington-associated protein 1, Orthodenticle homeobox 2 (OTX-2), FXYD Domain Containing Ion Transport Regulator 1 (FXYD1), Neurexin-2-alpha (NRXN2), or Protein Kinase C Gamma (PRKCG).

Embodiment 21. The nucleic acid of embodiment 20, wherein the Rett-syndrome-associated gene encodes brain-derived neurotrophic factor (BDNF).

Embodiment 22. The nucleic acid of embodiment 21, wherein the BDNF is a human BDNF.

Embodiment 23. The nucleic acid of embodiment 22, wherein the BDNF is encoded by a nucleic acid sequence of SEQ ID NO: 7, or a sequence at least 90% identical thereto.

Embodiment 24. The nucleic acid of any one of embodiments 1-23, wherein at least one of the 5' ITR and the 3' ITR is about 110 to about 160 nucleotides in length.

Embodiment 25. The nucleic acid of any one of embodiments 1-24, wherein the 5' ITR is the same length as the 3' ITR.

Embodiment 26. The nucleic acid of any one of embodiments 1-24, wherein the 5' ITR and the 3' ITR have different lengths.

Embodiment 27. The nucleic acid of any one of embodiments 1-26, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

Embodiment 28. The nucleic acid of any one of embodiments 1-23, wherein the 5' ITR comprises the sequence of SEQ ID NO: 1.

Embodiment 29. The nucleic acid of any one of embodiments 1-23, wherein the 3' ITR comprises the sequence of SEQ ID NO: 2.

Embodiment 30. The nucleic acid of any one of embodiments 1-29, wherein the AAV cassette comprises a brain-derived neurotrophic factor (BDNF) short 3' UTR, or a BDNF long 3' UTR.

Embodiment 31. The nucleic acid of embodiment 30, wherein the BDNF short 3' UTR, or the BDNF long 3' UTR is located between the Rett-syndrome-associated gene and the 3' ITR.

Embodiment 32. The nucleic acid of embodiment 30 or embodiment 31, wherein the AAV cassette comprises a BDNF short 3' UTR.

Embodiment 33. The nucleic acid of embodiment 32, wherein the BDNF short 3' UTR comprises a nucleic acid sequence of SEQ ID NO: 8, or a sequence at least 90% identical thereto.

Embodiment 34. The nucleic acid of embodiment 30 or embodiment 31, wherein the AAV cassette comprises a BDNF long 3' UTR.

Embodiment 35. The nucleic acid of embodiment 34, wherein the BDNF long 3' UTR comprises a nucleic acid sequence of SEQ ID NO: 10, or a sequence at least 90% identical thereto.

Embodiment 36. The nucleic acid of any one of embodiments 1-35, wherein the AAV cassette comprises a polyadenylation signal.

Embodiment 37. The nucleic acid of embodiment 36, wherein the polyadenylation signal is a polyadenylation signal isolated or derived from one or more of the following genes: simian virus 40 (SV40), rBG, α-globin, β-globin, human collagen, human growth hormone (hGH), polyoma virus, human growth hormone (hGH) or bovine growth hormone (bGH).

Embodiment 38. The nucleic acid of embodiment 36, wherein the AAV cassette comprises a bGH polyadenylation signal.

Embodiment 39. The nucleic acid of embodiment 38, wherein the bGH polyadenylation signal comprises a nucleic acid sequence of SEQ ID NO: 9, or a sequence at least 90% identical thereto.

Embodiment 40. The nucleic acid of any one of embodiments 1-39, wherein the AAV cassette comprises at least one stuffer sequence.

Embodiment 41. The nucleic acid of embodiment 40, wherein the at least one stuffer sequence comprises a nucleic acid sequence of SEQ ID NO: 13, or a sequence at least 90% identical thereto.

Embodiment 42. The nucleic acid of any one of embodiments 1-41, wherein the AAV expression cassette comprises a Kozak sequence, wherein the Kozak sequence overlaps with the start codon of the Rett-syndrome-associated gene.

Embodiment 43. The nucleic acid of embodiment 42, wherein the Kozak sequence comprises a nucleic acid sequence of SEQ ID NO: 14, or a sequence at least 90% identical thereto; or a nucleic acid sequence of SEQ ID NO: 15, or a sequence at least 90% identical thereto.

Embodiment 44. The nucleic acid of any one of embodiments 1-43, wherein the AAV expression cassette comprises a nucleic acid sequence SEQ ID NO: 3, or a sequence at least 90% identical thereto; SEQ ID NO: 4 or a sequence at least 90% identical thereto; or SEQ ID NO: 5 or a sequence at least 90% identical thereto.

Embodiment 45. A plasmid comprising the nucleic acid of any one of embodiments 1-44.

Embodiment 46. A cell comprising the nucleic acid of any one of embodiments 1-44 or the plasmid of embodiment 45.

Embodiment 47. A method of producing a recombinant AAV vector, the method comprising contacting an AAV producer cell with the nucleic acid of any one of embodiments 1-44, or the plasmid of embodiment 45.

Embodiment 48. A recombinant AAV vector produced by the method of embodiment 47.

Embodiment 49. The recombinant AAV vector of embodiment 48, wherein the vector is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

Embodiment 50. The recombinant AAV vector of embodiment 48 or embodiment 49, wherein the recombinant AAV vector is a single-stranded AAV (ssAAV).

Embodiment 51. The recombinant AAV vector of any one of embodiments 48-50, wherein the recombinant AAV vector is a self-complementary AAV (scAAV).

Embodiment 52. The recombinant AAV vector of any one of embodiments 48-51, wherein the AAV vector comprises a capsid protein of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

Embodiment 53. The recombinant AAV vector of any one of embodiments 48-52, wherein the AAV vector comprises a capsid protein with one or more substitutions or mutations, as compared to a wildtype AAV capsid protein.

Embodiment 54. A composition, comprising: (a) the nucleic acid of any one of embodiments 1-44, the plasmid of embodiment 45, the cell of embodiment 46, or the recombinant AAV vector of any one of embodiments 48-53; and (b) a pharmaceutically acceptable carrier.

Embodiment 55. A method for expressing a Rett-syndrome-associated gene in a subject in need thereof, comprising administering to the subject a therapeutically effective amount of the nucleic acid of any one of embodiments 1-44, the plasmid of embodiment 45, the cell of embodiment 46, the recombinant AAV vector of any one of embodiments 48-53, or the composition of embodiment 54.

Embodiment 56. The method of embodiment 55, wherein the subject has Rett syndrome.

Embodiment 57. A method for treating or delaying the onset of Rett syndrome in a subject, comprising administering to the subject a therapeutically effective amount of the nucleic acid of any one of embodiments 1-44, the plasmid of embodiment 45, the cell of embodiment 46, the recombinant AAV vector of any one of embodiments 48-53, or the composition of embodiment 54.

Embodiment 58. A method for expressing brain-derived neurotrophic factor (BDNF) in a subject in need thereof, comprising administering to the subject a therapeutically effective amount of the nucleic acid of any one of embodiments 1-44, the plasmid of embodiment 45, the cell of embodiment 46, the recombinant AAV vector of any one of embodiments 48-53, or the composition of embodiment 54.

Embodiment 59. The method of embodiment 58, wherein the subject has a cognitive disorder, or a stress-related disorder.

Embodiment 60. The method of embodiment 58, wherein the subject has depression, obsessive-compulsive disorder, Alzheimer's disease, Huntington's disease, and dementia, anorexia nervosa and bulimia nervosa, schizophrenia, epilepsy, post-traumatic stress disorder, obesity, Rett syndrome, or post-chemotherapy cognitive impairment.

Embodiment 61. A method of treating or delaying the onset of a BDNF-associated disease in a subject, comprising administering to the subject a therapeutically effective amount of the nucleic acid of any one of embodiments 1-44, the plasmid of embodiment 45, the cell of embodiment 46, the recombinant AAV vector of any one of embodiments 48-53, or the composition of embodiment 54.

Embodiment 62. The method of embodiment 61, wherein the BDNF-associated disease is a cognitive disorder, and/or a stress-related disorder.

Embodiment 63. The method of embodiment 61, wherein the BDNF-associated disease is depression, obsessive-compulsive disorder, Alzheimer's disease, Huntington's disease, and dementia, anorexia nervosa, bulimia nervosa, schizophrenia, epilepsy, post-traumatic stress disorder, bipolar disease, Rett syndrome, major depressive disorder, or post-chemotherapy cognitive impairment.

Embodiment 64. A method of treating or delaying the onset of a MECP2-associated disease in a subject, comprising administering to the subject a therapeutically effective amount of the nucleic acid of any one of embodiments 1-44, the plasmid of embodiment 45, the cell of embodiment 46, the recombinant AAV vector of any one of embodiments 48-53, or the composition of embodiment 54.

Embodiment 65. The method of embodiment 64, wherein the MECP2-associated disease is MECP2 duplication syndrome, MECP2-related severe neonatal encephalopathy, PPM-X syndrome, or Rett syndrome.

Embodiment 66. The method of any one of embodiment 55-65, wherein the subject is a human subject.

Embodiment 67. The method of any one of embodiments 55-66, wherein the nucleic acid, the plasmid, the cell, the recombinant AAV vector, or composition is administered by injection into the central nervous system.

Embodiment 68. The method of any one of embodiments 55-67, wherein the Rett Syndrome-associated gene is expressed in the neurons of the subject.

Embodiment 69. The method of embodiment 68, wherein the neurons are active neurons.

What is claimed is:

1. A nucleic acid comprising an adeno-associated virus (AAV) expression cassette, wherein the AAV expression cassette comprises, from 5' to 3':
 a 5' inverted terminal repeat (ITR);
 a minimal human Arc gene promoter (hArcMin) set forth by SEQ ID no. 12;
 a Rett Syndrome-associated gene; and
 a 3' ITR.

2. The nucleic acid of claim 1, wherein the promoter drives expression of the Rett-syndrome-associated gene.

3. The nucleic acid of claim 1, further comprising a cyclic AMP response element (CRE), a serum response element (SRE), a synaptic activity response element (SARE), a MEF2 response element, or a combination thereof.

4. The nucleic acid of claim 3, wherein the nucleic acid comprises at least one synaptic activity response element (SARE).

5. The nucleic acid of claim 4, wherein the synaptic activity response element (SARE) is a human synaptic activity response element (hSARE) of SEQ ID NO: 11, or a sequence at least 95% identical thereto.

6. The nucleic acid of claim 5, wherein the hArcMin and SARE are set forth by SEQ ID NO: 6, or a sequence at least 95% identical thereto.

7. The nucleic acid of claim 6, wherein the promoter comprises the nucleic acid sequence of SEQ ID NO: 6.

8. The nucleic acid of claim 5, wherein the hArcMin and SARE are set forth by SEQ ID NO: 16, or a sequence at least 95% identical thereto.

9. The nucleic acid of claim 8, wherein the promoter comprises the nucleic acid sequence of SEQ ID NO: 16.

10. The nucleic acid of claim 5, wherein the human synaptic activity response element (hSARE) comprises a nucleic acid sequence of SEQ ID NO: 11.

11. The nucleic acid of claim 1, wherein the Rett-syndrome-associated gene encodes brain-derived neurotrophic factor (BDNF), insulin-like growth factor 1 (IGF1), methyl-CpG-binding protein 2 (MECP2), Huntingtin protein, Huntington-associated protein 1, Orthodenticle homeobox 2 (OTX-2), FXYD Domain Containing Ion Transport Regulator 1 (FXYD1), Neurexin-2-alpha (NRXN2), or Protein Kinase C Gamma (PRKCG).

12. The nucleic acid of claim 1, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

13. The nucleic acid of claim 1, wherein the 5' ITR comprises the sequence of SEQ ID NO: 1, or the 3' ITR comprises the sequence of SEQ ID NO: 2, or a combination thereof.

14. The nucleic acid of claim 1, wherein the AAV cassette comprises one of the following located between the Rett-syndrome-associated gene and the 3' ITR: (a) a brain-derived neurotrophic factor (BDNF) short 3' UTR, (b) a BDNF long 3' UTR, or (c) a polyadenylation signal.

15. The nucleic acid of claim 14, wherein the AAV cassette comprises a BDNF short 3' UTR of SEQ ID NO: 8.

16. The nucleic acid of claim 15, wherein the BDNF short 3' UTR comprises a nucleic acid sequence of SEQ ID NO: 8.

17. The nucleic acid of claim 14, wherein the AAV cassette comprises a BDNF long 3' UTR of SEQ ID NO: 10.

18. The nucleic acid of claim 16, wherein the BDNF long 3' UTR comprises a nucleic acid sequence of SEQ ID NO: 10.

19. The nucleic acid of claim 14, wherein the polyadenylation signal is a polyadenylation signal isolated or derived from one or more of the following genes: simian virus 40 (SV40), rBG, a-globin, -globin, human collagen, human growth hormone (hGH), polyoma virus, human growth hormone (hGH) or bovine growth hormone (bGH).

20. The nucleic acid of claim 19, wherein the AAV cassette comprises a bGH polyadenylation signal and wherein the bGH polyadenylation signal comprises a nucleic acid sequence of SEQ ID NO: 9, or a sequence at least 90% identical thereto.

21. The nucleic acid of claim 20, wherein the bGH polyadenylation signal comprises a nucleic acid sequence of SEQ ID NO: 9.

22. The nucleic acid of claim 1, wherein the AAV expression cassette comprises one of the following: (a) a nucleic acid sequence of SEQ ID NO: 3, or a sequence at least 95% identical thereto; (b) a nucleic acid sequence of SEQ ID NO: 4 or a sequence at least 95% identical thereto; or (c) a nucleic acid sequence of SEQ ID NO: 5 or a sequence at least 95% identical thereto.

23. The nucleic acid of claim 22, wherein the AAV expression cassette comprises one of the following: (a) a nucleic acid sequence of SEQ ID NO: 3; (b) a nucleic acid sequence of SEQ ID NO: 4; or (c) a nucleic acid sequence of SEQ ID NO: 5.

24. A method of producing a recombinant AAV vector, the method comprising contacting an AAV producer cell with the nucleic acid of claim 1.

25. A recombinant AAV vector produced by the method of claim 24.

26. The recombinant AAV vector of claim 25, wherein the AAV vector comprises a capsid protein of AAVI, AAV2, AAV3, AAV4, AAV5, AAV6, AAV7, AAV8, AAV10, AAVI 1, AAV12, AAVrh8, AAVrh0, AAVrh32.33, AAVrh74, Avian AAV or Bovine AAV.

27. A composition, comprising: (a) the nucleic acid of claim 1; and (b) a pharmaceutically acceptable carrier.

* * * * *

UNITED STATES PATENT AND TRADEMARK OFFICE
CERTIFICATE OF CORRECTION

PATENT NO. : 12,104,163 B2
APPLICATION NO. : 17/406723
DATED : October 1, 2024
INVENTOR(S) : O'Banion It is certified that error appears in the above-identified patent and that said Letters Patent is hereby corrected as shown below:

In the Specification

In Column 5, Line 27, delete "M" and insert -- $\mu M$ --, therefor.

In Column 5, Line 32, delete "bicuculine" and insert -- bicuculline --, therefor.

In Column 5, Line 52, delete "Hoescht" and insert -- Hoechst --, therefor.

In Column 6, Line 28, delete "poly A" and insert -- polyA --, therefor.

In Column 6, Line 51, delete "Hoescht" and insert -- Hoechst --, therefor.

In Column 8, Lines 7-8, delete "O-methylphophoroamidite" and insert -- O- methylphosphoramidite --, therefor.

In Column 12, Line 5, delete "$Ca^{2-}$" and insert -- $Ca^{2+}$ --, therefor.

In Column 14, Line 49, delete "neutrophin-3" and insert -- neurotrophin-3 --, therefor.

In Column 17, Line 29, delete "hydroylase" and insert -- hydroxylase --, therefor.

In Column 17, Line 52, delete "phosphoeholpyruvate" and insert -- phosphoenolpyruvate --, therefor.

In Column 18, Line 23, delete "excitary" and insert -- excitatory --, therefor.

In Column 18, Line 48, delete "MAPKI" and insert -- MAPK1 --, therefor.

In Column 20, Line 7, delete "rBG." and insert -- rBG, --, therefor.

Signed and Sealed this
Eighteenth Day of February, 2025

Coke Morgan Stewart
*Acting Director of the United States Patent and Trademark Office*

CERTIFICATE OF CORRECTION (continued)
U.S. Pat. No. 12,104,163 B2

In Column 24, Line 49, delete "any one of the any one of the" and insert -- any one of the --, therefor.

In Column 30, Line 21, delete "poly A" and insert -- polyA --, therefor.

In Column 31, Line 5, delete "bicuculine" and insert -- bicuculline --, therefor.

In Column 31, Line 15, delete "Hoescht" and insert -- Hoechst --, therefor.

In Column 31, Line 35, delete "bicuculine" and insert -- bicuculline --, therefor.

In the Claims

In Column 104, Claim 18, Line 11, delete "16," and insert -- 17, --, therefor.

In Column 104, Claim 19, Line 18, delete "a-globin, -globin," and insert -- α-globin, β-globin, --, therefor.

In Column 104, Claim 26, Line 48, delete "AAVI," and insert -- AAV1, --, therefor.

In Column 104, Claim 26, Line 49-50, delete "AAV1 1," and insert -- AAV11, --, therefor.

In Column 104, Claim 26, Line 50, delete "AAVrh0," and insert -- AAVrh10, --, thereof.

SEQUENCE LISTING

```
<160> NUMBER OF SEQ ID NOS: 38

<210> SEQ ID NO 1
<211> LENGTH: 141
<212> TYPE: DNA
<213> ORGANISM: Artificial Sequence
<220> FEATURE:
<223> OTHER INFORMATION: 5' ITR

<400> SEQUENCE: 1
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc t                                              141

<210> SEQ ID NO 2
<211> LENGTH: 166
<212> TYPE: DNA
<213> ORGANISM: Artificial Sequence
<220> FEATURE:
<223> OTHER INFORMATION: 3' ITR

<400> SEQUENCE: 2
tcgagccatg gcgcgccat cgatgaggaa cccctagtga tggagttggc cactccctct       60
ctgcgcgctc gctcgctcac tgaggccggg cgaccaaagg tcgcccgacg cccgggcttt    120
gcccgggcgg cctcagtgag cgagcgagcg cgcagctgcc tgcagg                   166

<210> SEQ ID NO 3
<211> LENGTH: 4200
<212> TYPE: DNA
<213> ORGANISM: Artificial Sequence
<220> FEATURE:
<223> OTHER INFORMATION: hSARE-ArcMin-BDNF-short 3' UTR

<400> SEQUENCE: 3
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgcgtcgac aggcctccta ggcggaccgc ttgcatgcac    180
gcgtgggtgg tgcagagtct gcatgcgtga ggagctcctg ggcgcgtcac agccgcgcta    240
ttctcagcgt ctctcctttt atggctccgg aagtgagctg gggttgctgg cagccgtccc    300
tcggtccccg caggctgaat gagccccgcc gtccggggtg ggaggtacgg agcggaggga    360
ttagtcatcc tggccccgcc atgtgtgcag ggggtgggac ctcccgtccc ttgccgcccg    420
ggagccgagt gggcgcaggg cggggcctgc aggggcgcgg gcggggcgct ggcggggagc    480
ctgcggctgg gccaatgaga aaccgggctc ggcgagccgg ccgcccacgg gcctcgctgg    540
```

```
ctgcataaag agccggcggc caggactcag cgcagagctc gggcgcggcg tcctccctcc     600
gcagcagccg agccggacct gcctccccgg gcgtgctccg ccggccccgc cgccggcccg     660
cagcgacaga caggcgctcc ccgcagctcc gcacgggacc caggccgccg acccccagcg     720
ccggaccacc ctctgtccgc cccgaggagt ttgccgcctg ccggagcacc tgcgcacaga     780
ccggtcgcca ccatgaccat ccttttcctt actatggtta tttcatactt tggttgcatg     840
aaggctgccc ccatgaaaga agcaaacatc cgaggacaag gtggcttggc ctacccaggt     900
gtgcggaccc atgggactct ggagagcgtg aatgggccca aggcaggttc aagaggcttg     960
acatcattgg ctgacacttt cgaacacgtg atagaagagc tgttggatga ggaccagaaa    1020
gttcggccca atgaagaaaa caataaggac gcagacttgt acacgtccag ggtgatgctc    1080
agtagtcaag tgccttttgga gcctcctctt ctctttctgc tggaggaata caaaaattac    1140
ctagatgctg caaacatgtc catgagggtc cggcgccact ctgaccctgc ccgccgaggg    1200
gagctgagcg tgtgtgacag tattagtgag tgggtaacgg cggcagacaa aaagactgca    1260
gtggacatgt cgggcgggac ggtcacagtc cttgaaaagg tccctgtatc aaaaggccaa    1320
ctgaagcaat acttctacga gaccaagtgc aatcccatgg gttacacaaa agaaggctgc    1380
aggggcatag acaaaaggca ttggaactcc cagtgccgaa ctacccagtc gtacgtgcgg    1440
gcccttacca tggatagcaa aaagagaatt ggctggcgat tcataaggat agacacttct    1500
tgtgtatgta cattgaccat taaagggga agatagggta cctggattta tgttgtatag    1560
attagattat attgagacaa aaattatcta tttgtatata tacataacag ggtaaattat    1620
tcagttaaga aaaaataat tttatgaact gcatgtataa atgaagttta tacagtacag    1680
tggttctaca atctatttat tggacatgtc catgaccaga agggaaacag tcatttgcgc    1740
acaacttaaa aagtctgcat tacattcctt gataatgttg tggtttgttg ccgttgccaa    1800
gaactgaaaa cataaaaagt taaaaaaaat aataaattgc atgctgcttt aattgtgaat    1860
tgataataag cgcgccatcg atgtgaagtg ggtaaccttt atttcccttc ttttttctctt    1920
tagctcggct tattccaggg gtgtgtttcg tcgagatgca cacaagagtg aggttgctca    1980
tcggtttaaa gatttgggag aagaaaattt caaagccttg gtgttgattg cctttgctca    2040
gtatcttcag cagtgtccat ttgaagatca tgtaaaatta gtgaatgaag taactgaatt    2100
tgcaaaaaca tgtgttgctg atgagtcagc tgaaaattgt gacaaatcac ttcataccct    2160
ttttggagac aaattatgca cagttgcaac tcttcgtgaa acctatggtg aaatggctga    2220
ctgctgtgca aaacaagaac ctgagagaaa tgaatgcttc ttgcaacaca agatgacaa    2280
cccaaacctc ccccgattgg tgagaccaga ggttgatgtg atgtgcactg cttttcatga    2340
caatgaagag accttttga aaaaatactt atacgaaatt gccagaagac atccttactt    2400
ttatgccccg gaactccttt tctttgctaa aaggtataaa gctgctttta cagaatgttg    2460
ccaagctgct gataaagctg cctgcctgtt gccaaagctc gatgaacttc gggatgaagg    2520
gaaggcttcg tctgccaaac agagactcaa gtgtgccagt ctccaaaaat ttggagaaag    2580
agctttcaaa gcatgggcag tagctcgcct gagccagaga tttcccaaag ctgagttttgc    2640
agaagttttcc aagttagtga cagatcttac caaagtccac acggaatgct gccatggaga    2700
tctgcttgaa tgtgctgatg acagggcgga ccttgccaag tatatctgtg aaaatcaaga    2760
ttcgatctcc agtaaactga aggaatgctg tgaaaaacct ctgttggaaa atcccactg    2820
cattgccgaa gtgaaaatg atgagatgcc tgctgacttg ccttcattag ctgctgattt    2880
tgttgaaagt aaggatgttt gcaaaaacta tgctgaggca aaggatgtct tcctgggcat    2940
```

| | | |
|---|---|---|
| gtttttgtat gaatatgcaa gaaggcatcc tgattactct gtcgtgctgc tgctgagact | 3000 |
| tgccaagacc tatgaaacca ctctagagaa gtgctgtgcc gctgcagatc ctcatgaatg | 3060 |
| ctatgccaaa gtgttcgatg aatttaaacc tcttgtggaa gagcctcaga atttaatcaa | 3120 |
| acaaaattgt gagcttttg agcagcttgg agagtacaaa ttccagaatg cgctattagt | 3180 |
| tcgttacacc aagaaagtac cccaagtgtc aactccaact cttgtagagg tctcaagaaa | 3240 |
| cctaggaaaa gtgggcagca aatgttgtaa acatcctgaa gcaaaaagaa tgccctgtgc | 3300 |
| agaagactat ctatccgtgg tcctgaacca gttatgtgtg ttgcatgaga aaacgccagt | 3360 |
| aagtgacaga gtcaccaaat gctgcacaga atccttggtg aacaggcgac catgtcgtga | 3420 |
| aacctatggt gaaatggctg actgctgtgc aaaacaagaa cctgagagaa atgaatgctt | 3480 |
| cttgcaacac aaagatgaca acccaaacct cccccgattg gtgagaccag aggttgatgt | 3540 |
| gatgtgcact gcttttcatg acaatgaaga gaccttttg aaaaaatact tatacgaaat | 3600 |
| tgccagaaga catccttact tttatgcccc ggaactcctt ttctttgcta aaaggtataa | 3660 |
| agctgctttt acagaatgtt gccaagctgc tgataaagct gcctgcctgt tgccaaagct | 3720 |
| cgatgaactt cgggatgaag ggaaggcttc gtctgccaaa cagagactca agtgtgccag | 3780 |
| tctccaaaaa tttggagaaa gagctttcaa agcatgggca gtagctcgcc tgagccagac | 3840 |
| ttttcagctc tggaagtcga tgaaacatac gttcccaaag agtttaatgc tgaaacattc | 3900 |
| accttccatg cagatatatg cacactttct gagaaggaga gacaaatcaa gaaacaaact | 3960 |
| gcacttgttg agctcgtgaa acacaagccc aaggcaacaa aagagcaact gaaagctgtt | 4020 |
| atggatgatt tcgctcgagc catgggcgcg ccatcgatga ggaacccta gtgatggagt | 4080 |
| tggccactcc ctctctgcgc gctcgctcgc tcactgaggc cgggcgacca aaggtcgccc | 4140 |
| gacgcccggg ctttgcccgg gcggcctcag tgagcgagcg agcgcgcagc tgcctgcagg | 4200 |

<210> SEQ ID NO 4
<211> LENGTH: 4098
<212> TYPE: DNA
<213> ORGANISM: Artificial Sequence
<220> FEATURE:
<223> OTHER INFORMATION: hSARE-ArcMin-BDNF-bGHpA-hAlb

<400> SEQUENCE: 4

| | | |
|---|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggttcc ttgcgtcgac aggcctccta gcggaccgc ttgcatgcac | 180 |
| gcgtgggtgg tgcagagtct gcatgcgtga ggagctcctg ggcgcgtcac agccgcgcta | 240 |
| ttctcagcgt ctctcctttt atggctccgg aagtgagctg gggttgctgg cagccgtccc | 300 |
| tcggtccccg caggctgaat gagccccgcc gtccggggtg ggaggtacgg agcggaggga | 360 |
| ttagtcatcc tggccccgcc atgtgtgcag ggggtgggac ctcccgtccc ttgccgcccg | 420 |
| ggagccgagt gggcgcaggg cggggcctgc aggggcgcgg gcggggcgct ggcggggagc | 480 |
| ctgcggctgg gccaatgaga aaccggctc ggcgagccgg ccgcccacgg gcctcgctgg | 540 |
| ctgcataaag agccggcggc caggactcag cgcagagctc gggcgcggcg tcctccctcc | 600 |
| gcagcagccg agccggacct gcctccccgg gcgtgctccg ccgcccgc cgccggcccg | 660 |
| cagcgacaga caggcgctcc ccgcagctcc gcacgggacc caggccgccg daccccagcg | 720 |
| ccggaccacc ctctgtccgc cccgaggagt ttgccgcctg ccggagcacc tgcgcacaga | 780 |

```
ccggtcgcca ccatgaccat ccttttcctt actatggtta tttcatactt tggttgcatg    840
aaggctgccc ccatgaaaga agcaaacatc cgaggacaag gtggcttggc ctacccaggt    900
gtgcggaccc atgggactct ggagagcgtg aatgggccca aggcaggttc aagaggcttg    960
acatcattgg ctgacacttt cgaacacgtg atagaagagc tgttggatga ggaccagaaa   1020
gttcggccca atgaagaaaa caataaggac gcagacttgt acacgtccag ggtgatgctc   1080
agtagtcaag tgcctttgga gcctcctctt ctctttctgc tggaggaata caaaaattac   1140
ctagatgctg caaacatgtc catgagggtc cggcgccact ctgaccctgc ccgccgaggg   1200
gagctgagcg tgtgtgacag tattagtgag tgggtaacgg cggcagacaa aaagactgca   1260
gtggacatgt cgggcgggac ggtcacagtc cttgaaaagg tccctgtatc aaaaggccaa   1320
ctgaagcaat acttctacga gaccaagtgc aatcccatgg gttacacaaa agaaggctgc   1380
aggggcatag acaaaaggca ttggaactcc cagtgccgaa ctacccagtc gtacgtgcgg   1440
gcccttacca tggatagcaa aaagagaatt ggctggcgat tcataaggat agacacttct   1500
tgtgtatgta cattgaccat taaaggggga agatagggta ccctgtgcct tctagttgcc   1560
agccatctgt tgtttgcccc tccccgtgc cttccttgac cctggaaggt gccactccca   1620
ctgtcctttc ctaataaaat gaggaaattg catcgcattg tctgagtagg tgtcattcta   1680
ttctgggggg tggggtgggg caggacagca aggggaagga ttgggaagac aatagcaggc   1740
atgctgggga tgcggtgggc tctatgggcg cgccatcgat gtgaagtggg taacctttat   1800
ttcccttctt tttctcttta gctcggctta ttccaggggt gtgtttcgtc gagatgcaca   1860
caagagtgag gttgctcatc ggtttaaaga tttgggagaa gaaaatttca aagccttggt   1920
gttgattgcc tttgctcagt atcttcagca gtgtccattt gaagatcatg taaaattagt   1980
gaatgaagta actgaatttg caaaaacatg tgttgctgat gagtcagctg aaaattgtga   2040
caaatcactt catacccttt ttggagacaa attatgcaca gttgcaactc ttcgtgaaac   2100
ctatggtgaa atgctgact gctgtgcaaa acaagaacct gagagaaatg aatgcttctt   2160
gcaacacaaa gatgacaacc caaacctccc ccgattggtg agaccagagg ttgatgtgat   2220
gtgcactgct tttcatgaca atgaagagac cttttgaaa aaatacttat acgaaattgc   2280
cagaagacat ccttactttt atgccccgga actccttttc tttgctaaaa ggtataaagc   2340
tgcttttaca gaatgttgcc aagctgctga taaagctgcc tgcctgttgc caaagctcga   2400
tgaacttcgg gatgaaggga aggcttcgtc tgccaaacag agactcaagt gtgccagtct   2460
ccaaaaattt ggagaaagag cttcaaagc atgggcagta gctcgcctga gccagagatt   2520
tcccaaagct gagtttgcag aagtttccaa gttagtgaca gatcttacca agtccacac   2580 ggaatgctgc catggagatc tgcttgaatg tgctgatgac agggcggacc ttgccaagta   2640
tatctgtgaa aatcaagatt cgatctccag taaactgaag gaatgctgtg aaaaacctct   2700
gttggaaaaa tcccactgca ttgccgaagt ggaaaatgat gagatgcctg ctgacttgcc   2760
ttcattagct gctgattttg ttgaaagtaa ggatgtttgc aaaaactatg ctgaggcaaa   2820
ggatgtcttc ctgggcatgt ttttgtatga atatgcaaga aggcatcctg attactctgt   2880
cgtgctgctg ctgagacttg ccaagaccta tgaaaccact ctagaagt gctgtgccgc   2940 tgcagatcct catgaatgct atgccaaagt gttcgatgaa tttaaacctc ttgtggaaga   3000
gcctcagaat ttaatcaaac aaaattgtga gcttttgag cagcttggag agtacaaatt   3060
ccagaatgcg ctattagttc gttacaccaa gaaagtaccc caagtgtcaa ctccaactct   3120
tgtagaggtc tcaagaaacc taggaaaagt gggcagcaaa tgttgtaaac atcctgaagc   3180
```

```
aaaaagaatg ccctgtgcag aagactatct atccgtggtc ctgaaccagt tatgtgtgtt    3240
gcatgagaaa acgccagtaa gtgacagagt caccaaatgc tgcacagaat ccttggtgaa    3300
caggcgacca tgtcgtgaaa cctatggtga atggctgac tgctgtgcaa aacaagaacc     3360
tgagagaaat gaatgcttct tgcaacacaa agatgacaac ccaaacctcc cccgattggt    3420
gagaccagag gttgatgtga tgtgcactgc ttttcatgac aatgaagaga ccttttttgaa   3480 aaaatactta tacgaaattg ccagaagaca tccttacttt tatgccccgg aactcctttt    3540
ctttgctaaa aggtataaag ctgcttttac agaatgttgc caagctgctg ataaagctgc    3600
ctgcctgttg ccaaagctcg atgaacttcg ggatgaaggg aaggcttcgt ctgccaaaca    3660
gagactcaag tgtgccagtc tccaaaaatt tggagaaaga gctttcaaag catgggcagt    3720
agctcgcctg agccagactt ttcagctctg gaagtcgatg aaacatacgt tcccaaagag    3780
tttaatgctg aaacattcac cttccatgca gatatatgca cactttctga aaggagaga    3840 caaatcaaga aacaaactgc acttgttgag ctcgtgaaac acaagcccaa ggcaacaaaa    3900
gagcaactga aagctgttat ggatgatttc gctcgagcca tgggcgcgcc atcgatgagg    3960 aaccccctagt gatggagttg gccactccct ctctgcgcgc tcgctcgctc actgaggccg    4020
ggcgaccaaa ggtcgcccga cgcccgggct ttgcccgggc ggcctcagtg agcgagcgag    4080
cgcgcagctg cctgcagg                                                 4098
```

<210> SEQ ID NO 5
<211> LENGTH: 4630
<212> TYPE: DNA
<213> ORGANISM: Artificial Sequence
<220> FEATURE:
<223> OTHER INFORMATION: hSARE-ArcMin-BDNF-long 3' UTR

<400> SEQUENCE: 5

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc ttgcgtcgac aggcctccta ggcggaccgc ttgcatgcag    180
ggtggtgcag agtctgcatg cgtgaggagc tcctgggcg tcacagccg cgctattctc      240 agcgtctctc cttttatggc tccggaagtg agctggggtt gctggcagcc gtccctcggt    300 cccccgcaggc tgaatgagcc ccgccgtccg gggtgggagg tacggagcgg agggattagt   360
catcctggcc ccgccatgtg tgcagggggt gggacctccc gtcccttgcc gcccgggagc    420
cgagtgggcg cagggcgggg cctgcagggg cgcgggcggg gcgctggcgg ggagcctgcg    480
gctgggccaa tgagaaaccg ggctcggcga ccggccgcc cacgggcctc gctggctgca    540
taaagagccg gcggccagga ctcagcgcag agctcgggcg cggcgtcctc cctccgcagc    600
agccgagccg gacctgcctc cccgggcgtg ctccgccggc cccgccgccg gcccgcagcg    660
acagacaggc gctccccgca gctccgcacg ggacccaggc cgccggaccc cagcgccgga    720 ccacccctctg tccgccccga ggagtttgcc gcctgccgga gcacctgcgc acagaccggt    780
cgccaccatg accatccttt tccttactat ggttatttca tactttggtt gcatgaaggc    840
tgcccccatg aaagaagcaa acatccgagg acaaggtggc ttggcctacc caggtgtgcg    900
gacccatggg actctggaga gcgtgaatgg gcccaaggca ggttcaagag gcttgacatc    960
attggctgac actttcgaac acgtgataga agagctgttg gatgaggacc agaaagttcg   1020
gcccaatgaa gaaaacaata aggacgcaga cttgtacacg tccagggtga tgctcagtag   1080
```

```
tcaagtgcct ttggagcctc ctcttctctt tctgctggag gaatacaaaa attacctaga   1140
tgctgcaaac atgtccatga gggtccggcg ccactctgac cctgcccgcc gagggagct    1200 gagcgtgtgt gacagtatta gtgagtgggt aacggcggca gacaaaaaga ctgcagtgga   1260
catgtcgggc gggacggtca cagtccttga aaaggtccct gtatcaaaag gccaactgaa   1320
gcaatacttc tacgagacca agtgcaatcc catgggttac acaaaagaag gctgcagggg   1380
catagacaaa aggcattgga actcccagtg ccgaactacc cagtcgtacg tgcgggccct   1440
taccatggat agcaaaaaga gaattggctg gcgattcata aggatagaca cttcttgtgt   1500
atgtacattg accattaaaa ggggaagata gggtacctgg atttatgttg tatagattag   1560
attatattga gacaaaaatt atctatttgt atatatacat aacagggtaa attattcagt   1620
taagaaaaaa ataattttat gaactgcatg tataaatgaa gtttatacag tacagtggtt   1680
ctacaatcta tttattggac atgtccatga ccagaaggga aacagtcatt tgcgcacaac   1740
ttaaaaagtc tgcattacat tccttgataa tgttgtggtt tgttgccgtt gccaagaact   1800
gaaaacataa aaagttaaaa aaaataataa attgcatgct gctttaattg tgaattgata   1860
ataaactgtc ctctttcaga aaacagaaaa aaacacacac acacacaaca aaaatttgaa   1920
ccaaaacatt ccgtttacat tttagacagt aagtatcttc gttcttgtta gtactatatc   1980
tgttttactg ctttttaactt ctgatagcgt tggaattaaa acaatgtcaa ggtgctgttg   2040
tcattgcttt actggcttag gggatggggg atgggggggta tattttgtt tgttttgtgt    2100 tttttttcg tttgtttgtt ttgttttttta gttcccacag ggagtagaga tggggaaaga   2160
attcctacaa tatatattct ggctgataaa agatacattt gtatgttgtg aagatgtttg   2220
caatatcgat cagatgacta gaaagtgaat aaaaattaag gcaactgaac aaaaaaatgc   2280
tcacactcca catcccgtga tgcacctccc aggcccgct cattctttgg gcgttggtca    2340
gagtaagctg cttttgacgg aaggacctat gtttgctcag aacacattct ttccccccct   2400 cccctctgg tctcctctttt gttttgtttt aaggaagaaa atcagttgc gcgttctgaa    2460 atattttacc actgctgtga acaagtgaac acattgtgtc acatcatgac actcgtataa   2520
gcatggagaa cagtgatttt tttttagaac agaaaacaac aaaaaataac cccaaaatga   2580
agattatttt ttatgaggag tgaacatttg ggtaaatcat ggctaagctt aaaaaaaact   2640
catggtgagg cttaacaatg tcttgtaagc aaaaggtaga gccctgtatc aacccagaaa   2700
cacctagatc agaacaggaa tccacattgc cagtgacatg agactgaaca gccaaatgga   2760
ggctatgtgg agttggcatt gcatttaccg gcagtgcggg aggaatttct gagtggccat   2820
cccaaggtct aggtggaggt ggggcatggt atttgagaca ttccaaaacg aaggcctctg   2880 aaggacccctt cagaggtggc tctggaatga catgtgtcaa gctgcttgga cctcgtgctt   2940
taagtgccta cattatctaa ctgtgctcaa gaggttctcg actggaggac cacactcaag   3000
ccgacttatg cccaccatcc cacctctgga taattttgca taaaattgga ttagcctgga   3060
gcaggttggg agccaaatgt ggcatttgtg atcatgagat tgatgcaatg agatagaaga   3120
tgtttgctac ctgaacactt attgctttga aactagactt gaggaaacca gggtttatct   3180
tttgagaact tttggtaagg gaaaagggaa caggaaaaga aacccaaaac tcaggccgaa   3240
tgatcaaggg gacccatagg aaatcttgtc cagagacaag acttcgggaa ggtgtctgga   3300
cattcagaac accaagactt gaaggtgcct tgctcaatgg aagaggccag gacagagctg   3360
acaaaatttt gctccccagt gaaggccaca gcaaccttct gcccatcctg tctgttcatg   3420
gagagggtcc ctgcctcacc tctgccattt tgggttagga gaagtcaagt tgggagcctg   3480
```

-continued

```
aaatagtggt tcttggaaaa atggatcccc agtgaaaact agagctctaa gcccattcag    3540
cccatttcac acctgaaaat gttagtgatc accacttgga ccagcatcct taagtatcag    3600
aaagccccaa gcaattgctg catcttagta gggtgaggga taagcaaaag aggatgttca    3660
ccataaccca ggaatgaaga taccatcagc aaagaatttc aatttgttca gtctttcatt    3720
tagagctagt ctttcacagt accatctgaa tacctctttg aaagaaggaa gactttacgt    3780
agtgtagatt tgttttgtgt tgtttgaaaa tattatcttt gtaattattt ttaatatgta    3840
aggaatgctt ggaatatctg ctatatgtca actttatgca gcttcctttt gagggacaaa    3900
tttaaaacaa acaacccccc atcacaaact taaaggattg caagggccag atctgttaag    3960
tggtttcata ggagacacat ccagcaattg tgtggtcagt ggctctttta cccaataaga    4020
tacatcacag tcacatgctt gatggtttat gttgacctaa gatttatttt gttaaaatct    4080
ctctctgttg tgttcgttct tgttctgttt tgttttgttt tttaaagtct tgctgtggtc    4140
tctttgtggc agaagtgttt catgcatggc agcaggcctg ttgctttttt atggcgattc    4200
ccattgaaaa tgtaagtaaa tgtctgtggc cttgttctct ctatggtaaa gatattattc    4260
accatgtaaa acaaaaaaca atatttattg tattttagta tatttatata attatgttat    4320
tgaaaaaaat tggcattaaa acttaaccgc atcagaacct attgtaaata caagttctat    4380
ttaagtgtac taattaacat ataatatatg ttttaaatat agaattttta atgtttttaa    4440
atatattttc aaagtacata aaactcgagc catgggcgcg ccatcgatga ggaacccta    4500 gtgatggagt tggccactcc ctctctcgcg gctcgctcgc tcactgaggc cgggcgacca    4560
aaggtcgccc gacgcccggg ctttgcccgg gcggcctcag tgagcgagcg agcgcgcagc    4620
tgcctgcagg                                                            4630
```

<210> SEQ ID NO 6
<211> LENGTH: 595
<212> TYPE: DNA
<213> ORGANISM: Artificial Sequence
<220> FEATURE:
<223> OTHER INFORMATION: hSARE-ArcMin

<400> SEQUENCE: 6

```
gggtggtgca gagtctgcat gcgtgaggag ctcctgggcg cgtcacagcc gcgctattct     60
cagcgtctct cctttttatgg ctccggaagt gagctggggt tgctggcagc cgtccctcgg    120
tccccgcagg ctgaatgagc ccgccgtcc ggggtgggag gtacggagcg gagggattag     180
tcatcctggc cccgccatgt gtgcaggggg tgggacctcc cgtcccttgc cgcccgggag    240
ccgagtgggc gcagggcggg gcctgcaggg gcgcgggcgg ggcgctggcg gggagcctgc    300
ggctgggcca atgagaaacc gggctcggcg agccggccgc ccacgggcct cgctggctgc    360
ataaagagcc ggcggccagg actcagcgca gagctcgggc gcggcgtcct ccctccgcag    420
cagccgagcc ggacctgcct ccccgggcgt gctccgccgg ccccgccgcc ggcccgcagc    480
gacagacagg cgctccccgc agctccgcac gggacccagg ccgccggacc ccagcgccgg    540
accaccctct gtccgccccg aggagtttgc cgcctgccgg agcacctgcg cacag          595
```

<210> SEQ ID NO 7
<211> LENGTH: 744
<212> TYPE: DNA
<213> ORGANISM: Artificial Sequence
<220> FEATURE:
<223> OTHER INFORMATION: BDNF

<400> SEQUENCE: 7

```
atgaccatcc ttttccttac tatggttatt tcatactttg gttgcatgaa ggctgccccc    60
atgaagaag caaacatccg aggacaaggt ggcttggcct acccaggtgt gcggacccat   120
gggactctgg agagcgtgaa tgggcccaag gcaggttcaa gaggcttgac atcattggct   180
gacactttcg aacacgtgat agaagagctg ttggatgagg accagaaagt tcggcccaat   240
gaagaaaaca ataaggacgc agacttgtac acgtccaggg tgatgctcag tagtcaagtg   300
cctttggagc ctcctcttct ctttctgctg aggaataca aaaattacct agatgctgca    360
aacatgtcca tgggtccg cgccactct gaccctgccc gccagggga gctgagcgtg       420
tgtgacagta ttagtgagtg ggtaacggcg gcagacaaaa agactgcagt ggacatgtcg   480
ggcgggacgg tcacagtcct tgaaaaggtc cctgtatcaa aggccaact gaagcaatac    540
ttctacgaga ccaagtgcaa tcccatgggt tacacaaaag aaggctgcag ggcatagac    600
aaaaggcatt ggaactccca gtgccgaact acccagtcgt acgtgcgggc ccttaccatg   660
gatagcaaaa agagaattgg ctggcgattc ataaggatag acacttcttg tgtatgtaca   720
ttgaccatta aaggggaag atag                                          744
```

<210> SEQ ID NO 8
<211> LENGTH: 327
<212> TYPE: DNA
<213> ORGANISM: Artificial Sequence
<220> FEATURE:
<223> OTHER INFORMATION: BDNF short 3' UTR

<400> SEQUENCE: 8

```
tggatttatg ttgtatagat tagattatat tgagacaaaa attatctatt tgtatatata    60
cataacaggg taaattattc agttaagaaa aaaataattt tatgaactgc atgtataaat   120
gaagtttata cagtacagtg gttctacaat ctatttattg gacatgtcca tgaccagaag   180
ggaaacagtc atttgcgcac aacttaaaaa gtctgcatta cattccttga taatgttgtg   240
gtttgttgcc gttgccaaga actgaaaaca taaaaagtta aaaaaaataa taaattgcat   300
gctgctttaa ttgtgaattg ataataa                                      327
```

<210> SEQ ID NO 9
<211> LENGTH: 225
<212> TYPE: DNA
<213> ORGANISM: Artificial Sequence
<220> FEATURE:
<223> OTHER INFORMATION: bGH poly (A)

<400> SEQUENCE: 9

```
ctgtgccttc tagttgccag ccatctgttg tttgccccte cccgtgcct tccttgaccc     60
tggaaggtgc cactcccact gtcctttcct aataaaatga ggaaattgca tcgcattgtc   120
tgagtaggtg tcattctatt ctggggggtg ggtgggca ggacagcaag ggggaggatt     180
gggaagacaa tagcaggcat gctgggatg cggtgggctc tatgg                    225
```

<210> SEQ ID NO 10
<211> LENGTH: 2926
<212> TYPE: DNA
<213> ORGANISM: Artificial Sequence
<220> FEATURE:
<223> OTHER INFORMATION: BDNF long 3' UTR

<400> SEQUENCE: 10

```
tggatttatg ttgtatagat tagattatat tgagacaaaa attatctatt tgtatatata        60
cataacaggg taaattattc agttaagaaa aaaataattt tatgaactgc atgtataaat       120
gaagtttata cagtacagtg gttctacaat ctatttattg gacatgtcca tgaccagaag       180
ggaaacagtc atttgcgcac aacttaaaaa gtctgcatta cattccttga taatgttgtg       240
gtttgttgcc gttgccaaga actgaaaaca taaaaagtta aaaaaaataa taaattgcat       300
gctgctttaa ttgtgaattg ataataaact gtcctctttc agaaaacaga aaaaaacaca       360
cacacacaca acaaaaattt gaaccaaaac attccgttta cattttagac agtaagtatc       420
ttcgttcttg ttagtactat atctgtttta ctgcttttaa cttctgatag cgttggaatt       480
aaaacaatgt caaggtgctg ttgtcattgc tttactggct taggggatgg gggatggggg       540
gtatatttt gtttgttttg tgtttttttt tcgtttgttt gttttgtttt ttagttccca       600
cagggagtag agatggggaa agaattccta caatatatat tctggctgat aaagataca       660
tttgtatgtt gtgaagatgt ttgcaatatc gatcagatga ctagaaagtg aataaaaatt       720
aaggcaactg aacaaaaaaa tgctcacact ccacatcccg tgatgcacct cccaggcccc       780
gctcattctt tgggcgttgg tcagagtaag ctgcttttga cggaaggacc tatgtttgct       840
cagaacacat tctttccccc cctccccctc tggtctcctc tttgttttgt tttaaggaag       900
aaaaatcagt tgcgcgttct gaaatatttt accactgctg tgaacaagtg aacacattgt       960
gtcacatcat gacactcgta taagcatgga gaacagtgat ttttttttag aacagaaaac      1020
aacaaaaaat aaccccaaaa tgaagattat tttttatgag gagtgaacat ttgggtaaat      1080
catggctaag cttaaaaaaa actcatggtg aggcttaaca atgtcttgta agcaaaaggt      1140
agagccctgt atcaacccag aaacacctag atcagaacag gaatccacat tgccagtgac      1200
atgagactga acagccaaat ggaggctatg tggagttggc attgcattta ccggcagtgc      1260
gggaggaatt tctgagtggc catcccaagg tctaggtgga ggtggggcat ggtatttgag      1320
acattccaaa acgaaggcct ctgaaggacc cttcagaggt ggctctggaa tgacatgtgt      1380
caagctgctt ggacctcgtg cttaagtgc ctacattatc taactgtgct caagaggttc      1440
tcgactggag gaccacactc aagccgactt atgcccacca tcccacctct ggataatttt      1500
gcataaaatt ggattagcct ggagcaggtt gggagccaaa tgtggcattt gtgatcatga      1560
gattgatgca atgagataga agatgtttgc tacctgaaca cttattgctt tgaaactaga      1620
cttgaggaaa ccagggttta tcttttgaga acttttggta agggaaaagg gaacaggaaa      1680
agaaaccccca aactcaggcc gaatgatcaa ggggacccat aggaaatctt gtccagagac      1740
aagacttcgg gaaggtgtct ggacattcag aacaccaaga cttgaaggtg ccttgctcaa      1800
tggaagaggc caggacagag ctgacaaaat tttgctcccc agtgaaggcc acagcaacct      1860
tctgcccatc ctgtctgttc atggagaggg tccctgcctc acctctgcca ttttgggtta      1920
ggagaagtca agttgggagc ctgaaatagt ggttcttgga aaaatggatc cccagtgaaa      1980
actagagctc taagcccatt cagcccattt cacacctgaa aatgttagtg atcaccactt      2040
ggaccagcat ccttaagtat cagaaagccc caagcaattg ctgcatctta gtagggtgag      2100
ggataagcaa aagaggatgt tcaccataac ccaggaatga agataccatc agcaaagaat      2160
ttcaatttgt tcagtctttc atttagagct agtcttccac agtaccatct gaatacctct      2220
ttgaaagaag gaagacttta cgtagtgtag atttgttttg tgttgtttga aaatattatc      2280
```

```
tttgtaatta tttttaatat gtaaggaatg cttggaatat ctgctatatg tcaactttat    2340
gcagcttcct tttgagggac aaatttaaaa caaacaaccc cccatcacaa acttaaagga    2400
ttgcaagggc cagatctgtt aagtggtttc ataggagaca catccagcaa ttgtgtggtc    2460
agtggctctt ttacccaata agatacatca cagtcacatg cttgatggtt tatgttgacc    2520
taagatttat tttgttaaaa tctctctctg ttgtgttcgt tcttgttctg ttttgttttg    2580
ttttttaaag tcttgctgtg gtctctttgt ggcagaagtg tttcatgcat ggcagcaggc    2640
ctgttgcttt tttatggcga ttcccattga aaatgtaagt aaatgtctgt ggccttgttc    2700
tctctatggt aaagatatta ttcaccatgt aaaacaaaaa acaatatttta ttgtatttta    2760 gtatatttat ataattatgt tattgaaaaa aattggcatt aaaacttaac cgcatcagaa    2820
cctattgtaa atacaagttc tatttaagtg tactaattaa catataatat atgttttaaa    2880
tatagaattt ttaatgtttt taaatatatt ttcaaagtac ataaaa                   2926
```

<210> SEQ ID NO 11
<211> LENGTH: 111
<212> TYPE: DNA
<213> ORGANISM: Artificial Sequence
<220> FEATURE:
<223> OTHER INFORMATION: hSARE
<220> FEATURE:
<221> NAME/KEY: misc_feature
<222> LOCATION: (40)..(49)
<223> OTHER INFORMATION: cAMP response element
<220> FEATURE:
<221> NAME/KEY: misc_feature
<222> LOCATION: (53)..(63)
<223> OTHER INFORMATION: MEF2 binding site
<220> FEATURE:
<221> NAME/KEY: misc_feature
<222> LOCATION: (69)..(88)
<223> OTHER INFORMATION: Serum Response Element

<400> SEQUENCE: 11

```
gggtggtgca gagtctgcat gcgtgaggag ctcctgggcg cgtcacagcc gcgctattct     60
cagcgtctct cctttatgg ctccggaagt gagctggggt tgctggcagc c               111
```

<210> SEQ ID NO 12
<211> LENGTH: 484
<212> TYPE: DNA
<213> ORGANISM: Artificial Sequence
<220> FEATURE:
<223> OTHER INFORMATION: hArcMin

<400> SEQUENCE: 12

```
gtccctcggt ccccgcaggc tgaatgagcc ccgccgtccg gggtgggagg tacggagcgg     60
agggattagt catcctggcc ccgccatgtg tgcaggggt gggacctccc gtcccttgcc     120
gcccgggagc cgagtgggcg cagggcgggg cctgcagggg cgcgggcggg gcgctggcgg    180
ggagcctgcg gctgggccaa tgagaaaccg ggctcggcga gccggccgcc cacgggcctc    240
gctggctgca taaagagccg gcggccagga ctcagcgcag agctcgggcg cggcgtcctc    300
cctccgcagc agccgagccg gacctgcctc cccgggcgtg ctccgccggc ccgccgccg    360 gcccgcagcg acagacaggc gctccccgca gctccgcacg ggacccaggc cgccggaccc    420
cagcgccgga ccaccctctg tccgccccga ggagtttgcc gcctgccgga gcacctgcgc    480
acag                                                                  484
```

<210> SEQ ID NO 13
<211> LENGTH: 2165

<212> TYPE: DNA
<213> ORGANISM: Artificial Sequence
<220> FEATURE:
<223> OTHER INFORMATION: hAlbumin stuffer sequence

<400> SEQUENCE: 13

```
gcgcgccatc gatgtgaagt gggtaacctt tatttccctt cttttctct  ttagctcggc      60
ttattccagg ggtgtgtttc gtcgagatgc acacaagagt gaggttgctc atcggtttaa     120
agatttggga gaagaaaatt tcaaagcctt ggtgttgatt gcctttgctc agtatcttca     180
gcagtgtcca tttgaagatc atgtaaaatt agtgaatgaa gtaactgaat tgcaaaaac     240
atgtgttgct gatgagtcag ctgaaaattg tgacaaatca cttcataccc ttttggaga     300
caaattatgc acagttgcaa ctcttcgtga aacctatggt gaaatggctg actgctgtgc     360
aaaacaagaa cctgagagaa atgaatgctt cttgcaacac aaagatgaca cccaaacct     420
cccccgattg gtgagaccag aggttgatgt gatgtgcact gcttttcatg acaatgaaga     480
gacctttttg aaaaaatact tatacgaaat tgccagaaga catccttact tttatgcccc     540
ggaactcctt ttctttgcta aaaggtataa agctgctttt acagaatgtt gccaagctgc     600
tgataaagct gcctgcctgt tgccaaagct cgatgaactt cgggatgaag ggaaggcttc     660
gtctgccaaa cagagactca gtgtgccag tctccaaaaa tttggagaaa gagctttcaa     720
agcatgggca gtagctcgcc tgagccagag atttcccaaa gctgagtttg cagaagtttc     780
caagttagtg acagatctta ccaaagtcca cacggaatgc tgccatggag atctgcttga     840
atgtgctgat gacagggcgg accttgccaa gtatatctgt gaaaatcaag attcgatctc     900
cagtaaactg aaggaatgct gtgaaaaacc tctgttggaa aaatcccact gcattgccga     960
agtggaaaat gatgagatgc ctgctgactt gccttcatta gctgctgatt tgttgaaag   1020
taaggatgtt tgcaaaaact atgctgaggc aaaggatgtc ttcctgggca tgtttttgta   1080
tgaatatgca agaaggcatc ctgattactc tgtcgtgctg ctgctgagac ttgccaagac   1140
ctatgaaacc actctagaga agtgctgtgc cgctgcagat cctcatgaat gctatgccaa   1200
agtgttcgat gaatttaaac ctcttgtgga agagcctcag aatttaatca acaaaattg   1260
tgagctttt  gagcagcttg gagagtacaa attccagaat gcgctattag ttcgttacac   1320
caagaaagta ccccaagtgt caactccaac tcttgtagag gtctcaagaa acctaggaaa   1380
agtgggcagc aaatgttgta acatcctga  agcaaaaaga atgccctgtg cagaagacta   1440
tctatccgtg gtcctgaacc agttatgtgt gttgcatgaa aaaacgccag taagtgacag   1500
agtcaccaaa tgctgcacag aatccttggt gaacaggcga ccatgtcgtg aaacctatgg   1560
tgaaatggct gactgctgtg caaaacaaga acctgagaga atgaatgct  tcttgcaaca   1620
caaagatgac aacccaaacc tccccgatt  ggtgagacca gaggttgatg tgatgtgcac   1680
tgcttttcat gacaatgaag agaccttttt gaaaaaatac ttatacgaaa ttgccagaag   1740
acatccttac ttttatgccc cggaactcct tttctttgct aaaaggtata agctgctttt   1800
tacagaatgt tgccaagctg ctgataaagc tgcctgcctg ttgccaaagc tcgatgaact   1860
tcgggatgaa gggaaggctt cgtctgccaa acagagactc aagtgtgcca gtctccaaaa   1920
atttggagaa agagctttca aagcatgggc agtagctcgc ctgagccaga cttttcagct   1980
ctggaagtcg atgaaacata cgttcccaaa gagtttaatg ctgaaacatt caccttccat   2040
```
gcagatatat gcacacttc tgagaaggag agacaaatca agaaacaaac tgcacttgtt    2100
gagctcgtga acacaagcc caaggcaaca aaagagcaac tgaaagctgt tatggatgat    2160
ttcgc                                                                2165

<210> SEQ ID NO 14
<211> LENGTH: 12
<212> TYPE: DNA
<213> ORGANISM: Artificial Sequence
<220> FEATURE:
<223> OTHER INFORMATION: Kozak sequence

<400> SEQUENCE: 14
acccggagca gc                                                          12

<210> SEQ ID NO 15
<211> LENGTH: 9
<212> TYPE: DNA
<213> ORGANISM: Artificial Sequence
<220> FEATURE:
<223> OTHER INFORMATION: Kozak sequence

<400> SEQUENCE: 15 acagccacc                                                               9

<210> SEQ ID NO 16
<211> LENGTH: 1039
<212> TYPE: DNA
<213> ORGANISM: Artificial Sequence
<220> FEATURE:
<223> OTHER INFORMATION: E-SARE-ArcMin sequence

<400> SEQUENCE: 16
gggtggtgca gagtctgcat gcgtgaggag ctcctgggcg cgtcacagcc gcgctattct      60
cagcgtctct cctttatgg ctccggaagt gagctgggt tgctggcagc cgggtggtgc      120
agagtctgca tgcgtgagga gctcctgggc gcgtcacagc cgcgctattc tcagcgtctc    180 tcctttatg gctccggaag tgagctgggg ttgctggcag ccgggtggtg cagagtctgc    240
atgcgtgagg agctcctggg cgcgtcacag ccgcgctatt tcagcgtct ctccttttat    300 ggctccggaa gtgagctggg gttgctggca gccgggtggt gcagagtctg catgcgtgag    360
gagctcctgg gcgcgtcaca gccgcgctat tctcagcgtc tctcctttta ggctccgga    420 agtgagctgg ggttgctggc agccgggtgg tgcagagtct gcatgcgtga ggagctcctg    480
ggcgcgtcac agccgcgcta ttctcagcgt ctctcctttt atggctccgg aagtgagctg    540
gggttgctgg cagccgtccc tcggtccccg caggctgaat gagccccgcc gtccggggtg    600
gaaggtacgg agcggaggga ttagtcatcc tggccccgcc atgtgtgcag gggtgggac    660 ctcccgtccc ttgccgcccg ggagccgagt gggcgcaggg cggggcctgc aggggcgcgg    720
gcggggcgct ggcggggagc ctgcggctgg gccaatgaga aaccgggctc ggcgagccgg    780
ccgcccacgg gcctcgctgg ctgcataaag agccggcggc caggactcag cgcagagctc    840
gggcgcggcg tcctccctcc gcagcagccg agccggacct gcctcccgg gcgtgctccg    900 ccggccccgc cgccggcccg cagcgacaga caggcgctcc ccgcagctcc gcacgggacc    960
caggccgccg gacccagcg ccggaccacc ctctgtccgc cccgaggagt ttgccgcctg    1020
ccggagcacc tgcgcacag                                                1039

<210> SEQ ID NO 17

```
<211> LENGTH: 278
<212> TYPE: DNA
<213> ORGANISM: Artificial Sequence
<220> FEATURE:
<223> OTHER INFORMATION: promoter sequence

<400> SEQUENCE: 17
tcgaggtgag ccccacgttc tgcttcactc tccccatctc cccccctcc ccacccccaa      60 ttttgtattt atttattttt taattatttt gtgcagcgat gggggcgggg ggggggggg     120 ggcgcgcgcc aggcggggcg gggcggggcg aggggcgggg cggggcgagg cggagaggtg    180
cggcggcagc caatcagagc ggcgcgctcc gaaagtttcc ttttatggcg aggcggcggc    240
ggcggcggcc ctataaaaag cgaagcgcgc ggcgggcg                            278

<210> SEQ ID NO 18
<211> LENGTH: 240
<212> TYPE: DNA
<213> ORGANISM: Artificial Sequence
<220> FEATURE:
<223> OTHER INFORMATION: promoter sequence

<400> SEQUENCE: 18
cggctggggc tgagggtgag ggtcccgttt ccccaaaggc ctagcctggg gttccagcca     60
caagccctac cgggcagcgc ccggccccgc ccctccaggc ctggcactcg tcctcaacca    120
agatggcgcg gatggcttca ggcgcatcac gacaccggcg cgtcacgcga cccgccctac    180
gggcacctcc cgcgcttttc ttagcgccgc agacggtggc cgagcggggg accgggaagc    240

<210> SEQ ID NO 19
<211> LENGTH: 379
<212> TYPE: DNA
<213> ORGANISM: Artificial Sequence
<220> FEATURE:
<223> OTHER INFORMATION: promoter sequence

<400> SEQUENCE: 19
attcctgctg ggaaaagcaa gtggaggtgc tccttgaaga aacaggggga tcccaccgat     60
ctcaggggtt ctgttctggc ctgcggccct ggatcgtcca gcctgggtcg gggtggggag    120
cagacctcgc ccttatcggc tggggctgag ggtgagggtc ccgtttcccc aaaggcctag    180
cctggggttc cagccacaag ccctaccggg cagcgcccgg ccccgcccct ccaggcctgg    240
cactcgtcct caaccaagat ggcgcggatg gcttcaggcg catcacgaca ccggcgcgtc    300
acgcgacccg ccctacgggc acctcccgcg cttttcttag cgccgcagac ggtggtcgag    360
cgggggaccg ggaagctta                                                 379

<210> SEQ ID NO 20
<211> LENGTH: 146
<212> TYPE: DNA
<213> ORGANISM: Artificial Sequence
<220> FEATURE:
<223> OTHER INFORMATION: promoter sequence

<400> SEQUENCE: 20
atgacacaaa ccccgcccag cgtcttgtca ttggcgaatt cgaacacgca gatgcagtcg     60
gggcggcgcg gtcccaggtc cacttcgcat attaaggtga cgcgtgtggc ctcgaacacc    120
gagcgaccct gcagcgaccc gcttaa                                         146

<210> SEQ ID NO 21
<211> LENGTH: 301
```

<212> TYPE: DNA
<213> ORGANISM: Artificial Sequence
<220> FEATURE:
<223> OTHER INFORMATION: enhancer sequence

<400> SEQUENCE: 21

```
tacataactt acggtaaatg gcccgcctgg ctgaccgccc aacgaccccc gcccattgac    60
gtcaataatg acgtatgttc ccatagtaac gccaatagg  actttccatt gacgtcaatg   120
ggtggagtat ttacggtaaa ctgcccactt ggcagtacat caagtgtatc atatgccaag   180
tacgccccct attgacgtca atgacggtaa atggcccgcc tggcattatg cccagtacat   240
gaccttatgg gactttccta cttggcagta catctacgta ttagtcatcg ctattaccat   300
g                                                                  301
```

<210> SEQ ID NO 22
<211> LENGTH: 122
<212> TYPE: DNA
<213> ORGANISM: Artificial Sequence
<220> FEATURE:
<223> OTHER INFORMATION: poly A signal

<400> SEQUENCE: 22

```
taagatacat tgatgagttt ggacaaacca caactagaat gcagtgaaaa aaatgcttta    60
tttgtgaaat ttgtgatgct attgctttat ttgtaaccat tataagctgc aataaacaag   120
tt                                                                  122
```

<210> SEQ ID NO 23
<211> LENGTH: 56
<212> TYPE: DNA
<213> ORGANISM: Artificial Sequence
<220> FEATURE:
<223> OTHER INFORMATION: poly A signal

<400> SEQUENCE: 23

```
aataaaggaa atttattttc attgcaatag tgtgttggaa ttttttgtgt ctctca        56
```

<210> SEQ ID NO 24
<211> LENGTH: 97
<212> TYPE: DNA
<213> ORGANISM: Artificial Sequence
<220> FEATURE:
<223> OTHER INFORMATION: intronic sequence

<400> SEQUENCE: 24

```
gtaagtttag tcttttttgtc ttttatttca ggtcccggat ccggtggtgg tgcaaatcaa   60
agaactgctc ctcagtggat gttgccttta cttctag                             97
```

<210> SEQ ID NO 25
<211> LENGTH: 133
<212> TYPE: DNA
<213> ORGANISM: Artificial Sequence
<220> FEATURE:
<223> OTHER INFORMATION: intronic sequence

<400> SEQUENCE: 25

```
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                     133
```

<210> SEQ ID NO 26

```
<211> LENGTH: 4008
<212> TYPE: DNA
<213> ORGANISM: Artificial Sequence
<220> FEATURE:
<223> OTHER INFORMATION: C-mScar-shortUTR

<400> SEQUENCE: 26
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgcgtcgac aggcctccta ggcggaccgc ttgcatgcac    180
gcgtagtgca agtgggtttt aggaccagga tgaggcgggg tggggggtgcc tacctgacga    240
ccgaccccga cccactggac aagcacccaa cccccattcc ccaaattgcg catcccctat     300
cagagagggg gagggggaaac aggatgcggc gaggcgcgtg cgcactgcca gcttcagcac    360
cgcggacagt gccttcgccc ccgcctggcg gcgcgcgcca ccgccgcctc agcactgaag     420
gcgcgctgac gtcactcgcc ggtccccgc aaactccct tcccggccac cttggtcgcg       480
tccgcgccgc cgccggccca gccggaccgc accacgcgag gcgcgagata gggggggcacg    540
ggcgcgacca tctgcgctgc ggcgccggcg actcagcgct gcctcagtct gcggtgggca     600
gcggaggagt cgtgtcgtgc ctgagagcgc agaccggtcg ccaccatggt gagcaagggc     660
gaggcagtga tcaaggagtt catgcggttc aaggtgcaca tggagggctc catgaacggc     720
cacgagttcg agatcgaggg cgagggcgag ggccgcccct acgagggcac ccagaccgcc     780
aagctgaagg tgaccaaggg tggccccctg cccttctcct gggacatcct gtcccctcag     840
ttcatgtacg gctccagggc cttcatcaag caccccgccg acatccccga ctactataag     900
cagtccttcc ccgagggctt caagtgggag cgcgtgatga cttcgagga cggcggcgcc      960
gtgaccgtga cccaggacac ctccctggag acggcaccc tgatctacaa ggtgaagctc     1020
cgcggcacca acttccctcc tgacggcccc gtaatgcaga agaagacaat gggctgggaa    1080
gcgtccaccg agcggttgta ccccgaggac ggcgtgctga agggcgacat taagatggcc    1140
ctgcgcctga aggacggcgg ccgctacctg gcggacttca gaccaccta caaggccaag    1200
aagcccgtgc agatgcccgg cgcctacaac gtcgaccgca agttggacat cacctcccac    1260
aacgaggact acaccgtggt ggaacagtac gaacgctccg agggccgcca ctccaccggc    1320
ggcatggacg agctgtacaa gtagggtacc tggatttatg ttgtatagat tagattatat    1380
tgagacaaaa attatctatt tgtatatata cataacaggg taaattattc agttaagaaa    1440
aaaataattt tatgaactgc atgtataaat gaagtttata cagtacagtg ttctacaat    1500
ctatttattg gacatgtcca tgaccagaag ggaaacagtc atttgcgcac aacttaaaaa    1560
gtctgcatta cattccttga taatgttgtg gtttgttgcc gttgccaaga actgaaaaca    1620
taaaagtta aaaaaaataa taaattgcat gctgctttaa ttgtgaattg ataataagcg    1680
cgccatcgat gtgaagtggg taacctttat ttcccttctt tttctcttta gctcggctta    1740
ttccaggggt gtgtttcgtc gagatgcaca caagagtgag gttgctcatc ggtttaaaga    1800
tttgggagaa gaaaatttca aagccttggt gttgattgcc tttgctcagt atcttcagca    1860
gtgtccattt gaagatcatg taaaattagt gaatgaagta actgaatttg caaaaacatg    1920
tgttgctgat gagtcagctg aaaattgtga caaatcactt catacccttt ttggagacaa    1980
attatgcaca gttgcaactc ttcgtgaaac ctatggtgaa atggctgact gctgtgcaaa    2040
acaagaacct gagagaaatg aatgcttctt gcaacacaaa gatgacaacc caaacctccc    2100
ccgattggtg agaccagagg ttgatgtgat gtgcactgct tttcatgaca atgaagagac    2160
```

```
cttttgaaa aaatacttat acgaaattgc cagaagacat ccttactttt atgccccgga    2220
actccttttc tttgctaaaa ggtataaagc tgcttttaca gaatgttgcc aagctgctga   2280
taaagctgcc tgcctgttgc caaagctcga tgaacttcgg gatgaaggga aggcttcgtc  2340
tgccaaacag agactcaagt gtgccagtct ccaaaaattt ggagaaagag ctttcaaagc  2400
atgggcagta gctcgcctga gccagagatt tcccaaagct gagtttgcag aagtttccaa  2460
gttagtgaca gatcttacca aagtccacac ggaatgctgc catggagatc tgcttgaatg  2520
tgctgatgac agggcggacc ttgccaagta tatctgtgaa atcaagatt cgatctccag   2580 taaactgaag gaatgctgtg aaaaacctct gttggaaaaa tcccactgca ttgccgaagt  2640
ggaaaatgat gagatgcctg ctgacttgcc ttcattagct gctgattttg ttgaaagtaa  2700
ggatgtttgc aaaaactatg ctgaggcaaa ggatgtcttc ctgggcatgt ttttgtatga  2760
atatgcaaga aggcatcctg attactctgt cgtgctgctg ctgagacttg ccaagaccta  2820
tgaaaccact ctagagaagt gctgtgccgc tgcagatcct catgaatgct atgccaaagt  2880
gttcgatgaa tttaaacctc ttgtggaaga gcctcagaat ttaatcaaac aaaattgtga  2940 gcttttgag cagcttggag agtacaaatt ccagaatgcg ctattagttc gttacaccaa   3000
gaaagtaccc caagtgtcaa ctccaactct tgtagaggtc tcaagaaacc taggaaaagt  3060
gggcagcaaa tgttgtaaac atcctgaagc aaaaagaatg ccctgtgcag aagactatct  3120
atccgtggtc ctgaaccagt tatgtgtgtt gcatgagaaa acgccagtaa gtgacagagt  3180
caccaaatgc tgcacagaat ccttggtgaa caggcgacca tgtcgtgaaa cctatggtga  3240
aatggctgac tgctgtgcaa aacaagaacc tgagagaaat gaatgcttct tgcaacacaa  3300
agatgacaac ccaaacctcc cccgattggt gagaccagag gttgatgtga tgtgcactgc  3360
ttttcatgac aatgaagaga ccttttgaa aaaatactta tacgaaattg ccagaagaca   3420
tccttacttt tatgccccgg aactcctttt ctttgctaaa aggtataaag ctgcttttac  3480
agaatgttgc caagctgctg ataaagctgc ctgcctgttg ccaaagctcg atgaacttcg  3540
ggatgaaggg aaggcttcgt ctgccaaaca gagactcaag tgtgccagtc tccaaaaatt  3600
tggagaaaga gctttcaaag catgggcagt agctcgcctg agccagactt tcagctctg   3660 gaagtcgatg aaacatacgt tcccaaagag tttaatgctg aaacattcac cttccatgca  3720
gatatatgca cactttctga aaggagaga caaatcaaga aacaaactgc acttgttgag   3780
ctcgtgaaac acaagcccaa ggcaacaaaa gagcaactga aagctgttat ggatgatttc  3840
gctcgagcca tgggcgcgcc atcgatgagg aaccccctagt gatggagttg gccactccct  3900
ctctgcgcgc tcgctcgctc actgaggccg ggcgaccaaa ggtcgcccga cgcccgggct  3960
ttgcccgggc ggcctcagtg agcgagcgag cgcgcagctg cctgcagg             4008
```

<210> SEQ ID NO 27
<211> LENGTH: 4443
<212> TYPE: DNA
<213> ORGANISM: Artificial Sequence
<220> FEATURE:
<223> OTHER INFORMATION: C-mScar-longUTR

<400> SEQUENCE: 27

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca  120
actccatcac taggggttcc ttgcgtcgac aggcctccta ggcggaccgc ttgcatgcac  180
```

```
gcgtagtgca agtgggtttt aggaccagga tgaggcgggg tggggggtgcc tacctgacga    240 ccgaccccga cccactggac aagcacccaa cccccattcc ccaaattgcg catccctat     300 cagagagggg gagggggaaac aggatgcggc gaggcgcgtg cgcactgcca gcttcagcac   360
cgcggacagt gccttcgccc ccgcctggcg gcgcgcgcca ccgccgcctc agcactgaag    420
gcgcgctgac gtcactcgcc ggtccccgc aaactcccct tcccggccac cttggtcgcg     480
tccgcgccgc cgccggccca gccggaccgc accacgcgag gcgcgagata gggggcacg    540 ggcgcgacca tctgcgctgc ggcgccggcg actcagcgct gcctcagtct gcggtgggca   600
gcggaggagt cgtgtcgtgc ctgagagcgc agaccggtcg ccaccatggt gagcaagggc   660
gaggcagtga tcaaggagtt catgcggttc aaggtgcaca tggagggctc catgaacggc   720
cacgagttcg agatcgaggg cgagggcgag ggccgcccct acgagggcac ccagaccgcc   780
aagctgaagg tgaccaaggg tggcccctg cccttctcct gggacatcct gtcccctcag    840
ttcatgtacg gctccaggc cttcatcaag caccccgccg acatcccga ctactataag      900 cagtccttcc ccgagggctt caagtgggag cgcgtgatga cttcgagga cggcggcgcc    960 gtgaccgtga cccaggacac ctccctggag gacggcaccc tgatctacaa ggtgaagctc  1020
cgcggcacca acttccctcc tgacggcccc gtaatgcaga agaagacaat gggctgggaa  1080
gcgtccaccg agcggttgta ccccgaggac ggcgtgctga gggcgacat taagatggcc   1140 ctgcgcctga aggacggcgg ccgctacctg gcggacttca agaccaccta caaggccaag  1200
aagcccgtgc agatgcccgg cgcctacaac gtcgaccgca agttggacat cacctcccac  1260
aacgaggact acaccgtggt ggaacagtac gaacgctccg agggccgcca ctccaccggc  1320
ggcatggacg agctgtacaa gtagggtacc tggatttatg ttgtatagat tagattatat  1380
tgagacaaaa attatctatt tgtatatata cataacaggg taaattattc agttaagaaa  1440
aaaataattt tatgaactgc atgtataaat gaagtttata cagtacagtg gttctacaat  1500
ctatttattg gacatgtcca tgaccagaag ggaaacagtc attttgcgcac aacttaaaaa  1560 gtctgcatta cattccttga taatgttgtg gtttgttgcc gttgccaaga actgaaaaca  1620
taaaaagtta aaaaaaataa taaattgcat gctgctttaa ttgtgaattg ataataaact  1680
gtcctctttc agaaaacaga aaaaaacaca cacacacaca acaaaaattt gaaccaaaac  1740
attccgttta cattttagac agtaagtatc ttcgttcttg ttagtactat atctgtttta  1800
ctgcttttaa cttctgatag cgttggaatt aaaacaatgt caaggtgctg ttgtcattgc  1860
tttactggct tagggatgg gggatgggg gtatattttt gtttgttttg tgttttttt    1920 tcgtttgttt gttttgtttt ttagttccca cagggagtag agatgggaa agaattccta   1980 caatatatat tctggctgat aaagataca tttgtatgtt gtgaagatgt ttgcaatatc   2040
gatcagatga ctagaaagtg aataaaaatt aaggcaactg aacaaaaaaa tgctcacact  2100
ccacatcccg tgatgcacct cccaggcccc gctcattctt tgggcgttgg tcagagtaag  2160
ctgcttttga cggaaggacc tatgtttgct cagaacacat tctttccccc cctccccctc  2220
tggtctcctc tttgtttgt tttaaggaag aaaaatcagt tgcgcgttct gaaatatttt   2280
accactgctg tgaacaagtg aacacattgt gtcacatcat gacactcgta taagcatgga  2340
gaacagtgat tttttttag aacagaaaac aacaaaaaat aaccccaaaa tgaagattat   2400 ttttatgag gagtgaacat ttgggtaaat catggctaag cttaaaaaaa actcatggtg   2460
aggcttaaca atgtcttgta agcaaaaggt agagccctgt atcaacccag aaacacctag  2520
atcagaacag gaatccacat tgccagtgac atgagactga acagccaaat ggaggctatg  2580
```

```
tggagttggc attgcattta ccggcagtgc gggaggaatt tctgagtggc catcccaagg    2640
tctaggtgga ggtggggcat ggtatttgag acattccaaa acgaaggcct ctgaaggacc    2700
cttcagaggt ggctctggaa tgacatgtgt caagctgctt ggacctcgtg ctttaagtgc    2760
ctacattatc taactgtgct caagaggttc tcgactggag gaccacactc aagccgactt    2820
atgcccacca tcccacctct ggataatttt gcataaaatt ggattagcct ggagcaggtt    2880
gggagccaaa tgtggcattt gtgatcatga gattgatgca atgagataga agatgtttgc    2940
tacctgaaca cttattgctt tgaaactaga cttgaggaaa ccagggttta tcttttgaga    3000
acttttggta agggaaaagg gaacaggaaa agaaacccca aactcaggcc gaatgatcaa    3060
ggggacccat aggaaatctt gtccagagac aagacttcgg gaaggtgtct ggacattcag    3120
aacaccaaga cttgaaggtg ccttgctcaa tggaagaggc caggacagag ctgacaaaat    3180
tttgctcccc agtgaaggcc acagcaacct tctgcccatc ctgtctgttc atggagaggg    3240
tccctgcctc acctctgcca ttttgggtta ggagaagtca agttgggagc tgaaatagt     3300 ggttcttgga aaaatggatc cccagtgaaa actagagctc taagcccatt cagcccattt    3360
cacacctgaa aatgttagtg atcaccactt ggaccagcat ccttaagtat cagaaagccc    3420
caagcaattg ctgcatctta gtagggtgag ggataagcaa aagaggatgt tcaccataac    3480
ccaggaatga agataccatc agcaaagaat ttcaatttgt tcagtctttc atttagagct    3540
agtctttcac agtaccatct gaataccct  ttgaagaag gaagacttta cgtagtgtag    3600 attttgtttttg tgttgtttga aaatattatc tttgtaatta tttttaatat gtaaggaatg    3660
cttggaatat ctgctatatg tcaactttat gcagcttcct tttgagggac aaatttaaaa    3720
caaacaaccc cccatcacaa acttaaagga ttgcaagggc cagatctgtt aagtggtttc    3780
ataggagaca catccagcaa ttgtgtggtc agtggctctt ttacccaata agatacatca    3840
cagtcacatg cttgatggtt tatgttgacc taagatttat tttgttaaaa tctctctctg    3900
ttgtgttcgt tcttgttctg ttttgttttg ttttttaaag tcttgctgtg gtctctttgt    3960
ggcagaagtg tttcatgcat ggcagcaggc ctgttgcttt tttatggcga ttcccattga    4020
aaatgtaagt aaatgtctgt ggccttgttc tctctatggt aaagatatta ttcaccatgt    4080
aaaacaaaaa acaatatttta ttgtatttta gtatatttat ataattatgt tattgaaaaa    4140
aattggcatt aaaacttaac cgcatcagaa cctattgtaa atacaagttc tatttaagtg    4200
tactaattaa catataatat atgttttaaa tatagaattt ttaatgtttt taaatatatt    4260
ttcaaagtac ataaaactcg agccatgggc gcgccatcga tgaggaaccc ctagtgatgg    4320
agttggccac tccctctctg cgcgctcgct cgctcactga ggccgggcga ccaaaggtcg    4380
cccgacgccc gggctttgcc cgggcggcct cagtgagcga gcgagcgcgc agctgcctgc    4440
agg                                                                  4443
```

<210> SEQ ID NO 28
<211> LENGTH: 3906
<212> TYPE: DNA
<213> ORGANISM: Artificial Sequence
<220> FEATURE:
<223> OTHER INFORMATION: C-mScar-bGH

<400> SEQUENCE: 28

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
```

| | |
|---|---|
| actccatcac tagggggttcc ttgcgtcgac aggcctccta ggcggaccgc ttgcatgcac | 180 |
| gcgtagtgca agtgggtttt aggaccagga tgaggcgggg tgggggtgcc tacctgacga | 240 |
| ccgaccccga cccactggac aagcacccaa cccccattcc ccaaattgcg catccctat | 300 |
| cagagagggg gagggaaaac aggatgcggc gaggcgcgtg cgcactgcca gcttcagcac | 360 |
| cgcggacagt gccttcgccc ccgcctggcg gcgcgcgcca ccgccgcctc agcactgaag | 420 |
| gcgcgctgac gtcactcgcc ggtccccgc aaactcccct tcccggccac cttggtcgcg | 480 |
| tccgcgccgc cgcggccca gccggaccgc accacgcgag gcgcgagata gggggcacg | 540 |
| ggcgcgacca tctgcgctgc ggcgccggcg actcagcgct gcctcagtct gcggtgggca | 600 |
| gcggaggagt cgtgtcgtgc ctgagagcgc agaccggtcg ccaccatggt gagcaagggc | 660 |
| gaggcagtga tcaaggagtt catgcggttc aaggtgcaca tggagggctc catgaacggc | 720 |
| cacgagttcg agatcgaggg cgaggcgag ggccgcccct acgagggcac ccagaccgcc | 780 |
| aagctgaagg tgaccaaggg tggccccctg cccttctcct gggacatcct gtcccctcag | 840 |
| ttcatgtacg gctccagggc cttcatcaag caccccgccg acatccccga ctactataag | 900 |
| cagtccttcc ccgagggctt caagtgggag cgcgtgatga cttcgagga cggcggcgcc | 960 |
| gtgaccgtga cccaggacac ctccctggag gacggcaccc tgatctacaa ggtgaagctc | 1020 |
| cgcggcacca acttccctcc tgacggcccc gtaatgcaga agaagacaat gggctgggaa | 1080 |
| gcgtccaccg agcggttgta ccccgaggac ggcgtgctga agggcgacat taagatggcc | 1140 |
| ctgcgcctga aggacggcgg ccgctacctg gcggacttca agaccaccta caaggccaag | 1200 |
| aagcccgtgc agatgcccgg cgcctacaac gtcgaccgca agttggacat cacctcccac | 1260 |
| aacgaggact acaccgtggt ggaacagtac gaacgctccg agggccgcca ctccaccggc | 1320 |
| ggcatggacg agctgtacaa gtagggtacc ctgtgccttc tagttgccag ccatctgttg | 1380 |
| tttgcccctc ccccgtgcct tccttgaccc tggaaggtgc cactcccact gtcctttcct | 1440 |
| aataaaatga ggaaattgca tcgcattgtc tgagtaggtg tcattctatt ctggggggtg | 1500 |
| gggtggggca ggacagcaag ggggaggatt gggaagacaa tagcaggcat gctggggatg | 1560 |
| cggtgggctc tatgggcgcg ccatcgatgt gaagtgggta acctttattt cccttctttt | 1620 |
| tctctttagc tcggcttatt ccaggggtgt gtttcgtcga gatgcacaca agagtgaggt | 1680 |
| tgctcatcgg tttaaagatt tgggagaaga aaatttcaaa gccttggtgt tgattgcctt | 1740 |
| tgctcagtat cttcagcagt gtccatttga agatcatgta aaattagtga atgaagtaac | 1800 |
| tgaatttgca aaaacatgtg ttgctgatga gtcagctgaa aattgtgaca atcacttca | 1860 |
| tacccttttt ggagacaaat tatgcacagt tgcaactctt cgtgaaacct atggtgaaat | 1920 |
| ggctgactgc tgtgcaaaac aagaacctga gagaatgaa tgcttcttgc aacacaaaga | 1980 |
| tgacaaccca aacctccccc gattggtgag accagaggtt gatgtgatgt gcactgcttt | 2040 |
| tcatgacaat gaagagacct ttttgaaaaa atacttatac gaaattgcca gaagacatcc | 2100 |
| ttactttat gccccggaac tccttttctt tgctaaaagg tataaagctg cttttacaga | 2160 |
| atgttgccaa gctgctgata aagctgcctg cctgttgcca aagctcgatg aacttcggga | 2220 |
| tgaagggaag gcttcgtctg ccaaacagag actcaagtgt gccagtctcc aaaaatttgg | 2280 |
| agaaagagct ttcaaagcat gggcagtagc tcgcctgagc cagagatttc caaagctga | 2340 |
| gtttgcagaa gtttccaagt tagtgacaga tcttaccaaa gtccacacgg aatgctgcca | 2400 |
| tggagatctg cttgaatgtg ctgatgacag ggcggacctt gccaagtata tctgtgaaaa | 2460 |
| tcaagattcg atctccagta aactgaagga atgctgtgaa aaacctctgt tggaaaaaatc | 2520 |

```
ccactgcatt gccgaagtgg aaaatgatga gatgcctgct gacttgcctt cattagctgc    2580
tgattttgtt gaaagtaagg atgtttgcaa aaactatgct gaggcaaagg atgtcttcct    2640
gggcatgttt ttgtatgaat atgcaagaag catcctgat tactctgtcg tgctgctgct     2700
gagacttgcc aagacctatg aaaccactct agagaagtgc tgtgccgctg cagatcctca    2760
tgaatgctat gccaaagtgt tcgatgaatt taaacctctt gtggaagagc ctcagaattt    2820
aatcaaacaa aattgtgagc ttttgagca gcttggagag tacaaattcc agaatgcgct     2880
attagttcgt tacaccaaga aagtacccca agtgtcaact ccaactcttg tagaggtctc    2940
aagaaaccta ggaaagtgg gcagcaaatg ttgtaaacat cctgaagcaa aagaatgcc     3000 ctgtgcagaa gactatctat ccgtggtcct gaaccagtta tgtgtgttgc atgagaaaac    3060
gccagtaagt gacagagtca ccaaatgctg cacagaatcc ttggtgaaca ggcgaccatg    3120
tcgtgaaacc tatggtgaaa tggctgactg ctgtgcaaaa caagaacctg agagaaatga    3180
atgcttcttg caacacaaag atgacaaccc aaacctcccc cgattggtga accagaggt     3240 tgatgtgatg tgcactgctt ttcatgacaa tgaagagacc ttttgaaaa aatacttata    3300 cgaaattgcc agaagacatc cttacttta tgccccggaa ctccttttct ttgctaaaag    3360
gtataaagct gcttttacag aatgttgcca agctgctgat aaagctgcct gcctgttgcc    3420
aaagctcgat gaacttcggg atgaagggaa ggcttcgtct gccaaacaga gactcaagtg    3480
tgccagtctc caaaaatttg gagaaagagc tttcaaagca tgggcagtag ctcgcctgag    3540
ccagactttt cagctctgga agtcgatgaa acatacgttc ccaaagagtt taatgctgaa    3600
acattcacct tccatgcaga tatatgcaca ctttctgaga aggagagaca aatcaagaaa    3660
caaactgcac ttgttgagct cgtgaaacac aagcccaagg caacaaaaga gcaactgaaa    3720
gctgttatgg atgatttcgc tcgagccatg ggcgcgccat cgatgaggaa cccctagtga    3780
tggagttggc cactccctct ctgcgcgctc gctcgctcac tgaggccggg cgaccaaagg    3840
tcgcccgacg cccgggcttt gcccgggcgg cctcagtgag cgagcgagcg cgcagctgcc    3900
tgcagg                                                              3906
```

<210> SEQ ID NO 29  
<211> LENGTH: 4140  
<212> TYPE: DNA  
<213> ORGANISM: Artificial Sequence  
<220> FEATURE:  
<223> OTHER INFORMATION: C-dmScar-shortUTR

<400> SEQUENCE: 29

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc ttgcgtcgac aggcctccta ggcggaccgc ttgcatgcac    180
gcgtagtgca agtgggtttt aggaccagga tgaggcgggg tgggggtgcc tacctgacga    240
ccgaccccga cccactggac aagcacccaa cccccattcc ccaaattgcg catcccctat    300
cagagagggg gaggggaaac aggatgcggc gaggcgcgtg cgcactgcca gcttcagcac    360
cgcggacagt gccttcgccc ccgcctggcg gcgcgcgcca ccgccgcctc agcactgaag    420
gcgcgctgac gtcactcgcc ggtccccgc aaactcccct tcccggccac cttggtcgcg    480
tccgcgccgc cgccggccca gccggaccgc accacgcgag gcgcgagata gggggcacg    540 ggcgcgacca tctgcgctgc ggcgccggcg actcagcgct gcctcagtct gcggtgggca    600
```

```
gcggaggagt cgtgtcgtgc ctgagagcgc agaccggtcg ccaccatggt gagcaagggc    660
gaggcagtga tcaaggagtt catgcggttc aaggtgcaca tggagggctc catgaacggc    720
cacgagttcg agatcgaggg cgagggcgag ggccgcccct acgagggcac ccagaccgcc    780
aagctgaagg tgaccaaggg tggccccctg cccttctcct gggacatcct gtcccctcag    840
ttcatgtacg gctccagggc cttcatcaag caccccgccg acatccccga ctactataag    900
cagtccttcc ccgagggctt caagtgggag gcgcgtgatga acttcgagga cggcggcgcc    960
gtgaccgtga cccaggacac ctccctggag gacggcaccc tgatctacaa ggtgaagctc    1020
cgcggcacca acttccctcc tgacggcccc gtaatgcaga agaagacaat gggctgggaa    1080
gcgtccaccg agcggttgta ccccgaggac ggcgtgctga agggcgacat taagatggcc    1140
ctgcgcctga aggacggcgg ccgctacctg gcggacttca agaccaccta caaggccaag    1200
aagcccgtgc agatgcccgg cgcctacaac gtcgaccgca gttggacat cacctcccac    1260 aacgaggact acaccgtggt ggaacagtac aacgctccg agggccgcca ctccaccggc    1320
ggcatggacg agctgtacaa gaagcttccg cggagccatg gcttcccgcc ggcggtggcg    1380
gcgcaggatg atggcacgct gcccatgtct tgtgcccagg agagcgggat ggaccgtcac    1440
cctgcagcct gtgcttctgc taggatcaat gtgtagggta cctggattta tgttgtatag    1500
attagattat attgagacaa aaattatcta tttgtatata tacataacag ggtaaattat    1560
tcagttaaga aaaaataat tttatgaact gcatgtataa atgaagttta tacagtacag    1620
tggttctaca atctattttat tggacatgtc catgaccaga agggaaacag tcatttgcgc    1680
acaacttaaa aagtctgcat tacattcctt gataatgttg tggtttgttg ccgttgccaa    1740
gaactgaaaa cataaaaagt taaaaaaaat aataaattgc atgctgcttt aattgtgaat    1800
tgataataag cgcgccatcg atgtgaagtg ggtaaccttt atttccttc ttttctctt    1860 tagctcggct tattccaggg gtgtgtttcg tcgagatgca cacaagagtg aggttgctca    1920
tcggtttaaa gatttgggag aagaaaattt caaagccttg gtgttgattg cctttgctca    1980
gtatcttcag cagtgtccat ttgaagatca tgtaaaatta gtgaatgaag taactgaatt    2040
tgcaaaaaca tgtgttgctg atgagtcagc tgaaaattgt gacaaatcac ttcatacct    2100 ttttggagac aaattatgca cagttgcaac tcttcgtgaa acctatggtg aaatggctga    2160
ctgctgtgca aaacaagaac ctgagagaaa tgaatgcttc ttgcaacaca agatgacaa    2220 cccaaacctc ccccgattgg tgagaccaga ggttgatgtg atgtgcactg cttttcatga    2280
caatgaagag acctttttga aaaatactt atacgaaatt gccagaagac atccttactt    2340
ttatgccccg gaactccttt tctttgctaa aaggtataaa gctgcttta cagaatgttg    2400 ccaagctgct gataaagctg cctgcctgtt gccaaagctc gatgaacttc gggatgaagg    2460
gaaggcttcg tctgccaaac agagactcaa gtgtgccagt ctccaaaaat ttggagaaag    2520
agctttcaaa gcatgggcag tagctcgcct gagccagaga tttcccaaag ctgagtttgc    2580
agaagtttcc aagttagtga cagatcttac caaagtccac acggaatgct gccatggaga    2640
tctgcttgaa tgtgctgatg acagggcgga ccttgccaag tatatctgtg aaaatcaaga    2700
ttcgatctcc agtaaactga aggaatgctg tgaaaaacct ctgttggaaa atcccactg    2760 cattgccgaa gtggaaaatg atgagatgcc tgctgacttg ccttcattag ctgctgattt    2820
tgttgaaagt aaggatgttt gcaaaaacta tgctgaggca aaggatgtct tcctgggcat    2880 gttttttgtat gaatatgcaa gaaggcatcc tgattactct gtcgtgctgc tgctgagact    2940
tgccaagacc tatgaaacca ctctagagaa gtgctgtgcc gctgcagatc ctcatgaatg    3000
```

```
ctatgccaaa gtgttcgatg aatttaaacc tcttgtggaa gagcctcaga atttaatcaa     3060
acaaaattgt gagcttttg agcagcttgg agagtacaaa ttccagaatg cgctattagt      3120
tcgttacacc aagaaagtac cccaagtgtc aactccaact cttgtagagg tctcaagaaa     3180
cctaggaaaa gtgggcagca aatgttgtaa acatcctgaa gcaaaaagaa tgccctgtgc     3240
agaagactat ctatccgtgg tcctgaacca gttatgtgtg ttgcatgaga aaacgccagt     3300
aagtgacaga gtcaccaaat gctgcacaga atccttggtg aacaggcgac catgtcgtga     3360
aacctatggt gaaatggctg actgctgtgc aaaacaagaa cctgagagaa atgaatgctt     3420
cttgcaacac aaagatgaca acccaaacct cccccgattg gtgagaccag aggttgatgt     3480
gatgtgcact gcttttcatg acaatgaaga accttttttg aaaaaatact tatacgaaat     3540
tgccagaaga catccttact tttatgcccc ggaactcctt ttctttgcta aaaggtataa     3600
agctgctttt acagaatgtt gccaagctgc tgataaagct gcctgcctgt tgccaaagct     3660
cgatgaactt cgggatgaag ggaaggcttc gtctgccaaa cagagactca agtgtgccag     3720
tctccaaaaa tttggagaaa gagctttcaa agcatgggca gtagctcgcc tgagccagac     3780
ttttcagctc tggaagtcga tgaaacatac gttcccaaag agtttaatgc tgaaacattc     3840
accttccatg cagatatatg cacactttct gagaaggaga gacaaatcaa gaaacaaact     3900
gcacttgttg agctcgtgaa acacaagccc aaggcaacaa aagagcaact gaaagctgtt     3960
atggatgatt tcgctcgagc catgggcgcg ccatcgatga ggaaccccta gtgatggagt     4020
tggccactcc ctctctgcgc gctcgctcgc tcactgaggc cgggcgacca aaggtcgccc     4080
gacgcccggg ctttgcccgg gcggcctcag tgagcgagcg agcgcgcagc tgcctgcagg     4140
```

<210> SEQ ID NO 30
<211> LENGTH: 4575
<212> TYPE: DNA
<213> ORGANISM: Artificial Sequence
<220> FEATURE:
<223> OTHER INFORMATION: C-dmScar-longUTR

<400> SEQUENCE: 30

```
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac tagggttcc ttgcgtcgac aggcctccta gcggaccgc ttgcatgcac        180 gcgtagtgca agtgggtttt aggaccagga tgaggcgggg tgggggtgcc tacctgacga     240
ccgaccccga cccactggac aagcacccaa cccccattcc ccaaattgcg catcccctat     300
cagagagggg gaggggaaac aggatgcggc gaggcgcgtg cgcactgcca gcttcagcac     360
cgcggacagt gccttcgccc ccgcctggcg gcgcgcgcca ccgccgcctc agcactgaag     420
gcgcgctgac gtcactcgcc ggtccccgc aaactcccct tcccggccac cttggtcgcg     480
tccgcgccgc cgccggccca gccggaccgc accacgcgag gcgcgagata ggggggcacg    540
ggcgcgacca tctgcgctgc ggcgccggcg actcagcgct gcctcagtct gcggtgggca     600
gcggaggagt cgtgtcgtgc ctgagagcgc agaccggtcg ccaccatggt gagcaagggc     660
gaggcagtga tcaaggagtt catgcggttc aaggtgcaca tggagggctc catgaacggc     720
cacgagttcg agatcgaggg cgagggcgag ggccgcccct acgagggcac ccagaccgcc     780
aagctgaagg tgaccaaggg tggccccctg cccttctcct gggacatcct gtcccctcag     840
ttcatgtacg gctccagggc cttcatcaag caccccgccg acatcccga ctactataag      900
```

```
cagtccttcc ccgagggctt caagtgggag cgcgtgatga acttcgagga cggcggcgcc    960
gtgaccgtga cccaggacac ctccctggag acggcaccc  tgatctacaa ggtgaagctc   1020
cgcggcacca acttccctcc tgacggcccc gtaatgcaga agaagacaat gggctgggaa   1080
gcgtccaccg agcggttgta ccccgaggac ggcgtgctga agggcgacat taagatggcc   1140
ctgcgcctga aggacggcgg ccgctacctg gcggacttca agaccaccta caaggccaag   1200
aagcccgtgc agatgcccgg cgcctacaac gtcgaccgca agttggacat cacctcccac   1260
aacgaggact acaccgtggt ggaacagtac gaacgctccg agggccgcca ctccaccggc   1320
ggcatggacg agctgtacaa gaagcttccg cggagccatg gcttccccgcc ggcggtggcg   1380
gcgcaggatg atggcacgct gcccatgtct tgtgcccagg agagcgggat ggaccgtcac   1440
cctgcagcct gtgcttctgc taggatcaat gtgtagggta cctggattta tgttgtatag   1500
attagattat attgagacaa aaattatcta tttgtatata tacataacag ggtaaattat   1560
tcagttaaga aaaaaataat tttatgaact gcatgtataa atgaagttta tacagtacag   1620
tggttctaca atctatttat tggacatgtc catgaccaga agggaaacag tcatttgcgc   1680
acaacttaaa aagtctgcat tacattcctt gataatgttg tggtttgttg ccgttgccaa   1740
gaactgaaaa cataaaaagt taaaaaaaat aataaattgc atgctgcttt aattgtgaat   1800
tgataataaa ctgtcctctt tcagaaaaca gaaaaaaaca cacacacaca caacaaaaat   1860
ttgaaccaaa acattccgtt tacattttag acagtaagta tcttcgttct tgttagtact   1920
atatctgttt tactgctttt aacttctgat agcgttggaa ttaaaacaat gtcaaggtgc   1980
tgttgtcatt gctttactgg cttaggggat gggggatggg gggtatattt ttgtttgttt   2040
tgtgtttttt tttcgtttgt ttgttttgtt tttagttcc  cacagggagt agagatgggg   2100
aaagaattcc tacaatatat attctggctg ataaaagata catttgtatg ttgtgaagat   2160
gtttgcaata tcgatcagat gactagaaag tgaataaaaa ttaaggcaac tgaacaaaaa   2220
aatgctcaca ctccacatcc cgtgatgcac ctcccaggcc ccgctcattc tttgggcgtt   2280
ggtcagagta agctgctttt gacggaagga cctatgtttg ctcagaacac attctttccc   2340
cccctccccc tctggtctcc tctttgtttt gttttaagga agaaaaatca gttgcgcgtt   2400
ctgaaatatt ttaccactgc tgtgaacaag tgaacacatt gtgtcacatc atgacactcg   2460
tataagcatg gagaacagtg atttttttt  agaacagaaa acaacaaaaa ataaccccaa   2520
aatgaagatt atttttttatg aggagtgaac atttgggtaa atcatggcta agcttaaaaa   2580
aaactcatgg tgaggcttaa caatgtcttg taagcaaaag gtagagccct gtatcaaccc   2640
agaaacacct agatcagaac aggaatccac attgccagtg acatgagact gaacagccaa   2700
atggaggcta tgtggagttg gcattgcatt taccggcagt gcgggaggaa tttctgagtg   2760
gccatcccaa ggtctaggtg gaggtggggc atggtatttg agacattcca aaacgaaggc   2820
ctctgaagga cccttcagag gtggctctgg aatgacatgt gtcaagctgc ttggacctcg   2880
tgctttaagt gcctacatta tctaactgtg ctcaagaggt tctcgactgg aggaccacac   2940
tcaagccgac ttatgcccac catcccacct ctggataatt ttgcataaaa ttggattagc   3000
ctggagcagg ttgggagcca aatgtggcat ttgtgatcat gagattgatg caatgagata   3060
gaagatgttt gctacctgaa cacttattgc tttgaaacta gacttgagga aaccagggtt   3120
tatcttttga gaacttttgg taagggaaaa gggaacagga aagaaaccc  caaactcagg   3180
ccgaatgatc aaggggaccc ataggaaatc ttgtccagac acaagacttc gggaaggtgt   3240
ctggacattc agaacaccaa gacttgaagg tgccttgctc aatggaagag gccaggacag   3300
```

```
agctgacaaa attttgctcc ccagtgaagg ccacagcaac cttctgccca tcctgtctgt    3360
tcatggagag ggtccctgcc tcacctctgc cattttgggt taggagaagt caagttggga    3420
gcctgaaata gtggttcttg gaaaaatgga tccccagtga aaactagagc tctaagccca    3480
ttcagcccat ttcacacctg aaaatgttag tgatcaccac ttggaccagc atccttaagt    3540
atcagaaagc cccaagcaat tgctgcatct tagtagggtg agggataagc aaaagaggat    3600
gttcaccata acccaggaat gaagatacca tcagcaaaga atttcaattt gttcagtctt    3660
tcatttagag ctagtctttc acagtaccat ctgaatacct ctttgaaaga aggaagactt    3720
tacgtagtgt agatttgttt tgtgttgttt gaaaatatta tctttgtaat tatttttaat    3780
atgtaaggaa tgcttggaat atctgctata tgtcaacttt atgcagcttc cttttgaggg    3840
acaaatttaa aacaaacaac cccccatcac aaacttaaag gattgcaagg gccagatctg    3900
ttaagtggtt tcataggaga cacatccagc aattgtgtgg tcagtggctc ttttacccaa    3960
taagatacat cacagtcaca tgcttgatgg tttatgttga cctaagattt attttgttaa    4020
aatctctctc tgttgtgttc gttcttgttc tgttttgttt tgttttttaa agtcttgctg    4080
tggtctcttt gtggcagaag tgtttcatgc atggcagcag gctgttgct tttttatggc    4140
gattcccatt gaaaatgtaa gtaaatgtct gtggccttgt tctctctatg gtaaagatat    4200
tattcaccat gtaaaacaaa aacaatatt tattgtattt tagtatattt atataattat    4260
gttattgaaa aaaattggca ttaaaactta accgcatcag aacctattgt aaatacaagt    4320
tctatttaag tgtactaatt aacatataat atatgtttta aatatagaat ttttaatgtt    4380
tttaaatata ttttcaaagt acataaaact cgagccatgg gcgcgccatc gatgaggaac    4440
ccctagtgat ggagttggcc actccctctc tgcgcgctcg ctcgctcact gaggccgggc    4500
gaccaaaggt cgcccgacgc ccgggctttg cccgggcggc ctcagtgagc gagcgagcgc    4560
gcagctgcct gcagg                                                    4575
```

<210> SEQ ID NO 31
<211> LENGTH: 4038
<212> TYPE: DNA
<213> ORGANISM: Artificial Sequence
<220> FEATURE:
<223> OTHER INFORMATION: C-dmScar-bGH

<400> SEQUENCE: 31

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggttcc ttgcgtcgac aggcctccta ggcggaccgc ttgcatgcac    180
gcgtagtgca agtgggtttt aggaccagga tgaggcgggg tggggtgcc tacctgacga    240
ccgaccccga cccactggac aagcacccaa cccccattcc ccaaattgcg catcccctat    300
cagagagggg gaggggaaac aggatgcggc gaggcgcgtg cgcactgcca gcttcagcac    360
cgcggacagt gccttcgccc ccgcctggcg gcgcgcgcca ccgccgcctc agcactgaag    420
gcgcgctgac gtcactcgcc ggtccccgc aaactcccct tcccggccac cttggtcgcg    480
tccgcgccgc cgcggcccca gccggaccgc accacgcgag gcgcgagata gggggcacg    540
ggcgcgacca tctgcgctgc ggcgccggcg actcagcgct gcctcagtct gcggtgggca    600
gcggaggagt cgtgtcgtgc ctgagagcgc agaccggtcg ccaccatggt gagcaagggc    660
gaggcagtga tcaaggagtt catgcggttc aaggtgcaca tggagggctc catgaacggc    720
```

```
cacgagttcg agatcgaggg cgagggcgag ggccgcccct acgagggcac ccagaccgcc    780
aagctgaagg tgaccaaggg tggcccctg cccttctcct gggacatcct gtcccctcag    840
ttcatgtacg gctccagggc cttcatcaag caccccgccg acatcccga ctactataag    900
cagtccttcc ccgagggctt caagtgggag cgcgtgatga acttcgagga cggcggcgcc    960
gtgaccgtga cccaggacac ctccctggag gacggcaccc tgatctacaa ggtgaagctc   1020
cgcggcacca acttccctcc tgacggcccc gtaatgcaga agaagacaat gggctgggaa   1080
gcgtccaccg agcggttgta cccggaggac ggcgtgctga agggcgacat taagatggcc   1140
ctgcgcctga aggacggcgg ccgctacctg gcggacttca gaccaccta caaggccaag   1200
aagcccgtgc agatgcccgg cgcctacaac gtcgaccgca gttggacat cacctcccac   1260
aacgaggact acaccgtggt ggaacagtac gaacgctccg agggccgcca ctccaccggc   1320
ggcatggacg agctgtacaa gaagcttccg cggagccatg gcttcccgcc ggcggtggcg   1380
gcgcaggatg atggcacgct gcccatgtct tgtgcccagg agagcgggat ggaccgtcac   1440
cctgcagcct gtgcttctgc taggatcaat gtgtagggta ccctgtgcct tctagttgcc   1500
agccatctgt tgtttgcccc tcccccgtgc cttccttgac cctggaaggt gccactccca   1560
ctgtcctttc ctaataaaat gaggaaattg catcgcattg tctgagtagg tgtcattcta   1620
ttctgggggg tggggtgggg caggacagca aggggagga ttgggaagac aatagcaggc   1680
atgctgggga tgcggtgggc tctatgggcg cgccatcgat gtgaagtggg taaccttttat  1740
ttcccttctt tttctcttta gctcggctta ttccaggggt gtgtttcgtc gagatgcaca   1800
caagagtgag gttgctcatc ggtttaaaga tttgggagaa gaaaatttca aagccttggt   1860
gttgattgcc tttgctcagt atcttcagca gtgtccattt gaagatcatg taaaattagt   1920
gaatgaagta actgaatttg caaaaacatg tgttgctgat gagtcagctg aaaattgtga   1980
caaatcactt catacccttt ttggagacaa attatgcaca gttgcaactc ttcgtgaaac   2040
ctatggtgaa atgctgact gctgtgcaaa acaagaacct gagagaaatg aatgcttctt   2100
gcaacacaaa gatgacaacc caaacctccc ccgattggtg agaccagagg ttgatgtgat   2160
gtgcactgct tttcatgaca atgaagagac ctttttgaaa aaatacttat acgaaattgc   2220
cagaagacat ccttactttt atgccccgga actccttttc tttgctaaaa ggtataaagc   2280
tgcttttaca gaatgttgcc aagctgctga taaagctgcc tgcctgttgc caaagctcga   2340
tgaacttcgg gatgaaggga aggcttcgtc tgccaaacag agactcaagt gtgccagtct   2400
ccaaaaattt ggagaaagag ctttcaaagc atgggcagta gctcgcctga gccagagatt   2460
tcccaaagct gagtttgcag aagtttccaa gttagtgaca gatcttacca agtccacac   2520
ggaatgctgc catggagatc tgcttgaatg tgctgatgac agggcggacc ttgccaagta   2580
tatctgtgaa aatcaagatt cgatctccag taaactgaag gaatgctgtg aaaaacctct   2640
gttggaaaaa tcccactgca ttgccgaagt ggaaaatgat gagatgcctg ctgacttgcc   2700
ttcattagct gctgattttg ttgaaagtaa ggatgtttgc aaaaactatg ctgaggcaaa   2760
ggatgtcttc ctgggcatgt ttttgtatga atatgcaaga aggcatcctg attactctgt   2820
cgtgctgctg ctgagacttg ccaagaccta tgaaaccact ctagaagt gctgtgccgc   2880
tgcagatcct catgaatgct atgccaaagt gttcgatgaa tttaaacctc ttgtggaaga   2940
gcctcagaat ttaatcaaac aaaattgtga gcttttgag cagcttggag agtacaaatt   3000
ccagaatgcg ctattagttc gttacaccaa gaaagtaccc caagtgtcaa ctccaactct   3060
tgtagaggtc tcaagaaacc taggaaaagt gggcagcaaa tgttgtaaac atcctgaagc   3120
```

```
aaaaagaatg ccctgtgcag aagactatct atccgtggtc ctgaaccagt tatgtgtgtt   3180
gcatgagaaa acgccagtaa gtgacagagt caccaaatgc tgcacagaat ccttggtgaa   3240
caggcgacca tgtcgtgaaa cctatggtga atggctgac tgctgtgcaa aacaagaacc   3300
tgagagaaat gaatgcttct tgcaacacaa agatgacaac ccaaacctcc cccgattggt   3360
gagaccagag gttgatgtga tgtgcactgc ttttcatgac aatgaagaga ccttttgaa    3420 aaaatactta tacgaaattg ccagaagaca tccttacttt tatgccccgg aactcctttt   3480
ctttgctaaa aggtataaag ctgcttttac agaatgttgc caagctgctg ataaagctgc   3540
ctgcctgttg ccaaagctcg atgaacttcg ggatgaaggg aaggcttcgt ctgccaaaca   3600
gagactcaag tgtgccagtc tccaaaaatt tggagaaaga gctttcaaag catgggcagt   3660
agctcgcctg agccagactt ttcagctctg gaagtcgatg aaacatacgt tcccaaagag   3720
tttaatgctg aaacattcac cttccatgca gatatatgca cactttctga aaggagaga   3780 caaatcaaga aacaaactgc acttgttgag ctcgtgaaac acaagcccaa ggcaacaaaa   3840
gagcaactga aagctgttat ggatgatttc gctcgagcca tgggcgcgcc atcgatgagg   3900 aaccccctagt gatggagttg gccactccct ctctgcgcgc tcgctcgctc actgaggccg   3960
ggcgaccaaa ggtcgcccga cgcccgggct ttgcccgggc ggcctcagtg agcgagcgag   4020
cgcgcagctg cctgcagg                                                4038

<210> SEQ ID NO 32
<211> LENGTH: 4287
<212> TYPE: DNA
<213> ORGANISM: Artificial Sequence
<220> FEATURE:
<223> OTHER INFORMATION: AD-dmScar-shortUTR

<400> SEQUENCE: 32
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc ttgcgtcgac aggcctccta ggcggaccgc ttgcatgcac   180
gcgtgggtgg tgcagagtct gcatgcgtga ggagctcctg ggcgcgtcac agccgcgcta   240
ttctcagcgt ctctcctttt atggctccgg aagtgagctg gggttgctgg cagccgtccc   300
tcggtccccg caggctgaat gagccccgcc gtccggggtg ggaggtacgg agcggaggga   360
ttagtcatcc tggccccgcc atgtgtgcag ggggtgggac ctcccgtccc ttgccgcccg   420
ggagccgagt gggcgcaggg cggggcctgc aggggcgcgg gcggggcgct ggcggggagc   480
ctgcggctgg gccaatgaga aaccgggctc ggcgagccgg ccgcccacgg gcctcgctgg   540
ctgcataaag agccggcggc caggactcag cgcagagctc gggcgcggcg tcctccctcc   600
gcagcagccg agccggacct gcctccccgg gcgtgctccg ccggccccgc cgccggcccg   660
cagcgacaga caggcgctcc ccgcagctcc gcacggacc caggccgccg gaccccagcg    720
ccggaccacc ctctgtccgc cccgaggagt ttgccgcctg ccggagcacc tgcgcacaga   780
ccggtcgcca ccatggtgag caagggcgag gcagtgatca aggagttcat gcggttcaag   840
gtgcacatgg agggctccat gaacggccac gagttcgaga tcgagggcga gggcgagggc   900
cgcccctacg agggcaccca gaccgccaag ctgaaggtga ccaagggtgg cccctgccc    960 ttctcctggg acatcctgtc ccctcagttc atgtacggct ccaggccctt catcaagcac   1020
cccgccgaca tccccgacta ctataagcag tccttccccg agggcttcaa gtgggagcgc   1080
```

```
gtgatgaact tcgaggacgg cggcgccgtg accgtgaccc aggacacctc cctggaggac      1140
ggcaccctga tctacaaggt gaagctccgc ggcaccaact tccctcctga cggccccgta      1200
atgcagaaga agacaatggg ctgggaagcg tccaccgagc ggttgtaccc cgaggacggc      1260
gtgctgaagg gcgacattaa gatggccctg cgcctgaagg acggcggccg ctacctggcg      1320
gacttcaaga ccacctacaa ggccaagaag cccgtgcaga tgcccggcgc ctacaacgtc      1380
gaccgcaagt tggacatcac ctcccacaac gaggactaca ccgtggtgga acagtacgaa      1440
cgctccgagg gccgccactc caccggcggc atggacgagc tgtacaagaa gcttccgcgg      1500
agccatggct cccgccggc ggtggcgcg caggatgatg gcacgctgcc catgtcttgt       1560
gcccaggaga gcgggatgga ccgtcaccct gcagcctgtg cttctgctag gatcaatgtg      1620
tagggtacct ggatttatgt tgtatagatt agattatatt gagacaaaaa ttatctattt      1680
gtatatatac ataacagggt aaattattca gttaagaaaa aataattttt atgaactgca      1740
tgtataaatg aagtttatac agtacagtgg ttctacaatc tatttattgg acatgtccat      1800
gaccagaagg gaaacagtca tttgcgcaca acttaaaaag tctgcattac attccttgat      1860
aatgttgtgg tttgttgccg ttgccaagaa ctgaaaacat aaaaagttaa aaaaaataat      1920
aaattgcatg ctgctttaat tgtgaattga taataagcgc gccatcgatg tgaagtgggt      1980
aacctttatt tcccttcttt ttctctttag ctcggcttat tccaggggtg tgtttcgtcg      2040
agatgcacac aagagtgagg ttgctcatcg gtttaaagat ttgggagaag aaaatttcaa      2100
agccttggtg ttgattgcct ttgctcagta tcttcagcag tgtccatttg aagatcatgt      2160
aaaattagtg aatgaagtaa ctgaatttgc aaaaacatgt gttgctgatg agtcagctga      2220
aaattgtgac aaatcacttc ataccctttt tggagacaaa ttatgcacag ttgcaactct      2280
tcgtgaaacc tatggtgaaa tggctgactg ctgtgcaaaa caagaacctg agagaaatga      2340
atgcttcttg caacacaaag atgacaaccc aaacctcccc cgattggtga gaccagaggt      2400
tgatgtgatg tgcactgctt ttcatgacaa tgaagagacc ttttgaaaa atacttata       2460 cgaaattgcc agaagacatc cttactttta tgccccggaa ctccttttct tgctaaaag       2520 gtataaagct gcttttacag aatgttgcca agctgctgat aaagctgcct gcctgttgcc      2580
aaagctcgat gaacttcggg atgaagggaa ggcttcgtct gccaaacaga gactcaagtg      2640
tgccagtctc caaaaatttg gagaaagagc tttcaaagca tgggcagtag ctcgcctgag      2700
ccagagattt cccaaagctg agtttgcaga agtttccaag ttagtgacag atcttaccaa      2760
agtccacacg gaatgctgcc atggagatct gcttgaatgt gctgatgaca gggcggacct      2820
tgccaagtat atctgtgaaa atcaagattc gatctccagt aaactgaagg aatgctgtga      2880
aaaacctctg ttggaaaaat cccactgcat tgccgaagtg aaaatgatg agatgcctgc       2940 tgacttgcct tcattagctg ctgattttgt tgaaagtaag gatgtttgca aaaactatgc      3000
tgaggcaaag gatgtcttcc tgggcatgtt tttgtatgaa tatgcaagaa ggcatcctga      3060
ttactctgtc gtgctgctgc tgagacttgc caagacctat gaaaccactc tagagaagtg      3120
ctgtgccgct gcagatcctc atgaatgcta tgccaaagtg ttcgatgaat ttaaacctct      3180
tgtggaagag cctcagaatt taatcaaaca aaattgtgag cttttgagc agcttggaga       3240 gtacaaattc cagaatgcgc tattagttcg ttacaccaag aaagtacccc aagtgtcaac      3300
tccaactctt gtagaggtct caagaaacct aggaaagtg gcagcaaat gttgtaaaca        3360 tcctgaagca aaaagaatgc cctgtgcaga agactatcta tccgtggtcc tgaaccagtt      3420
atgtgtgttg catgagaaaa cgccagtaag tgacagagtc accaaatgct gcacagaatc      3480
```

```
cttggtgaac aggcgaccat gtcgtgaaac ctatggtgaa atggctgact gctgtgcaaa    3540
acaagaacct gagagaaatg aatgcttctt gcaacacaaa gatgacaacc caaacctccc    3600
ccgattggtg agaccagagg ttgatgtgat gtgcactgct tttcatgaca atgaagagac    3660 cttttttgaaa aaatacttat acgaaattgc cagaagacat ccttactttt atgcccggga    3720
actccttttc tttgctaaaa ggtataaagc tgcttttaca gaatgttgcc aagctgctga    3780
taaagctgcc tgcctgttgc caaagctcga tgaacttcgg gatgaaggga aggcttcgtc    3840
tgccaaacag agactcaagt gtgccagtct ccaaaaattt ggagaaagag ctttcaaagc    3900
atgggcagta gctcgcctga ccagactttt tcagctctgg aagtcgatga acatacgtt     3960 cccaaagagt ttaatgctga acattcacc ttccatgcag atatatgcac actttctgag     4020
aaggagagac aaatcaagaa acaaactgca cttgttgagc tcgtgaaaca caagcccaag    4080
gcaacaaaag agcaactgaa agctgttatg gatgatttcg ctcgagccat gggcgcgcca    4140
tcgatgagga cccctagtg atggagttgg ccactccctc tctgcgcgct cgctcgctca    4200
ctgaggccgg gcgaccaaag gtcgcccgac gcccgggctt gcccgggcg gcctcagtga    4260 gcgagcgagc gcgcagctgc ctgcagg                                        4287

<210> SEQ ID NO 33
<211> LENGTH: 4722
<212> TYPE: DNA
<213> ORGANISM: Artificial Sequence
<220> FEATURE:
<223> OTHER INFORMATION: AD-dmScar-longUTR

<400> SEQUENCE: 33
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc ttgcgtcgac aggcctccta gcggaccgc ttgcatgcac      180 gcgtgggtgg tgcagagtct gcatgcgtga ggagctcctg ggcgcgtcac agccgcgcta     240
ttctcagcgt ctctccttttt atggctccgg aagtgagctg gggttgctgg cagccgtccc    300
tcggtccccg caggctgaat gagccccgcc gtccggggtg ggaggtacgg agcggaggga     360
ttagtcatcc tggccccgcc atgtgtgcag ggggtgggac ctcccgtccc ttgccgcccg     420
ggagccgagt gggcgcaggg cggggcctgc aggggcgcgg gcggggcgct ggcggggagc     480
ctgcggctgg gccaatgaga accgggctc ggcgagccgg ccgcccacgg gcctcgctgg      540
ctgcataaag agccggcggc caggactcag cgcagagctc gggcgcggcg tcctccctcc     600
gcagcagccg agccggacct gcctccccgg gcgtgctccg ccggcccgc cgccggcccg      660 cagcgacaga caggcgctcc ccgcagctcc gcacgggacc caggccgccg accccagcg      720 ccggaccacc ctctgtccgc cccgaggagt ttgccgcctg ccggagcacc tgcgcacaga     780
ccggtcgcca ccatggtgag caagggcgag gcagtgatca aggagttcat gcggttcaag     840
gtgcacatgg agggctccat gaacggccac gagttcgaga tcgagggcga gggcgagggc     900
cgcccctacg agggcaccca gaccgccaag ctgaaggtga ccaagggtgg ccccctgccc     960
ttctcctggg acatcctgtc ccctcagttc atgtacggct ccaggccctt catcaagcac    1020 ccgccgaca tccccgacta ctataagcag tccttccccg agggcttcaa gtgggagcgc     1080
gtgatgaact tcgaggacgg cggcgccgtg accgtgaccc aggacacctc cctgcaggac    1140 ggcacccctga tctacaaggt gaagctccgc ggcaccaact tccctcctga cggccccgta    1200
```

```
atgcagaaga agacaatggg ctgggaagcg tccaccgagc ggttgtaccc cgaggacggc      1260
gtgctgaagg gcgacattaa gatggccctg cgcctgaagg acggcggccg ctacctggcg      1320
gacttcaaga ccacctacaa ggccaagaag cccgtgcaga tgcccggcgc ctacaacgtc      1380
gaccgcaagt tggacatcac ctcccacaac gaggactaca ccgtggtgga acagtacgaa      1440
cgctccgagg gccgccactc caccggcggc atggacgagc tgtacaagaa gcttccgcgg      1500
agccatggct cccgccggc ggtggcggcg caggatgatg gcacgctgcc catgtcttgt       1560
gcccaggaga gcgggatgga ccgtcaccct gcagcctgtg cttctgctag atcaatgtg       1620 tagggtacct ggatttatgt tgtatagatt agattatatt gagacaaaaa ttatctattt      1680
gtatatatac ataacagggt aaattattca gttaagaaaa aataattttt atgaactgca      1740
tgtataaatg aagtttatac agtacagtgg ttctacaatc tatttattgg acatgtccat      1800
gaccagaagg gaaacagtca tttgcgcaca acttaaaaag tctgcattac attccttgat      1860
aatgttgtgg tttgttgccg ttgccaagaa ctgaaaacat aaaaagttaa aaaaaataat      1920
aaattgcatg ctgctttaat tgtgaattga taataaactg tcctctttca gaaaacagaa      1980
aaaaacacac acacacacaa caaaaatttg aaccaaaaca ttccgtttac attttagaca      2040
gtaagtatct tcgttcttgt tagtactata tctgttttac tgcttttaac ttctgatagc      2100
gttggaatta aaacaatgtc aaggtgctgt tgtcattgct ttactggctt aggggatggg      2160
ggatgggggg tatattttttg tttgttttgt gttttttttt cgtttgtttg ttttgttttt      2220
tagttcccac agggagtaga gatggggaaa gaattcctac aatatatatt ctggctgata      2280
aaagatacat ttgtatgttg tgaagatgtt tgcaatatcg atcagatgac tagaaagtga      2340
ataaaaatta aggcaactga acaaaaaaat gctcacactc cacatcccgt gatgcacctc      2400
ccaggccccg ctcattcttt gggcgttggt cagagtaagc tgcttttgac ggaaggacct      2460
atgtttgctc agaacacatt ctttccccc ctcccctct ggtctcctct ttgttttgtt        2520
ttaaggaaga aaaatcagtt gcgcgttctg aaatatttta ccactgctgt gaacaagtga      2580
acacattgtg tcacatcatg acactcgtat aagcatggag aacagtgatt ttttttaga      2640 acagaaaaca acaaaaaata accccaaaat gaagattatt ttttatgagg agtgaacatt      2700
tgggtaaatc atggctaagc ttaaaaaaaa ctcatggtga ggcttaacaa tgtcttgtaa      2760
gcaaaaggta gagccctgta tcaacccaga acaccctaga tcagaacagg aatccacatt      2820
gccagtgaca tgagactgaa cagccaaatg gaggctatgt ggagttggca ttgcatttac      2880
cggcagtgcg ggaggaattt ctgagtggcc atcccaaggt ctaggtggag gtggggcatg      2940
gtatttgaga cattccaaaa cgaaggcctc tgaaggaccc ttcagaggtg gctctggaat      3000
gacatgtgtc aagctgcttg gacctcgtgc tttaagtgcc tacattatct aactgtgctc      3060
aagaggttct cgactggagg accacactca agccgactta tgcccaccat cccacctctg      3120
gataattttg cataaaattg gattagcctg gagcaggttg ggagccaaat gtggcatttg      3180
tgatcatgag attgatgcaa tgagatagaa gatgtttgct acctgaacac ttattgcttt      3240
gaaactagac ttgaggaaac cagggtttat cttttgagaa cttttggtaa gggaaaaggg      3300
aacaggaaaa gaaccccaa actcaggccg aatgatcaag ggacccata ggaaatcttg        3360 tccagagaca agacttcggg aaggtgtctg gacattcaga acaccaagac ttgaaggtgc      3420
cttgctcaat ggaagaggcc aggacagagc tgacaaaatt ttgctcccca gtgaaggcca      3480
cagcaacctt ctgcccatcc tgtctgttca tggagagggt ccctgcctca cctctgccat      3540
tttgggttag gagaagtcaa gttgggagcc tgaaatagtg gttcttggaa aaatggatcc      3600
```

```
ccagtgaaaa ctagagctct aagcccattc agcccatttc acacctgaaa atgttagtga   3660
tcaccacttg gaccagcatc cttaagtatc agaaagcccc aagcaattgc tgcatcttag   3720
tagggtgagg gataagcaaa agaggatgtt caccataacc caggaatgaa gataccatca   3780
gcaaagaatt tcaatttgtt cagtctttca tttagagcta gtctttcaca gtaccatctg   3840
aatacctctt tgaaagaagg aagactttac gtagtgtaga tttgttttgt gttgtttgaa   3900
aatattatct ttgtaattat ttttaatatg taaggaatgc ttggaatatc tgctatatgt   3960
caactttatg cagcttcctt ttgagggaca aatttaaaac aaacaacccc ccatcacaaa   4020
cttaaaggat tgcaagggcc agatctgtta agtggtttca taggagacac atccagcaat   4080
tgtgtggtca gtggctcttt tacccaataa gatacatcac agtcacatgc ttgatggttt   4140
atgttgacct aagatttatt ttgttaaaat ctctctctgt tgtgttcgtt cttgttctgt   4200
tttgttttgt tttttaaagt cttgctgtgg tctctttgtg gcagaagtgt ttcatgcatg   4260
gcagcaggcc tgttgctttt ttatggcgat tcccattgaa aatgtaagta aatgtctgtg   4320
gccttgttct ctctatggta aagatattat tcaccatgta aaacaaaaaa caatatttat   4380 tgtatttttag tatatttata taattatgtt attgaaaaaa attggcatta aaacttaacc   4440
gcatcagaac ctattgtaaa tacaagttct atttaagtgt actaattaac atataatata   4500
tgttttaaat atagaatttt taatgttttt aaatatattt tcaaagtaca taaaactcga   4560
gccatgggcg cgccatcgat gaggaacccc tagtgatgga gttggccact ccctctctgc   4620
gcgctcgctc gctcactgag gccgggcgac caaaggtcgc ccgacgcccg ggctttgccc   4680
gggcggcctc agtgagcgag cgagcgcgca gctgcctgca gg                      4722
```

<210> SEQ ID NO 34
<211> LENGTH: 4185
<212> TYPE: DNA
<213> ORGANISM: Artificial Sequence
<220> FEATURE:
<223> OTHER INFORMATION: AD-dmScar-bGH Construct

<400> SEQUENCE: 34

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggg ttcc ttgcgtcgac aggcctccta gcggaccgc ttgcatgcac   180 gcgtgggtgg tgcagagtct gcatgcgtga ggagctcctg ggcgcgtcac agccgcgcta   240
ttctcagcgt ctctcctttt atggctccgg aagtgagctg gggttgctgg cagccgtccc   300
tcggtccccg caggctgaat gagccccgcc gtccggggtg ggaggtacgg agcggaggga   360
ttagtcatcc tggcccccgcc atgtgtgcag ggggtgggac ctcccgtccc ttgccgcccg   420
ggagccgagt gggcgcaggg cggggcctgc aggggcgcgg gcggggcgct ggcggggagc   480
ctgcggctgg gccaatgaga aaccgggctc ggcgagccgg ccgcccacgg gcctcgctgg   540
ctgcataaag agccggcggc caggactcag cgcagagctc gggcgcggcg tcctccctcc   600
gcagcagccg agccggacct gcctcccccgg gcgtgctccg ccggcccgc cgccggcccg   660 cagcgacaga caggcgctcc ccgcagctcc gcacgggacc caggccgccg accccagcg    720 ccggaccacc ctctgtccgc cccgaggagt ttgccgcctg ccggagcacc tgcgcacaga   780
ccggtcgcca ccatggtgag caagggcgag cagtgatca aggagttcat gcggttcaag   840
gtgcacatgg agggctccat gaacggccac gagttcgaga tcgagggcga gggcgagggc   900
```

```
cgccoctacg agggcaccca gaccgccaag ctgaaggtga ccaagggtgg cccctgccc      960
ttctcctggg acatcctgtc ccctcagttc atgtacggct ccagggcctt catcaagcac   1020
cccgccgaca tccccgacta ctataagcag tccttcccg agggcttcaa gtgggagcgc    1080
gtgatgaact cgaggacgg cggcgccgtg accgtgaccc aggacacctc cctggaggac    1140
ggcaccctga tctacaaggt gaagctccgc ggcaccaact ccctcctga cggccccgta    1200
atgcagaaga agacaatggg ctgggaagcg tccaccgagc ggttgtaccc cgaggacggc   1260
gtgctgaagg gcgacattaa gatggccctg cgcctgaagg acggcggccg ctacctggcg   1320
gacttcaaga ccacctacaa ggccaagaag cccgtgcaga tgcccggcgc ctacaacgtc   1380
gaccgcaagt tggacatcac ctcccacaac gaggactaca ccgtggtgga acagtacgaa   1440
cgctccgagg gccgccactc caccggcggc atggacgagc tgtacaagaa gcttccgcgg   1500
agccatggct cccgccggc ggtggcggcg caggatgatg gcacgctgcc catgtcttgt    1560
gcccaggaga gcgggatgga ccgtcaccct gcagcctgtg cttctgctag gatcaatgtg   1620
tagggtaccc tgtgccttct agttgccagc catctgttgt tgcccctcc ccgtgccett    1680
ccttgaccct ggaaggtgcc actcccactg tcctttccta ataaaatgag gaaattgcat   1740
cgcattgtct gagtaggtgt cattctattc tgggggtgg ggtggggcag gacagcaagg    1800
gggaggattg gaagacaat agcaggcatg ctggggatgc ggtgggctct atgggcgcgc    1860
catcgatgtg aagtgggtaa cctttatttc ccttctttt ctctttagct cggcttattc    1920
caggggtgtg tttcgtcgag atgcacacaa gagtgaggtt gctcatcggt ttaaagattt    1980
gggagaagaa aatttcaaag ccttggtgtt gattgccttt gctcagtatc ttcagcagtg   2040
tccatttgaa gatcatgtaa aattagtgaa tgaagtaact gaatttgcaa aaacatgtgt   2100
tgctgatgag tcagctgaaa attgtgcaca atcacttcat accctttttg gagacaaatt   2160
atgcacagtt gcaactcttc gtgaaaccta tggtgaaatg gctgactgct gtgcaaaaca   2220
agaacctgag agaaatgaat gcttcttgca acacaaagat gacaacccaa acctcccccg   2280
attggtgaga ccagaggttg atgtgatgtg cactgctttt catgacaatg aagagacctt   2340
tttgaaaaaa tacttatacg aaattgccag aagacatcct tacttttatg ccccggaact   2400
ccttttcttt gctaaaaggt ataaagctgc ttttacagaa tgttgccaag ctgctgataa   2460
agctgcctgc ctgttgccaa agctcgatga acttcgggat gaagggaagg cttcgtctgc   2520
caaacagaga ctcaagtgtg ccagtctcca aaaatttgga gaaagagctt tcaaagcatg   2580
ggcagtagct cgcctgagcc agagatttcc caaagctgag tttgcagaag tttccaagtt   2640
agtgacagat cttaccaaag tccacacgga atgctgccat ggagatctgc ttgaatgtgc   2700
tgatgacagg gcggaccttg ccaagtatat ctgtgaaaat caagattcga tctccagtaa   2760
actgaaggaa tgctgtgaaa acctctgtt ggaaaaatcc cactgcattg ccgaagtgga    2820
aaatgatgag atgcctgctg acttgccttc attagctgct gattttgttg aaagtaagga   2880
tgtttgcaaa aactatgctg aggcaaagga tgtcttcctg gcatgttttt gtatgaata    2940
tgcaagaagg catcctgatt actctgtcgt gctgctgctg agacttgcca agacctatga   3000
aaccactcta gagaagtgct gtgccgctgc agatcctcat gaatgctatg ccaaagtgtt   3060
cgatgaattt aaacctcttg tggaagagcc tcagaattta atcaaacaaa attgtgagct   3120
ttttgagcag cttggagagt acaaattcca gaatgcgcta ttagttcgtt acaccaagaa   3180
agtaccccaa gtgtcaactc caactcttgt agaggtctca agaaacctag gaaaagtggg   3240
cagcaaatgt tgtaaacatc ctgaagcaaa aagaatgccc tgtgcagaag actatctatc   3300
```

```
cgtggtcctg aaccagttat gtgtgttgca tgagaaaacg ccagtaagtg acagagtcac    3360
caaatgctgc acagaatcct tggtgaacag gcgaccatgt cgtgaaacct atggtgaaat    3420
ggctgactgc tgtgcaaaac aagaacctga gagaaatgaa tgcttcttgc aacacaaaga    3480
tgacaaccca aacctccccc gattggtgag accagaggtt gatgtgatgt gcactgcttt    3540
tcatgacaat gaagagacct ttttgaaaaa atacttatac gaaattgcca gaagacatcc    3600
ttacttttat gccccggaac tccttttctt tgctaaaagg tataaagctg cttttacaga    3660
atgttgccaa gctgctgata agctgcctg cctgttgcca agctcgatg aacttcggga    3720 tgaagggaag gcttcgtctg ccaaacagag actcaagtgt gccagtctcc aaaaatttgg    3780
agaaagagct ttcaaagcat gggcagtagc tcgcctgagc cagactttc agctctggaa    3840 gtcgatgaaa catacgttcc caaagagttt aatgctgaaa cattcacctt ccatgcagat    3900
atatgcacac tttctgagaa ggagagacaa atcaagaaac aaactgcact tgttgagctc    3960
gtgaaacaca agcccaaggc aacaaaagag caactgaaag ctgttatgga tgatttcgct    4020
cgagccatgg gcgcgccatc gatgaggaac ccctagtgat ggagttggcc actccctctc    4080
tgcgcgctcg ctcgctcact gaggccgggc gaccaaaggt cgcccgacgc ccgggctttg    4140
cccgggcggc ctcagtgagc gagcgagcgc gcagctgcct gcagg                   4185
```

<210> SEQ ID NO 35
<211> LENGTH: 831
<212> TYPE: DNA
<213> ORGANISM: Artificial Sequence
<220> FEATURE:
<223> OTHER INFORMATION: dmScarlet (mScarlet-I with Cterminal PEST
      degron)

<400> SEQUENCE: 35

```
atggtgagca agggcgaggc agtgatcaag gagttcatgc ggttcaaggt gcacatggag     60
ggctccatga acgccacga gttcgagatc gagggcgagg gcgagggccg cccctacgag    120
ggcacccaga ccgccaagct gaaggtgacc aagggtggcc ccctgccctt ctcctgggac    180
atcctgtccc ctcagttcat gtacggctcc agggccttca tcaagcaccc cgccgacatc    240
cccgactact ataagcagtc cttccccgag ggcttcaagt gggagcgcgt gatgaacttc    300
gaggacggcg gcgccgtgac cgtgacccag gacacctccc tggaggacgg caccctgatc    360
tacaaggtga agctccgcgg caccaacttc cctcctgacg gccccgtaat gcagaagaag    420
acaatgggct gggaagcgtc caccgagcgg ttgtaccccg aggacggcgt gctgaagggc    480
gacattaaga tggccctgcg cctgaaggac ggcggccgct acctggcgga cttcaagacc    540
acctacaagg ccaagaagcc cgtgcagatg cccggcgcct acaacgtcga ccgcaagttg    600
gacatcacct cccacaacga ggactacacc gtggtggaac agtacgaacg ctccgagggc    660
cgccactcca ccggcggcat ggacgagctg tacaagaagc ttccgcggag ccatggcttc    720
ccgccggcgg tggcggcgca ggatgatggc acgctgccca tgtcttgtgc ccaggagagc    780
gggatggacc gtcaccctgc agcctgtgct tctgctagga tcaatgtgta g             831
```

<210> SEQ ID NO 36
<211> LENGTH: 696
<212> TYPE: DNA
<213> ORGANISM: Artificial Sequence
<220> FEATURE:
<223> OTHER INFORMATION: mScarlet-I

<400> SEQUENCE: 36

```
atggtgagca agggcgaggc agtgatcaag gagttcatgc ggttcaaggt gcacatggag      60
ggctccatga acggcacga gttcgagatc gagggcgagg cgagggccg ccctacgag       120
ggcacccaga ccgccaagct gaaggtgacc aagggtggcc ccctgccctt ctcctgggac    180
atcctgtccc ctcagttcat gtacggctcc agggccttca tcaagcaccc cgccgacatc    240
cccgactact ataagcagtc cttccccgag gccttcaagt gggagcgcgt gatgaacttc    300
gaggacggcg gcgccgtgac cgtgacccag gacacctccc tggaggacgg caccctgatc    360
tacaaggtga agctccgcgg caccaacttc cctcctgacg ccccgtaat gcagaagaag    420
acaatgggct gggaagcgtc caccgagcgg ttgtaccccg aggacggcgt gctgaagggc    480
gacattaaga tggccctgcg cctgaaggac ggcggccgct acctggcgga cttcaagacc    540
acctacaagg ccaagaagcc cgtgcagatg cccggcgcct acaacgtcga ccgcaagttg    600
gacatcacct cccacaacga ggactacacc gtggtggaac agtacgaacg ctccgagggc    660
cgccactcca ccggcggcat ggacgagctg tacaag                              696
```

<210> SEQ ID NO 37
<211> LENGTH: 135
<212> TYPE: DNA
<213> ORGANISM: Artificial Sequence
<220> FEATURE:
<223> OTHER INFORMATION: C-terminal PEST degron

<400> SEQUENCE: 37

```
aagcttccgc ggagccatgg cttcccgccg gcggtggcgg cgcaggatga tggcacgctg      60
cccatgtctt gtgcccagga gagcgggatg gaccgtcacc ctgcagcctg tgcttctgct    120
aggatcaatg tgtag                                                      135
```

<210> SEQ ID NO 38
<211> LENGTH: 448
<212> TYPE: DNA
<213> ORGANISM: Artificial Sequence
<220> FEATURE:
<223> OTHER INFORMATION: hSyn

<400> SEQUENCE: 38

```
agtgcaagtg ggttttagga ccaggatgag gcggggtggg ggtgcctacc tgacgaccga      60
ccccgaccca ctggacaagc acccaacccc cattccccaa attgcgcatc ccctatcaga    120
gaggggagg ggaaacagga tgcggcgagg cgcgtgcgca ctgccagctt cagcaccgcg     180
gacagtgcct tcgccccgc ctggcggcg cgccaccgc cgcctcagca ctgaaggcgc       240
gctgacgtca ctcgccggtc ccccgcaaac tccccttccc ggccaccttg gtcgcgtccg    300
cgccgccgcc ggcccagccg gaccgcacca cgcgaggcgc gagatagggg ggcacgggcg    360
cgaccatctg cgctgcggcg ccggcgactc agcgctgcct cagtctgcgg tgggcagcgg    420
aggagtcgtg tcgtgcctga gagcgcag                                        448
```